US012037372B2

(12) United States Patent
Kerkkamp et al.

(10) Patent No.: US 12,037,372 B2
(45) **Date of Patent: *Jul. 16, 2024**

(54) BIOACTIVE PEPTIDES DERIVED FROM SNAKES

(71) Applicants: Universiteit Leiden, Leiden (NL); Academisch Ziekenhuis Leiden h.o.d.n. LUMC, Leiden (NL)

(72) Inventors: Harald Martijn Ijsbrand Kerkkamp, The Hague (NL); Michael Keith Richardson, Leiderdorp (NL); Gilles Philippus van Wezel, Heemstede (NL); Jan Wouter Drijfhout, Leiden (NL); Robert Alexander Cordfunke, Delft (NL); Michella Manon Voet, Haarlem (NL); Petrus Hendricus Nibbering, Voorhout (NL)

(73) Assignees: Universiteit Leiden, Leiden (NL); Academisch Ziekenhuis Leiden h.o.d.n. LUMC, Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/322,507

(22) Filed: May 23, 2023

(65) Prior Publication Data

US 2023/0391839 A1 Dec. 7, 2023

Related U.S. Application Data

(63) Continuation of application No. 17/276,452, filed as application No. PCT/NL2019/050612 on Sep. 17, 2019, now Pat. No. 11,680,088.

(30) Foreign Application Priority Data

Sep. 17, 2018 (EP) .................................... 18194912

(51) Int. Cl.

*A61K 38/16* (2006.01)
*C07K 14/46* (2006.01)
*A61K 38/00* (2006.01)

(52) U.S. Cl.

CPC .............. *C07K 14/46* (2013.01); *A61K 38/00* (2013.01)

(58) Field of Classification Search

None

See application file for complete search history.

(56) References Cited

U.S. PATENT DOCUMENTS

2020/0165309 A1 5/2020 Yount et al.

FOREIGN PATENT DOCUMENTS

| | | | |
|---|---|---|---|
| CN | 102311492 | A | 1/2012 |
| WO | 2010/148079 | A1 | 12/2010 |
| WO | 2014/060610 | A2 | 4/2014 |
| WO | 2017/176041 | A1 | 10/2017 |

OTHER PUBLICATIONS

Bahar et al. "Antimicrobial Peptides" Pharmaceuticals, vol. 6 (Nov. 28, 2013) pp. 1543-1575.

Boucher et al. "Bad Bugs, No. Drugs: No ESKAPE! An Update from the Infectious Diseases Society of America" Clin. Infect. Dis; 48 (Jan. 2009) 12 pages.

Brauner et al. "Distinguishing between resistance, tolerance and persistence to antibiotic treatment" Nat Rev Microbiol; vol. 14 (5) (Apr. 2016) pp. 321-330.

Cai et al. "Python Cathelicidin CATHPb1 Protects against Multidrug-Resistant Staphylococcal Infections by Antimicrobial-Immunomodulatory Duality" Journal of Medicinal Chemistry, vol. 61 (Feb. 21, 2018) pp. 2075-2086.

Cho et al. "Enhanched IL-12p40 production in LPS-stimulated macrophages by inhibiting JNK activation by artemisinin." Arch Pharm. Res; vol. 35 (Nov. 2012) pp. 1951-1968.

De Kraker et al. "Will 10 Million People Die a Year due to Antimicrobial Resistance by 2050?" PLoS Med; vol. 13:11 (Nov. 2016) e1002184.

De Latour et al. "Antimicrobial activity of the Naja atra cathelicidin and related small peptides" Biochemical and Biophysical Research Communications; vol. 396 (May 10, 2010) pp. 825-830.

Dean et al. "Natural and synthetic cathelicidin peptides with anti-microbial and anti-biofilm activity against *Staphylococcus aureus*" BMC Microbiology 11 Article 114 ( May 23, 2011) https://doi.org/10.1186/1471-2180-11-114.

Falcao et al. "Vipericidins; a novel family of cathelicidin-related peptides from the venom gland of South American pit vipers" Amino Acids; vol. 46 (Jun. 2014) pp. 2561-2571.

Hoiby et al. "Antibiotic resistance of bacterial biofilms" Int J Antimicrob Agents, (Apr. 2010) 35(4):322-32.

International Search Report for International Application No. PCT/NL2019/050612, mailed Jun. 29, 2021, 7 pages.

International Written Opinion for International Application No. PCT/NL2019/050612, mailed Jun. 29, 2021, 10 pages.

Kosciuczuk et al. "Cathelicidins: family of antimicrobial peptides. A review" Mol Biol Rep (Oct. 2012) 39:10957-10970 https://doi.org/10.1007/s11033-012-1997-x.

O'Neil "Tackling drug-resistant infections globally: Final report and recommendations" 2016; on the world-wide web at amr-review.org/sites/default/files/160518_Final%20paper_with%20cover.pdf (accessed Jul. 26, 2022).

Olsen "Biofilms-specific antibiotic tolerance and resistance" Eur. J. Clin. Microbiol. Infect. Dis; vol. 34 (May 2015) pp. 877-886 abstract only.

Overhage et al. "Human Host Defense Peptide LI-37 Prevents Bacterial Biofilm Formation" Infection and Immunity, p. 4176-4182 vol. 76, No. 9 (Sep. 2008).

(Continued)

*Primary Examiner* — Fred H Reynolds

(74) *Attorney, Agent, or Firm* — TraskBritt

(57) ABSTRACT

The disclosure concerns snake-derived peptides and the useful application of such peptides to inhibit bacterial, fungal, viral and parasitic infections. The disclosed peptides are also useful for the treatment of an inflammatory condition or cancers.

9 Claims, 10 Drawing Sheets

Specification includes a Sequence Listing.

(56) References Cited

OTHER PUBLICATIONS

Scott et al. "The Human Antimicrobial Peptide LL-37 is a Multifunctional Modulator of Innate Immune Responses" The Journal of Immunology, 2002; vol. 169, pp. 3883-3891 (Downloaded from http://www.jimmunol.org/ on Mar. 17, 2022).
Shek et al. "Oral bacterial flora of the Chinese cobra (*Naja atra*) and bamboo pit viper (*Trimeresurus albolabris*) in Hong Kong SAR, China" Hong Kong Med. J.; vol. 15 (Jun. 2009) pp. 183-190.
Van Der Does et al. "LL-37 directs macrophage differentiation toward macrophages with a pro-inflammatory signature" J. Immunol; vol. 185 (Aug. 2010) pp. 1442-1449.
Von Rosenvinge et al. "Microbial biofilms and gastrointestinal diseases" Pathogens and Disease, vol. 67, Issue 1 (Feb. 2013) pp. 25-38.
Wang et al. "BF-30 selectively inhibits melanoma cell proliferation via cytoplasmic membrane permeabilization and DNA-binding in vitro and in B16F10-bearing mice" Eur. J. Pharmacol; vol. 707 (Mar. 2013) 10 pages.
Zhao et al. "King cobra peptide OH-CATH30 as a potential candidate drug through clinic drug-resistant isolates" Zoological research; vol. 39 (Feb. 2018) pp. 87-96.

BIOACTIVE PEPTIDES DERIVED FROM SNAKES

CROSS-REFERENCE TO RELATED APPLICATIONS

This application is a continuation of U.S. patent application Ser. No. 17/276,452, filed Mar. 15, 2021, which is a national phase entry under 35 U.S.C. § 371 of International Patent Application PCT/NL2019/050612, filed Sep. 17, 2019, designating the United States of America and published as International Patent Publication WO 2020/060401 A2 on Mar. 26, 2020, which claims the benefit under Article 8 of the Patent Cooperation Treaty to European Patent Application Serial No. 18194912.4, filed Sep. 18, 2019, the disclosure of each of which is hereby incorporated herein in its entirety by this reference.

TECHNICAL FIELD

The application concerns biology and peptides generally and more specifically the useful application of such peptides to inhibit bacterial, fungal, viral and parasitic infections. The disclosed peptides are also useful for treating inflammatory conditions or cancers.

STATEMENT ACCORDING TO 37 C.F.R. § 1.835(a)(2) or (b)(2)

Pursuant to 37 C.F.R. § 1.821(c) or (e) 1.835(a)(2) or 1.835(b)(2), an XML Document of the Sequence Listing entitled P119298US10-sequence listing of 211 KB and dated Aug. 23, 2023 has been submitted for this application, the contents of which are hereby incorporated by reference.

BACKGROUND

Bacterial infections are a major cause of disease and death worldwide. In addition, resistance against antibiotics among bacteria is nowadays a major threat to society. It is expected that—if no solutions are introduced—in 2050 there will be 10 million deaths yearly due to infections with antimicrobial resistant (AMR) microorganisms (de Kraker et al., 2016, O'Neill 2016). The top six most threatening bacteria include AMR *Enterococcus faecium, Staphylococcus aureus, Klebsiella pneumoniae, Acinetobacter baumannii, Pseudomonas aeruginosa*, and *Enterobacter* species, further referred to as the ESKAPE bacteria (Boucher et al., 2009). Infections by Gram-negative bacteria are currently considered as the major threat to human health, in particular due to emerging resistance and lack of classes of antibiotics.

Antibiotics are poorly effective in degrading bacterial biofilms. Elimination of bacteria within a biofilm requires 100-1000 times higher concentrations of antibiotics than planktonic bacteria (N. Høibyet al., 2010; Olsen 2015). In a biofilm, the bacteria are surrounded by a matrix of extracellular polysaccharides, DNA and proteins. This matrix may protect the bacteria residing within biofilms from the actions of antibiotics by limiting the penetration into the matrix (Olsen 2015). The impaired activity of antibiotics on biofilm bacteria is also due to the presence of metabolically inactive bacteria within biofilms, referred to as persisters (Høibyet al., 2010; Olsen 2015). Persisters are tolerant to antibiotics, which may lead to chronic, recurrent infections. Novel antibacterial agents are urgently needed, in particular as agents against antibiotic resistant as well as tolerant pathogens and to prevent and/or disrupt biofilms.

BRIEF SUMMARY

In one aspect, provided is an isolated or recombinant peptide having up to 200 amino acids and a) comprising at least 60% of an amino acid sequence selected from:

SP1
(SEQ ID NO: 1)
RKFKKSFKKIRKWVKKATKIAGEVAVEILITKVILGSVGL

SP2
(SEQ ID NO: 2)
KRVKRFKKFFKKVKKSVKKRLKKIFKKPMVIGVTIPF

SP3
(SEQ ID NO: 3)
KRFKKFFKKLKNSVKKRVKKFFRKPRVIGVTFPF

SP4
(SEQ ID NO: 4)
KRFKKFFKKLKNNVKKRVKKFFRKPRVIGVTIPF

SP5
(SEQ ID NO: 5)
KRFKKFFRKLKKSVKKRAKEFFKKPRVIGVSIPF

SP6
(SEQ ID NO: 6)
KRFKKFFKKVKKSVKKRLKKIFKKPMVIGVTIPF

SP7
(SEQ ID NO: 7)
KRFKKFFKKVKKSVKKRLKKIFKKPMVIGVSIPF

SP8
(SEQ ID NO: 8)
KRFRKFFKRLLKSVRRAVKKFRKKPRLIGLSTLL

SP9
(SEQ ID NO: 9)
KRFKKFFKKVKKSVKKRLKKIFKKPMVIGVTFPF

SP11
(SEQ ID NO: 10)
KRFKKFFRKLKKSVKKRVKKFFKKPRVIGVTIPF

SP12
(SEQ ID NO: 11)
KRFKKFFMKLKKSVKKRVMKFFKKPMVIGVTFPF

SP14
(SEQ ID NO: 12)
KRFKKFFKKAKKSVKKRLKKFFNKTRVIGVSIPF

SP15
(SEQ ID NO: 13)
KRFKKFFRKIKKGFRKIFKKTKIFIGGTIPI

SP16
(SEQ ID NO: 14)
KRFQNFFRELEKKFREFFRVYRITIGATIRF

SP17
(SEQ ID NO: 15)
KRFKDFFHRIRDGVRDFFRNNHFVCGVNFRF

SP18
(SEQ ID NO: 16)
KRFKKFFKKIKTGIKKVIKKTKQAIASHFRW

SP19
(SEQ ID NO: 17)
KRFLRVFKKLKRGIRKLFKKKKIVTGPLTS

SP20
(SEQ ID NO: 18)
AREKSFLQKMKVILQLSSQDQIQAF

SP21
(SEQ ID NO: 19)
KRFAGFFQFVIGVSFHF

-continued

SP22

(SEQ ID NO: 20)
DQVERGNFAKDGSKARVKKSLTKWVKFLKKIIAKLGRPLIGF

SP23

(SEQ ID NO: 21)
KRFKKFFKKIKNSVKKRVKKFFKKPRVIGVSIPF

SP24

(SEQ ID NO: 22)
KRFKKFFKKLKNSVRKCAKKFFKKLRVIRVSIPF

SP25

(SEQ ID NO: 23)
KRFKKFFKKVKKSVKKRLKKIFKKPIVIGVSIPF

SP26

(SEQ ID NO: 24)
KRFTFYKKVKKNVENLLNKFFKKLRVIGDSIPF

SP27

(SEQ ID NO: 25)
KRFKKFFRKVKKGVHRYFKKNKFYIAATIPYYG

SP28

(SEQ ID NO: 26)
KRFLRLVVFKKLKKGLRKLFKKKKIVTGHVTS

SP29

(SEQ ID NO: 27)
KRFKNFFKKIRDGIHEFIHNNRFVIGVNFRF

SP30

(SEQ ID NO: 28)
KRFKKFFKKIKNGIKTFIKKTQMAIGSHFRW

SP31

(SEQ ID NO: 29)
KRFKNFFKRVRDGIRDFFRKNHIVIGVNFRF

SP32

(SEQ ID NO: 30)
KRFLRVFRKLKKGLKKLFKRKKVVTGYVTA

SP33

(SEQ ID NO: 31)
KRFAGFFQFVVGVSFRF

SP34

(SEQ ID NO: 32)
KRFVGSFQLVVGVSFRF
and

SP35

(SEQ ID NO: 33)
KRFKKFLKKLKKSVKKHVKEFFKKPRVIGV;
preferably wherein the sequence is selected from (SP27)

(SEQ ID NO: 25)
KRFKKFFRKVKKGVHRYFKKNKFYIAATIPYYG, (SP11)

(SEQ ID NO: 10)
KRFKKFFRKLKKSVKKRVKKFFKKPRVIGVTIPF,
and (SP23)

(SEQ ID NO: 21)
KRFKKFFKKIKNSVKKRVKKFFKKPRVIGVSIPF;

b) comprising at least 60% of consecutive amino acids of a retro-inverso sequence of the sequences; or c) a functional variant of a) or b), wherein the variant has one or more substitutions of an amino acid by a corresponding non-natural amino acid, has one or more substitutions of an amino acid by a corresponding D-amino acid, and/or has up to 5 amino acid substitutions, preferably wherein the amino acid substitutions are conservative amino acid substitutions.

In preferred embodiments, the amino acid sequence comprises at least 80% of the sequences.

In one aspect, provided is an isolated or recombinant peptide having between 20-200 amino acids, the peptide comprising:

a) at least 20 consecutive amino acids of an amino acid sequence selected from:

(SP27)

(SEQ ID NO: 25)
KRFKKFFRKVKKGVHRYFKKNKFYIAATIPYYG, (SP11)

(SEQ ID NO: 10)
KRFKKFFRKLKKSVKKRVKKFFKKPRVIGVTIPF,
and (SP23)

(SEQ ID NO: 21)
KRFKKFFKKIKNSVKKRVKKFFKKPRVIGVSIPF;

b) at least 20 consecutive amino acids of a retro-inverso sequence of a); or c) a functional variant of a) or b), wherein the variant:
   has one or more substitutions of an amino acid by a corresponding non-natural amino acid;
   has one or more substitutions of an amino acid by a corresponding D-amino acid; and/or
   has up to 5 amino acid substitutions, preferably wherein the amino acid substitutions are conservative amino acid substitutions.

Preferably the polypeptide further comprises:

a) at least an amino acid sequence VKKGVHRYFKKNKFY (SEQ ID NO:34), b) the retro-inverso sequence of a); or c) a functional variant of a) or b), wherein the variant has up to 2 substitutions selected from:
   substitutions of an amino acid by a corresponding non-natural amino acid;
   substitutions of an amino acid by a corresponding D-amino acid; and/or
   amino acid substitutions, preferably wherein the amino acid substitutions are conservative amino acid substitutions.

In one aspect, provided is an isolated or recombinant peptide having between 20-200 amino acids, a nucleic acid molecule encoding the peptide, or a composition comprising the peptide or the nucleic acid for use in therapy as an anti-bacterial, antiviral, antifungal, anti-parasitic, anti-inflammatory, immune-modulating, and/or anti-cancer agent, the peptide comprises:

a) at least 20 consecutive amino acids of the amino acid sequence (SP4)

(SEQ ID NO: 4)
KRFKKFFKKLKNNVKKRVKKFFRKPRVIGVTIPF;

b) at least 20 consecutive amino acids of a retro-inverso sequence of a); or c) a functional variant of a) or b), wherein the variant:
   has one or more substitutions of an amino acid by a corresponding non-natural amino acid;
   has one or more substitutions of an amino acid by a corresponding D-amino acid; and/or
   has up to 5 amino acid substitutions, preferably wherein the amino acid substitutions are conservative amino acid substitutions.

In one aspect, provided is a nucleic acid molecule comprising a nucleic acid sequence ("polynucleotide") encoding a peptide as disclosed herein. In one aspect, provided is a vector comprising the nucleic acid molecule as disclosed herein. Preferably the vector is an expression vector.

In one aspect, provided is a recombinant host cell comprising the nucleic acid molecule and/or the vector as disclosed herein. Preferably, the host cell is a mammalian, human, plant, bacterial and/or yeast cell.

In one aspect, provided is a composition comprising the peptide, the nucleic acid molecule and/or the vector as disclosed herein, wherein the composition is selected from a pharmaceutical composition comprising at least one pharmaceutically acceptable carrier, diluent and/or excipient; a cosmetic product; a food product; an oral care product; a cleaning product or an ophthalmic product. In some embodiments, the peptide, the nucleic acid molecule, the vector and/or the composition as disclosed herein are provided as a medicament.

In one aspect, provided is an article coated with the isolated or recombinant peptide as disclosed herein. Preferably wherein the article is a medical device and/or surgical instrument.

In some embodiments, the peptide, the nucleic acid molecule, the vector and/or the composition as disclosed herein is for use in therapy. Preferably, the therapy is for the treatment of a bacterial, fungal, viral and/or parasitic infection, an inflammatory condition, or a carcinoma. Preferably, the therapy is for the treatment of a condition resulting from bacterial, fungal, viral and/or parasitic infection, biofilm formation, an inflammatory condition, and/or a carcinoma. Preferably the peptide as disclosed herein has bioactivity against Gram-negative bacteria.

In one aspect, provided is the use of the isolated or recombinant peptide as disclosed herein to inhibit biofilm formation or to degrade biofilms; as an anti-bacterial agent, anti-fungal agent, antiviral agent, anti-parasitic agent, as a diagnostic, crop protectant, disinfectant, preservative anti-inflammatory agent, immune-modulating agent and/or anti-cancer agent, preferably wherein the use does not comprise the treatment of a human or animal body.

In some embodiments, the isolated or recombinant peptide, the nucleic acid molecule, or the composition for use in therapy as an anti-bacterial agent as disclosed herein, wherein the bacteria are antibiotic resistant bacteria, antibiotic tolerant bacteria, persistent bacteria, antibiotic persistent bacteria and/or a biofilm, preferably wherein the bacteria is antibiotic tolerant bacteria or part of a biofilm.

In some embodiments, the peptide or peptide for use as disclosed herein, is N-terminally and/or C-terminally modified, or the peptide is in a cyclic confirmation.

In preferred embodiments, the peptide is N-terminally and/or C-terminally modified with a Polyethylene glycol (PEG) group, polysaccharide and/or lipid.

In some embodiments, the peptide or a functional variant as disclosed herein comprises up to 200 amino acids, preferably between 25-200 amino acids. In some embodiments, the peptide or a functional variant comprises 25-100 amino acids, preferably 30-50 amino acids.

In some embodiments, the peptide or a functional variant as disclosed herein comprises up to 200 amino acids, preferably between 15-200 amino acids. In some embodiments, the peptide or a functional variant comprises 15-100 amino acids, preferably 15-50 amino acids, preferably 15-40 amino acids.

In some embodiments, the peptide or a functional variant as disclosed herein comprises up to 200 amino acids, preferably between 20-200 amino acids. In some embodiments, the peptide or a functional variant comprises 20-100 amino acids, preferably 20-50 amino acids, preferably 20-40 amino acids.

In some embodiments, the peptide or a functional variant as disclosed herein comprises up to 200 amino acids, preferably between 23-200 amino acids. In some embodiments, the peptide or a functional variant comprises 23-100 amino acids, preferably 23-50 amino acids, preferably 23-40 amino acids.

In some embodiments, the peptide or a functional variant as disclosed herein comprises up to 200 amino acids, preferably between 24-200 amino acids. In some embodiments, the peptide or a functional variant comprises 24-100 amino acids, preferably 24-50 amino acids, preferably 24-40 amino acids.

In one aspect, provided is a method of treating a subject in need thereof comprising administering to the subject a therapeutically effective amount of the peptide, the nucleic acid molecule, the vector and/or the composition as disclosed herein.

In one aspect, provided is a method of treating or preventing a bacterial, fungal, viral and/or parasitic infection in a subject in need thereof comprising administering to the subject a therapeutically effective amount of the peptide, the nucleic acid molecule, the vector and/or the composition as disclosed herein. In some embodiments, the subject has been diagnosed with a bacterial, fungal, viral and/or parasitic infection.

In one aspect, provided is a method of inhibiting biofilm formation or degrading a biofilm in a subject in need thereof comprising administering to the subject the peptide, the nucleic acid molecule, the vector and/or the composition as disclosed herein. In some embodiments, the subject has been implanted with a medical device.

In one aspect, provided is a method of treating an inflammatory disorder, preferably an auto-immune disease, or modulating an immune response in a subject in need thereof comprising administering to the subject a therapeutically effective amount of the peptide, the nucleic acid molecule, the vector and/or the composition as disclosed herein.

In one aspect, provided is a method of treating a cancer in a subject in need thereof comprising administering to the subject a therapeutically effective amount of the peptide, the nucleic acid molecule, the vector and/or the composition as disclosed herein.

In one aspect, provided is a method of inhibiting biofilm formation on a surface or degrading biofilm from a surface, the method comprising contacting the surface with the isolated or recombinant peptide and/or the composition as disclosed herein.

In one aspect, provided is, a method of eliminating, inhibiting, or reducing bacteria, viruses, fungi, and/or parasites, comprising providing the isolated or recombinant peptide and/or the composition as disclosed herein.

In one aspect, provided is a method of disinfecting a surface, or composition, the method comprising contacting the surface and/or composition or providing the surface or composition with the isolated or recombinant peptide and/or the composition as disclosed herein.

In one aspect, provided is a method of preparing a composition, the method comprising providing the surface or composition with the isolated or recombinant peptide and/or the composition as disclosed herein. In some embodiments, the isolated or recombinant peptide acts as a preservative.

In one aspect, provided is a method of protecting a plant from infection, the method comprising providing the isolated or recombinant peptide as disclosed herein to the plant, preferably crop plant.

In one aspect, provided is a method of modulating an immune response, preferably inhibiting or redirecting an immune response; reducing cancers; or inhibiting bacteria, viruses, fungi, and/or parasites in a system comprising providing the isolated or recombinant peptide, the nucleic acid molecule, the vector and/or the composition as disclosed herein to the system. In some embodiments, the system comprises in vitro cells or a cell culture.

In one aspect, provided is a method of inhibiting biofilm formation to a surface or degrading biofilm from a surface, the method comprising contacting the surface with an isolated or recombinant peptide and/or a composition as disclosed herein.

In one aspect, provided is a method of treating a bacterial infection in a subject in need thereof as disclosed herein, wherein the bacteria are antibiotic resistant bacteria, antibiotic tolerant bacteria and/or bacteria residing within a biofilm, including persisters.

Further provided are methods for treating an individual in need thereof, comprising implanting a medical device at least partially coated with a peptide as disclosed herein into an individual in need thereof.

In one aspect, provided is an isolated or recombinant peptide having up to 200 amino acids for use in therapy, the peptide:

a) comprising at least 60% of an amino acid sequence selected from:

```
SP1
                                    (SEQ ID NO: 1)
RKFKKSFKKIRKWVKKATKIAGEVAVEILITKVILGSVGL,

SP2
                                    (SEQ ID NO: 2)
KRVKRFKKFFKKVKKSVKKRLKKIFKKPMVIGVTIPF,

SP3
                                    (SEQ ID NO: 3)
KRFKKFFKKLKNSVKKRVKKFFRKPRVIGVTFPF,

SP5
                                    (SEQ ID NO: 5)
KRFKKFFRKLKKSVKKRAKEFFKKPRVIGVSIPF,

SP6
                                    (SEQ ID NO: 6)
KRFKKFFKKVKKSVKKRLKKIFKKPMVIGVTIPF,

SP7
                                    (SEQ ID NO: 7)
KRFKKFFKKVKKSVKKRLKKIFKKPMVIGVSIPF,

SP8
                                    (SEQ ID NO: 8)
KRFRKFFKRLLKSVRRAVKKFRKKPRLIGLSTLL,

SP9
                                    (SEQ ID NO: 9)
KRFKKFFKKVKKSVKKRLKKIFKKPMVIGVTFPF,

SP12
                                   (SEQ ID NO: 11)
KRFKKFFMKLKKSVKKRVMKFFKKPMVIGVTFPF,

SP14
                                   (SEQ ID NO: 12)
KRFKKFFKKAKKSVKKRLKKFFNKTRVIGVSIPF,
```

-continued

```
SP15
                                   (SEQ ID NO: 13)
KRFKKFFRKIKKGFRKIFKKTKIFIGGTIPI,

SP16
                                   (SEQ ID NO: 14)
KRFQNFFRELEKKFREFFRVYRITIGATIRF,

SP17
                                   (SEQ ID NO: 15)
KRFKDFFHRIRDGVRDFFRNNHFVCGVNFRF,

SP18
                                   (SEQ ID NO: 16)
KRFKKFFKKIKTGIKKVIKKTKQAIASHFRW,

SP19
                                   (SEQ ID NO: 17)
KRFLRVFKKLKRGIRKLFKKKKIVTGPLTS,

SP20
                                   (SEQ ID NO: 18)
AREKSFLQKMKVILQLSSQDQIQAF,

SP21
                                   (SEQ ID NO: 19)
KRFAGFFQFVIGVSFHF,

SP22
                                   (SEQ ID NO: 20)
DQVERGNFAKDGSKARVKKSLTKWVKFLKKIIAKLGRPLIGF,

SP24
                                   (SEQ ID NO: 22)
KRFKKFFKKLKNSVRKCAKKFFKKLRVIRVSIPF,

SP25
                                   (SEQ ID NO: 23)
KRFKKFFKKVKKSVKKRLKKIFKKPIVIGVSIPF,

SP26
                                   (SEQ ID NO: 24)
KRFTFYKKVKKNVENLLNKFFKKLRVIGDSIPF,

SP28
                                   (SEQ ID NO: 26)
KRFLRLVVFKKLKKGLRKLFKKKKIVTGHVTS,

SP29
                                   (SEQ ID NO: 27)
KRFKNFFKKIRDGIHEFIHNNRFVIGVNFRF,

SP30
                                   (SEQ ID NO: 28)
KRFKKFFKKIKNGIKTFIKKTQMAIGSHFRW,

SP31
                                   (SEQ ID NO: 29)
KRFKNFFKRVRDGIRDFFRKNHIVIGVNFRF,

SP32
                                   (SEQ ID NO: 30)
KRFLRVFRKLKKGLKKLFKRKKVVTGYVTA,

SP33
                                   (SEQ ID NO: 31)
KRFAGFFQFVVGVSFRF,

SP34
                                   (SEQ ID NO: 32)
KRFVGSFQLVVGVSFRF,
and

SP35
                                   (SEQ ID NO: 33)
KRFKKFLKKLKKSVKKHVKEFFKKPRVIGV;
```

b) comprising at least 60% of consecutive amino acids of a retro-inverso sequence of a); or c) a functional variant of a) or b), wherein the variant:
   has one or more substitutions of an amino acid by a corresponding non-natural amino acid;

has one or more substitutions of an amino acid by a corresponding D-amino acid; and/or has up to 5 amino acid substitutions, preferably wherein the amino acid substitutions are conservative amino acid substitutions, preferably wherein the use in therapy is as an anti-bacterial, antiviral, antifungal, anti-parasitic, anti-biofilm, anti-inflammatory, immune modulating, and/or anticancer agent.

In one aspect provided is the use of an isolated or recombinant peptide having between 20-200 amino acids to inhibit biofilm formation or to degrade biofilms; as an anti-bacterial agent, anti-fungal agent, antiviral agent, anti-parasitic agent, as a diagnostic, crop protectant, disinfectant, preservative, anti-inflammatory agent, immune-modulating agent and/or anticancer agent, wherein the peptide comprises:

a) comprising at least 60% of an amino acid sequence selected from:

```
SP1
                                  (SEQ ID NO: 1)
RKFKKSFKKIRKWVKKATKIAGEVAVEILITKVILGSVGL,

SP2
                                  (SEQ ID NO: 2)
KRVKRFKKFFKKVKKSVKKRLKKIFKKPMVIGVTIPF,

SP3
                                  (SEQ ID NO: 3)
KRFKKFFKKLKNSVKKRVKKFFRKPRVIGVTFPF,

SP5
                                  (SEQ ID NO: 5)
KRFKKFFRKLKKSVKKRAKEFFKKPRVIGVSIPF,

SP6
                                  (SEQ ID NO: 6)
KRFKKFFKKVKKSVKKRLKKIFKKPMVIGVTIPF,

SP7
                                  (SEQ ID NO: 7)
KRFKKFFKKVKKSVKKRLKKIFKKPMVIGVSIPF,

SP8
                                  (SEQ ID NO: 8)
KRFRKFFKRLLKSVRRAVKKFRKKPRLIGLSTLL,

SP9
                                  (SEQ ID NO: 9)
KRFKKFFKKVKKSVKKRLKKIFKKPMVIGVTFPF,

SP12
                                 (SEQ ID NO: 11)
KRFKKFFMKLKKSVKKRVMKFFKKPMVIGVTFPF,

SP14
                                 (SEQ ID NO: 12)
KRFKKFFKKAKKSVKKRLKKFFNKTRVIGVSIPF,

SP15
                                 (SEQ ID NO: 13)
KRFKKFFRKIKKGFRKIFKKTKIFIGGTIPI,

SP16
                                 (SEQ ID NO: 14)
KRFQNFFRELEKKFREFFRVYRITIGATIRF,

SP17
                                 (SEQ ID NO: 15)
KRFKDFFHRIRDGVRDFFRNNHFVCGVNFRF,

SP18
                                 (SEQ ID NO: 16)
KRFKKFFKKIKTGIKKVIKKTKQAIASHFRW,
```

-continued

```
SP19
                                 (SEQ ID NO: 17)
KRFLRVFKKLKRGIRKLFKKKKIVTGPLTS,

SP20
                                 (SEQ ID NO: 18)
AREKSFLQKMKVILQLSSQDQIQAF,

SP21
                                 (SEQ ID NO: 19)
KRFAGFFQFVIGVSFHF,

SP22
                                 (SEQ ID NO: 20)
DQVERGNFAKDGSKARVKKSLTKWVKFLKKIIAKLGRPLIGF,

SP24
                                 (SEQ ID NO: 22)
KRFKKFFKKLKNSVRKCAKKFFKKLRVIRVSIPF,

SP25
                                 (SEQ ID NO: 23)
KRFKKFFKKVKKSVKKRLKKIFKKPIVIGVSIPF,

SP26
                                 (SEQ ID NO: 24)
KRFTFYKKVKKNVENLLNKFFKKLRVIGDSIPF,

SP28
                                 (SEQ ID NO: 26)
KRFLRLVVFKKLKKGLRKLFKKKKIVTGHVTS,

SP29
                                 (SEQ ID NO: 27)
KRFKNFFKKIRDGIHEFIHNNRFVIGVNFRF,

SP30
                                 (SEQ ID NO: 28)
KRFKKFFKKIKNGIKTFIKKTQMAIGSHFRW,

SP31
                                 (SEQ ID NO: 29)
KRFKNFFKRVRDGIRDFFRKNHIVIGVNFRF,

SP32
                                 (SEQ ID NO: 30)
KRFLRVFRKLKKGLKKLFKRKKVVTGYVTA,

SP33
                                 (SEQ ID NO: 31)
KRFAGFFQFVVGVSFRF,

SP34
                                 (SEQ ID NO: 32)
KRFVGSFQLVVGVSFRF,
and

SP35
                                 (SEQ ID NO: 33)
KRFKKFLKKLKKSVKKHVKEFFKKPRVIGV;
```

b) comprising at least 60% of consecutive amino acids of a retro-inverso sequence of a); or c) a functional variant of a) or b) wherein the variant:

has one or more substitutions of an amino acid by a corresponding non-natural amino acid;

has one or more substitutions of an amino acid by a corresponding D-amino acid; and/or has up to 5 amino acid substitutions, preferably wherein the amino acid substitutions are conservative amino acid substitutions; wherein the use does not comprise the treatment of a human or animal body.

DETAILED DESCRIPTION

In the search for antibacterial agents, antimicrobial peptides are considered to be promising candidates. These peptides are an essential component of the defensive system of organisms throughout nature and offer protection against invading pathogens. The peptides are known to act on the cell membrane allowing them to kill micro-organisms like bacteria and fungi rapidly. Therefore, the peptides are effective against bacteria regardless of the susceptibility to current antibiotics and the metabolic activity of the bacteria. This is in contrast to conventional antibiotics in which effectiveness generally depends on metabolic active, multiplying bacteria. In addition, certain anti-microbial peptides are shown to regulate the adaptive and the innate immune system, inflammation and wound healing. Furthermore, certain peptides are shown to have anti-fungal, anti-viral, anti-parasitic and anti-cancer activities.

The sequence and secondary structure of antimicrobial peptides reported in the literature is diverse. However, most peptides are around 15-40 amino acids, cationic and amphipathic. Their interaction with the anionic membrane surfaces of the target microbes leads to permeabilization of the membrane. As a result the membrane integrity is lost, which leads to lysis and death of the bacterial/fungal cells. Various molecular mechanisms are postulated for membrane permeabilization by antimicrobial peptides.

Antimicrobial peptides are part of the innate immune system and combine a broad activity against microorganisms with immunomodulatory capabilities (Bahar et al., 2013; De Latour et al., 2010). Antimicrobial peptides have a positive charge that makes it possible to bind to the negatively charged membrane of bacteria and disrupt the lipid bilayer (Dean et al., 2011). An important family of antimicrobial peptides are the cathelicidins. In humans, only one cathelicidin has been identified (LL-37) that has antibacterial and immunomodulatory effects (Kosciuczuk et al., 2012; Scott et al., 2002). From the novel cathelicidin sequences found in the genomes of seventeen snake species, a total of 35 different snake peptides were synthesized.

Figure 1:
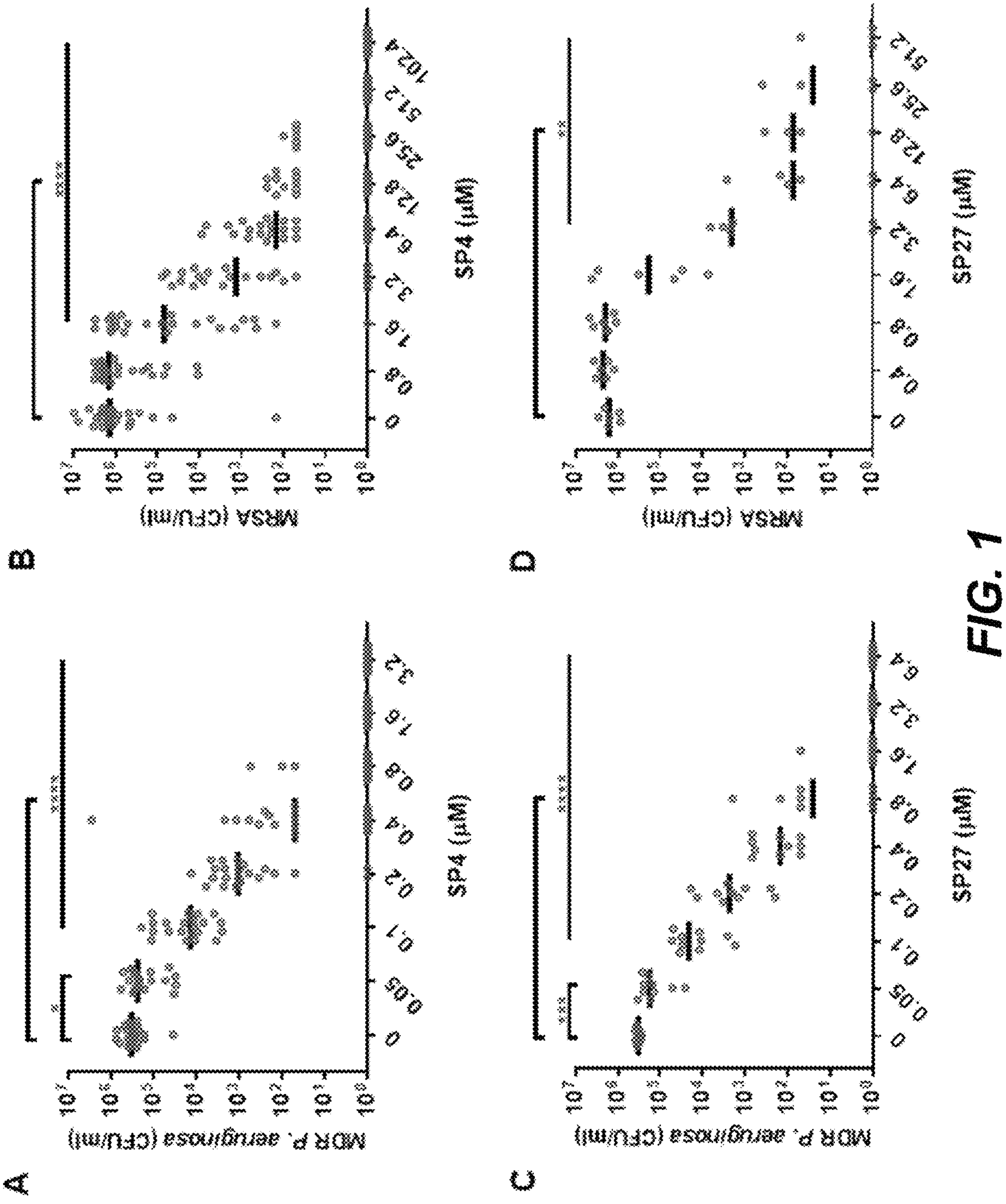
FIG. 1: Dose-dependent killing of multidrug resistant (MDR) *P. aeruginosa* and *S. aureus* by SP4 and SP27. Bactericidal effect of SP4 on MDR *P. aeruginosa* LUH 15103 (Panel A) and MDR *S. aureus* LUH 14616 (Panel B). Bactericidal effect of SP27 on AMR *P. aeruginosa* (Panel C) and MDR *S. aureus* (Panel D). Killing was assessed as the reduction in viable bacteria (CFU/ml) after a 2-hour exposure to increasing peptide concentrations in the presence of 50% v/v human plasma. Significance compared to control (0 μM) was calculated with the Mann-Whitney U test (*P<0.05, P<0.01, *P<0.001 and ****P<0.0001).
Figure 2:
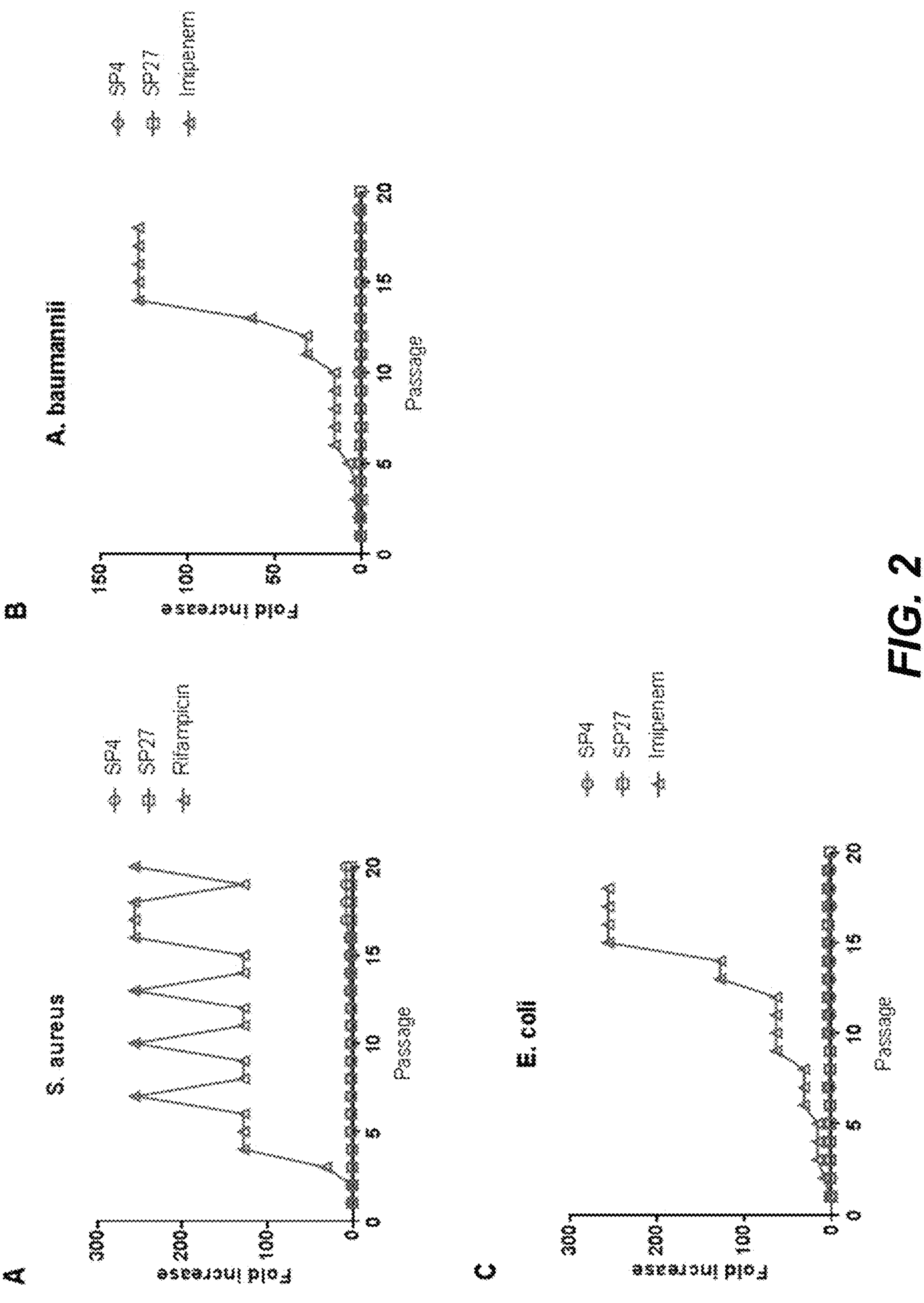
FIG. 2: Resistance development of *S. aureus* (Panel A) and *A. baumannii* (Panel B) against SP4, SP27 and rifampicin. The development of resistance of *S. aureus* LUH 14616 and A. *Baumannii* to SP4 (o), SP27 (□) and rifampicin (Δ) was assessed using 20 passages. The values are the fold increase of the MIC at each passage compared to the MIC at the first passage. (Panel C) Resistance development of *E. coli* against SP4, SP27 and imipenem. The development of resistance of *E. coli* to SP4 (o), SP27 (□) and imipenem (Δ) was assessed using 20 passages. The values are the fold increase of the MIC at each passage compared to the MIC at the first passage.

Provided are novel peptides that exerts high activity against pathogenic microorganisms, but low toxicity in humans. As depicted in FIG. 1, the $LC_{99.9}$ (i.e., the lowest concentration of peptide that kills≥99.9% of the bacteria) for many of the novel peptides is at least 2-3 orders of magnitude lower than the concentration of peptide that begins to demonstrate hemolytic effects. Also provided are peptides that are effective against both gram-negative and gram-positive bacteria. While not wishing to be bound by theory, the peptides disclosed herein also offer the advantage that bacterial resistance to the peptides develops significantly slower than resistance to antibiotics.

Figure 9A:
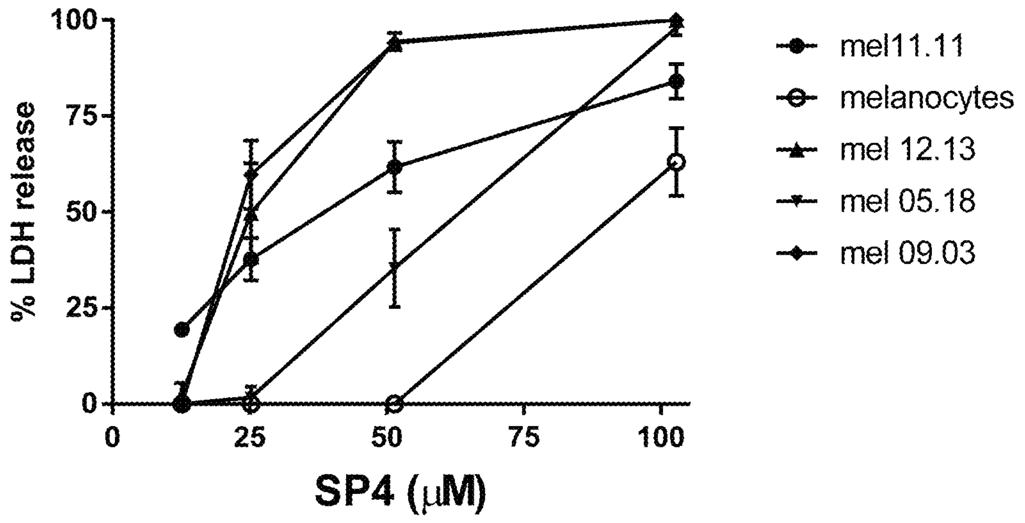
FIGS. 9A and 9B: Selective tumoricidal activity of SP4 and SP27. Briefly, primary human melanocytes and 4 melanoma cell lines were exposed to increasing doses of SP4 (FIG. 9A) and SP27 (FIG. 9B) for 4 hours and then the cell viability was assessed by measuring the LDH release by the cells. Results are expressed as the percentage of LDH release by peptide-exposed cells as compared to triton-exposed cells (=100% LDH release).
Figure 9B:
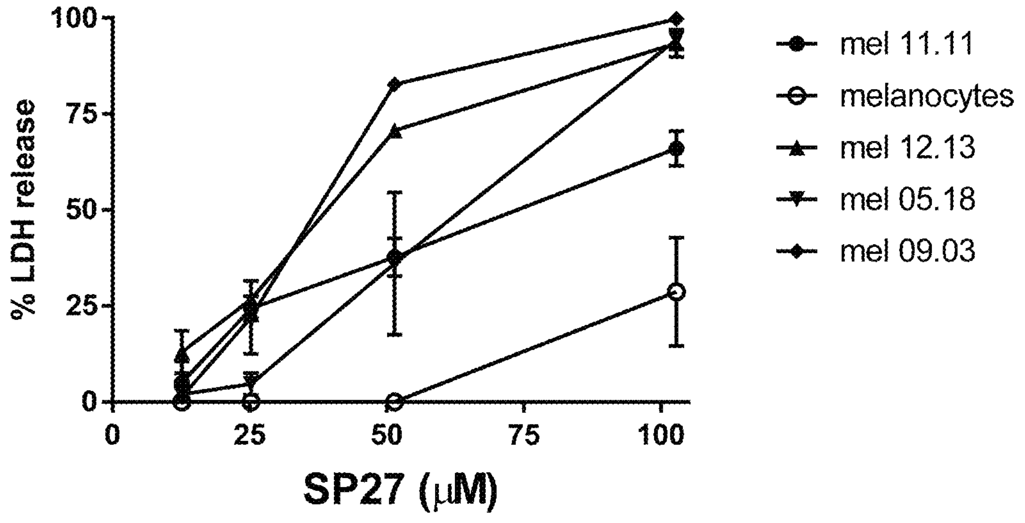

Further provided are novel peptides that selectively kill cancer cells. As depicted in FIGS. 9A and 9B, the novel peptides exert effects on cancer cells at concentrations that have no effect on non-cancerous cells.

In one aspect, the present disclosure provides isolated or recombinant peptides having up to 200 amino acids and comprising an amino acid sequence selected from:

```
SP1
                                    (SEQ ID NO: 1)
RKFKKSFKKIRKWVKKATKIAGEVAVEILITKVILGSVGL,

SP2
                                    (SEQ ID NO: 2)
KRVKRFKKFFKKVKKSVKKRLKKIFKKPMVIGVTIPF,

SP3
                                    (SEQ ID NO: 3)
KRFKKFFKKLKNSVKKRVKKFFRKPRVIGVTFPF,

SP4
                                    (SEQ ID NO: 4)
KRFKKFFKKLKNNVKKRVKKFFRKPRVIGVTIPF,

SP5
                                    (SEQ ID NO: 5)
KRFKKFFRKLKKSVKKRAKEFFKKPRVIGVSIPF,

SP6
                                    (SEQ ID NO: 6)
KRFKKFFKKVKKSVKKRLKKIFKKPMVIGVTIPF,

SP7
                                    (SEQ ID NO: 7)
KRFKKFFKKVKKSVKKRLKKIFKKPMVIGVSIPF,

SP8
                                    (SEQ ID NO: 8)
KRFRKFFKRLLKSVRRAVKKFRKKPRLIGLSTLL,

SP9
                                    (SEQ ID NO: 9)
KRFKKFFKKVKKSVKKRLKKIFKKPMVIGVTFPF,

SP11
                                   (SEQ ID NO: 10)
KRFKKFFRKLKKSVKKRVKKFFKKPRVIGVTIPF,

SP12
                                   (SEQ ID NO: 11)
KRFKKFFMKLKKSVKKRVMKFFKKPMVIGVTFPF,

SP14
                                   (SEQ ID NO: 12)
KRFKKFFKKAKKSVKKRLKKFFNKTRVIGVSIPF,

SP15
                                   (SEQ ID NO: 13)
KRFKKFFRKIKKGFRKIFKKTKIFIGGTIPI,

SP16
                                   (SEQ ID NO: 14)
KRFQNFFRELEKKFREFFRVYRITIGATIRF,

SP17
                                   (SEQ ID NO: 15)
KRFKDFFHRIRDGVRDFFRNNHFVCGVNFRF,

SP18
                                   (SEQ ID NO: 16)
KRFKKFFKKIKTGIKKVIKKTKQAIASHFRW,
```

-continued

```
SP19
                                   (SEQ ID NO: 17)
KRFLRVFKKLKRGIRKLFKKKKIVTGPLTS,

SP20
                                   (SEQ ID NO: 18)
AREKSFLQKMKVILQLSSQDQIQAF,

SP21
                                   (SEQ ID NO: 19)
KRFAGFFQFVIGVSFHF,

SP22
                                   (SEQ ID NO: 20)
DQVERGNFAKDGSKARVKKSLTKWVKFLKKIIAKLGRPLIGF,

SP23
                                   (SEQ ID NO: 21)
KRFKKFFKKIKNSVKKRVKKFFKKPRVIGVSIPF,

SP24
                                   (SEQ ID NO: 22)
KRFKKFFKKLKNSVRKCAKKFFKKLRVIRVSIPF,

SP25
                                   (SEQ ID NO: 23)
KRFKKFFKKVKKSVKKRLKKIFKKPIVIGVSIPF,

SP26
                                   (SEQ ID NO: 24)
KRFTFYKKVKKNVENLLNKFFKKLRVIGDSIPF,

SP27
                                   (SEQ ID NO: 25)
KRFKKFFRKVKKGVHRYFKKNKFYIAATIPYYG,

SP28
                                   (SEQ ID NO: 26)
KRFLRLVVFKKLKKGLRKLFKKKKIVTGHVTS,

SP29
                                   (SEQ ID NO: 27)
KRFKNFFKKIRDGIHEFIHNNRFVIGVNFRF,

SP30
                                   (SEQ ID NO: 28)
KRFKKFFKKIKNGIKTFIKKTQMAIGSHFRW,

SP31
                                   (SEQ ID NO: 29)
KRFKNFFKRVRDGIRDFFRKNHIVIGVNFRF,

SP32
                                   (SEQ ID NO: 30)
KRFLRVFRKLKKGLKKLFKRKKVVTGYVTA,

SP33
                                   (SEQ ID NO: 31)
KRFAGFFQFVVGVSFRF,

SP34
                                   (SEQ ID NO: 32)
KRFVGSFQLVVGVSFRF,
and

SP35
                                   (SEQ ID NO: 33)
KRFKKFLKKLKKSVKKHVKEFFKKPRVIGV.
```

Further provided are peptides having deletions at the N- and/or C-terminus. In a particular embodiment, provided is at least 15, preferably at least 20, or at least 25 consecutive amino acids of an amino acid sequence selected from:

```
(SP27)
                                   (SEQ ID NO: 25)
KRFKKFFRKVKKGVHRYFKKNKFYIAATIPYYG,
```

-continued

```
(SP11)
                                        (SEQ ID NO: 10)
KRFKKFFRKLKKSVKKRVKKFFKKPRVIGVTIPF,

(SP23)
                                        (SEQ ID NO: 21)
KRFKKFFKKIKNSVKKRVKKFFKKPRVIGVSIPF,
and

(SP4)
KRFKKFFKKLKNNVKKRVKKFFRKPRVIGVTIPF.
```

Further provided are peptides having an amino acid sequence that comprises at least 80% of any of the above mentioned sequences. Preferably, such a peptide comprises 80% of a consecutive sequence provided herein. For example, the peptide may lack a limited number of amino acids at the N-terminus and/or C-terminus, as long as 80% of the sequence is present. For example, 80% of SP1 includes 32 of the consecutive amino acids of SP1 (RKFKKSFKKIRKWVKKATKIAGEVAVEILITKVILG-SVGL). This includes a deletion of up to 8 amino acids on the C-terminus or a deletion of up to 8 amino acids on the C-terminus, or a deletion at the N-terminus and deletion on the C-terminus of in total up to 8 amino acids.

Further provided are peptides having an amino acid sequence that comprises at least 60% of any of the above mentioned sequences. Preferably, such a peptide comprises 60% of a consecutive sequence provided herein. For example, the peptide may lack a limited number of amino acids at the N-terminus and/or C-terminus, as long as 60% of the sequence is present. For example, 60% of SP4 includes 21 of the consecutive amino acids of SP4 (KRFKKFFKKLKNNVKKRVKKFFRKPRVIGVTIPF (SEQ ID NO:4)). This includes a deletion of up to 13 amino acids on the C-terminus or a deletion of up to 13 amino acids on the C-terminus, or a deletion at the N-terminus and deletion on the C-terminus of in total up to 13 amino acids. For example, 60% of SP27 includes 20 of the consecutive amino acids of SP27 (KRFKKFFRKVKKGVHRYFK-KNKFYIAATIPYYG (SEQ ID NO:25)). This includes a deletion of up to 13 amino acids on the C-terminus or a deletion of up to 13 amino acids on the C-terminus, or a deletion at the N-terminus and deletion on the C-terminus of in total up to 13 amino acids.

Preferably, the peptide may have a deletion of up to 9 amino acids on the C-terminus or a deletion of up to 9 amino acids on the C-terminus, or a deletion at the N-terminus and deletion on the C-terminus of in total up to 13 amino acids, whereby the deletion at the N-terminus and deletion on the C-terminus are limited to maximum 9 amino acids.

Further provided are peptides having a retro-inverso sequence of the peptides disclosed herein. These "retro-inverso peptides" may similarly have deletions as the N- or C-terminus as disclosed herein. As known to a skilled person, retro-inverso peptides are peptides in which the amino acid sequence is reversed and the alpha-center chirality of the amino acids is inverted. Typically, and in preferred embodiments, a retro-inverso peptide consists of D-amino acids. Retro-inverso peptides may have binding characteristics similar to their L-peptide counterparts.

Further provided are functional variants of the peptides as described herein. The functional variant may have one or more substitutions of an amino acid by a corresponding non-natural amino acid, one or more substitutions of an amino acid by a corresponding D-amino acid, and/or up to 5 amino acid substitutions, preferably wherein the amino acid substitutions are conservative amino acid substitutions.

In one embodiment, one or more natural amino acids of the sequence are substituted by a corresponding non-natural amino acid. As used herein, a "corresponding non-natural amino acid" refers to a non-natural amino acid that is a derivative of the reference natural amino acid. For instance, a natural amino acid is substituted by the corresponding β-amino acid. β-amino acids have their amino group bonded to the β carbon rather than the α carbon as in the natural amino acids. For instance, α-alanine is substituted by β-alanine, etc. Other examples of substitution of a natural amino acid by a non-natural amino acid that is a derivative of the natural amino acid are the following. Alanine is, for instance, substituted by beta-alanine, t-butylalanine, 2-naphthylalanine; L-3-(2-naphthyl)alanine, or 2-aminoisobutyric acid. Arginine is, for instance, substituted by homoarginine, ornithine, N5-carbamoyl ornithine, 3-amino-propionic acid, methylarginine, asymmetric dimethylarginine, shortened arginine, or citrulline. Asparagine is, for instance, substituted by N-ethylasparagine. Aspartic acid is, for instance, substituted by 4-tert-butyl hydrogen 2-azidosuccinate. Cysteine is, for instance, substituted by cysteic acid or homocysteine. Glutamic acid is, for instance, substituted by γ-carboxy-DL-glutamic acid or 4-fluoro-DL-glutamic acid. Glutamine is, for instance, substituted by D-citrulline or thio-L-citrulline. Glycine is, for instance, substituted by N-methylglycine, t-butylglycine, N-methylglycine, or D-allylglycine. Histidine is, for instance, substituted by 3-β-methyl-4-nitrobenzyl)-L-histidine methyl ester, 1-methylhistidine, or 3-methylhistidine. Isoleucine is, for instance, substituted by isodesmosine, N-methylisoleucine, allo-isoleucine, norvaline, homoleucine, norleucine, or 2-aminobutyric acid. Leucine is, for instance, substituted by norleucine, desmosine, or 5,5,5-trifluoro-leucine. Lysine is, for instance, substituted by 6-N-methyllysine, 2-aminoheptanoic acid, N-acetyl lysine, hydroxylysine, allo-hydroxylysine, homolysine, ε-methyl lysine, ε,ε-dimethyl lysine, 6,6,6-trimethyl lysine, ornithine, 2,3-diaminopropanoic acid, or 2,4-diaminobutanoic acid. Methionine is, for instance, substituted by methionine sulfoxide. Phenylalanine is, for instance, substituted by p-amino-L-phenylalanine, 3-benzothienyl alanine p-bromophenylalanine, p-acyl-L-phenylalanine, 2-fluorophenylalanine, 3-fluorophenylalanine, 4-fluorophenylalanine, homophenylalanine, homotyrosine, phenylglycine, 4-fluorophenylalanine, 4-chlorophenylalanine, 4-cyanophenylalanine, 4-nitrophenylalanine, or cyclohexylalanine. Proline is, for instance, substituted by 3-hydroxyproline, 4-hydroxyproline, isonipecotic acid, or thiaproline. Serine is, for instance, substituted by homoserine, isoserine, or 3-phenylserine. Threonine is, for instance, substituted by D-thyroxine or allo-threonine. Tryptophan is, for instance, substituted by 5-hydroxy-tryptophan, 5-methoxy-tryptophan, or 5-fluoro-tryptophan. Tyrosine is, for instance, substituted by O-methyl-L-tyrosine, O-4-allyl-L-tyrosine, 3-chloro-tyrosine, O-methyltyrosine, homotyrosine, homophenylalanine, 4-fluorophenylalanine, 4-chlorophenylalanine, 4-cyanophenylalanine, 4-nitrophenylalanine, or dihydroxyphenylalanine. Valine is, for instance, substituted by norvaline, N-methylvaline, 3-fluoro-valine, homoleucine, norleucine, or 2-aminobutyric acid.

In preferred embodiments, one or more amino acids selected from Lysine (K), Arginine (R), Phenylalanine (F), Valine (V), Histidine (H), Tyrosine (Y), Isoleucine (I), or Proline (P) are substituted by a corresponding non-natural amino acid.

In one embodiment, a variant of an amino acid sequence as defined herein may contain one or more substitutions of an L-amino acid by its corresponding D-amino acid. "Corresponding D-amino acid" as used herein is defined as the D-amino acid counter part of an L-amino acid. For example, the corresponding D-amino acid of alanine (A) is D-alanine (a), the corresponding D-amino acid of arginine (R) is D-arginine (r), the corresponding D-amino acid of asparagine (N) is D-asparagine (n), etc. All L-amino acids of a variant as defined herein may be substituted by their corresponding D-amino acids. Hence, the variant may consist entirely of D-amino acids because activity is retained in polypeptides comprising such amino acid variant. Peptides that contain D-amino acids may have advantages over peptides that contain only L-amino acids. In general, D-amino acid containing peptides are less susceptible to proteolytic degradation and have a longer effective time when used as pharmaceuticals. Retro-inverso peptides or D-amino acids allow the design of peptide based drugs that are bioactive and possess increased bioavailability in addition to being resistant to proteolysis.

In some embodiments, functional variants of the peptides may also have up to 5 amino acid substitutions. Optionally, the functional variants of the peptides may have up to 4 amino acid substitutions. Optionally, the functional variants of the peptides may have up to 3 amino acid substitutions. Optionally, the functional variants of the peptides may have up to 2 amino acid substitutions. Optionally, the functional variants of the peptides may have 1 amino acid substitution.

In preferred embodiments, functional variants of the peptides may also have up to 5 conservative amino acid substitutions. Conservative substitutions are amino acid substitutions that change the given amino acid to a different amino acid with similar biochemical properties. For example, amino acids with a hydrophobic side chain are substituted with another amino acid having a hydrophobic side chain. Amino acids with electrically charged side chains are substituted with another amino acid having an electrically charged side chain, preferably an amino acid with a positively charged side chain is substituted by another amino acid with a positively charged side chain and an amino acid with a negatively charged side chain is substituted by another amino acid with a negatively charged side chain. Amino acids with a polar side chain are substituted with another amino acid having a polar side chain.

In preferred embodiments, functional variants of the peptides may have up to 4 conservative amino acid substitutions, preferably up to 3 conservative amino acid substitutions, preferably up to 2 conservative amino acid substitutions, preferably up to 1 conservative amino acid substitution.

Examples of conservative amino acid substitutions are substitution of one or more amino acids selected from the group of L, I, V or A by another amino acid selected from the group; substitution of one or more amino acids selected from the group of R, K or H by another amino acid selected from the group; substitution of E by Q; substitution of Y or W by F; substitution of one or more amino acids selected from the group of Q, N, A, S or T by another amino acid selected from the group.

The peptides or functional variants as disclosed herein comprise up to 200 amino acids. In some embodiments, the peptide or a functional variant comprises between 25-200 amino acids. In some embodiments, the peptide or a functional variant comprises 25-100 amino acids, preferably between 30-50 amino acids.

The peptides or functional variants as disclosed herein comprise up to 200 amino acids. In some embodiments, the peptide or a functional variant comprises between 15-200 amino acids. In some embodiments, the peptide or a functional variant comprises 15-100 amino acids, preferably between 15-50 amino acids, preferably 15-40 amino acids.

The peptides or functional variants as disclosed herein comprise up to 200 amino acids. In some embodiments, the peptide or a functional variant comprises between 20-200 amino acids. In some embodiments, the peptide or a functional variant comprises 20-100 amino acids, preferably between 20-50 amino acids, preferably 20-40 amino acids.

The peptides or functional variants as disclosed herein comprise up to 200 amino acids. In some embodiments, the peptide or a functional variant comprises between 23-200 amino acids. In some embodiments, the peptide or a functional variant comprises 23-100 amino acids, preferably between 23-50 amino acids, preferably 23-40 amino acids.

The peptides or functional variants as disclosed herein comprise up to 200 amino acids. In some embodiments, the peptide or a functional variant comprises between 24-200 amino acids. In some embodiments, the peptide or a functional variant comprises 24-100 amino acids, preferably between 24-50 amino acids, preferably 24-40 amino acids.

In some embodiments, the peptides as disclosed herein are N-terminally and/or C-terminally modified, or the peptide is in a cyclic confirmation. Such modifications may be useful to increase the stability of the peptides disclosed herein and/or reduce degradation by peptidases and proteases. The modifications may also permit coupling of the peptides to other groups, for example, to other amino acid sequences or other biomolecules. As used herein, "N-terminally and/or C-terminally modified" includes a modified amino group or carboxy group. Examples of N-terminal modifications include acetylated, formylated, or guanylated N-termini and examples of C-terminal modifications are amidated C-termini. Additional modifications include acetylation, amidation, formylation, or guanylation. The peptides disclosed herein may also be conjugated to a non-peptide moiety at the N- or C-terminus to form a peptide conjugate. Suitable non-peptide moieties include, e.g., polymers (e.g., PEG), oligosaccharides, lipids, small molecule drugs, etc.

In some embodiments, the peptides as disclosed herein are N-terminally and/or C-terminally modified with a polymer chain, polysaccharide and/or lipid. In preferred embodiments, the peptides are N-terminally and/or C-terminally modified with Polyethylene glycol (PEG) and/or PEGylated. Examples of PEG polymer chains include PEG2, PEGS, PEGS, PEG11, and PEG27. Such modification may be useful to increase the stability of the peptides disclosed herein and/or reduce degradation by peptidases and proteases. The covalent attachment of PEG to a peptide may "mask" the agent from the host's immune system and potentially reducing immunogenicity. Modification with PEG may also increase its hydrodynamic size, which may prolong the circulatory time by reducing renal clearance. Modification with PEG may also provide water solubility to the peptides.

It is clear to a skilled person that the peptides disclosed herein also include the salts of such peptides, in particular, a "pharmaceutically acceptable salt" such as acid addition salts and base addition salts. As used herein, a "pharmaceutically acceptable salt" refers to a salt that retains the desired activity and is suitable for administration to humans or animals. Methods for the preparation of salts of peptides are known in the art and generally involve mixing of the peptide with a pharmaceutically acceptable acid or based, for instance, by reacting the free acid or free base forms of the product with one or more equivalents of the appropriate acid or base in a solvent or medium in which the salt is insoluble, or in a solvent such as water, which is then removed in vacuo or by freeze-drying, or by exchanging the cations of an existing salt for another cation on a suitable ion exchange resin. Examples of pharmaceutically acceptable acids and bases include organic and inorganic acids such as formic acid, acetic acid, propionic acid, lactic acid, glycolic acid, oxalic acid, pyruvic acid, succinic acid, maleic acid, malonic acid, trifluoroacetic acid, cinnamic acid, sulfuric acid, hydrochloric acid, hydrobromic acid, nitric acid, perchloric acid, phosphoric acid, and thiocyanic acid, which form ammonium salts with free amino groups of polypeptides, and bases, which form carboxylate salts with free carboxylic groups of polypeptides, such as ethylamine, methylamine, dimethylamine, triethylamine, isopropylamine, diisopropylamine, and other mono-, di- and trialkylamines, and arylamines.

A preferred isolated or recombinant peptide of the disclosure has between 15-200 amino acids comprising at least 15 consecutive amino acids of an amino acid sequence selected from: KRFKKFFRKVKKGVHRYFKKNKFYIAATIPYYG (SP27) (SEQ ID NO:25), KRFKKFFRKLKKSVKKRVKKFFKKPRVIGVTIPF (SP11) (SEQ ID NO:10), and KRFKKFFKKIKNSVKKRVKKFFKKPRVIGVSIPF (SP23) (SEQ ID NO:21). In some embodiments, the peptide comprises at least 15 consecutive amino acids of a retro-inverso sequence of the sequences or is a functional variant of the peptides.

A preferred isolated or recombinant peptide of the disclosure has between 20-200 amino acids comprising at least 20 consecutive amino acids of an amino acid sequence selected from: KRFKKFFRKVKKGVHRYFKKNKFYIAATIPYYG (SP27) (SEQ ID NO:25), KRFKKFFRKLKKSVKKRVKKFFKKPRVIGVTIPF (SP11) (SEQ ID NO:10), and KRFKKFFKKIKNSVKKRVKKFFKKPRVIGVSIPF (SP23) (SEQ ID NO:21). In some embodiments, the peptide comprises at least 20 consecutive amino acids of a retro-inverso sequence of the sequences or is a functional variant of the peptides.

A preferred isolated or recombinant peptide of the disclosure has between 24-200 amino acids comprising at least 24 consecutive amino acids of an amino acid sequence selected from: KRFKKFFRKVKKGVHRYFKKNKFYIAATIPYYG (SP27) (SEQ ID NO:25), KRFKKFFRKLKKSVKKRVKKFFKKPRVIGVTIPF (SP11) (SEQ ID NO:10), and KRFKKFFKKIKNSVKKRVKKFFKKPRVIGVSIPF (SP23) (SEQ ID NO:21). In some embodiments, the peptide comprises at least 24 consecutive amino acids of a retro-inverso sequence of the sequences or is a functional variant of the peptides.

A preferred isolated or recombinant peptide of the disclosure has between 25-200 amino acids comprising at least 25 consecutive amino acids of an amino acid sequence selected from: KRFKKFFRKVKKGVHRYFKKNKFYIAATIPYYG (SP27) (SEQ ID NO:25), KRFKKFFRKLKKSVKKRVKKFFKKPRVIGVTIPF (S P11) (SEQ ID NO:10), and KRFKKFFKKIKNSVKKRVKKFFKKPRVIGVSIPF (SP23) (SEQ ID NO:21). In some embodiments, the peptide comprises at least 25 consecutive amino acids of a retro-inverso sequence of the sequences or is a functional variant of the peptides.

A preferred isolated or recombinant peptide of the disclosure has between 15-200 amino acids comprising at least 15 consecutive amino acids of the amino acid sequence KRFKKFFKKLKNNVKKRVKKFFRKPRVIGVTIPF (SP4) (SEQ ID NO:4). In some embodiments, the peptide comprises at least 15 consecutive amino acids of a retro-inverso sequence of the sequence or is a functional variant of the peptides.

Preferably, the isolated or recombinant peptide of the disclosure has between 20-200 amino acids comprises at least 20 consecutive amino acids of the amino acid sequence KRFKKFFKKLKNNVKKRVKKFFRKPRVIGVTIPF (SP4) (SEQ ID NO:4). In some embodiments, the peptide comprises at least 20 consecutive amino acids of a retro-inverso sequence of the sequence or is a functional variant of the peptides.

Preferably, the isolated or recombinant peptide of the disclosure has between 24-200 amino acids comprises at least 24 consecutive amino acids of the amino acid sequence KRFKKFFKKLKNNVKKRVKKFFRKPRVIGVTIPF (SP4) (SEQ ID NO:4). In some embodiments, the peptide comprises at least 24 consecutive amino acids of a retro-inverso sequence of the sequence or is a functional variant of the peptides.

A preferred isolated or recombinant peptide of the disclosure has between 25-200 amino acids comprising at least 25 consecutive amino acids of the amino acid sequence KRFKKFFKKLKNNVKKRVKKFFRKPRVIGVTIPF (SP4) (SEQ ID NO:4). In some embodiments, the peptide comprises at least 25 consecutive amino acids of a retro-inverso sequence of the sequence or is a functional variant of the peptides.

A preferred isolated or recombinant peptide of the disclosure comprises:

a) at least an amino acid sequence VKKGVHRYFKKNKFY (SEQ ID NO:34), b) the retro-inverso sequence of a); or c) a functional variant of a) or b), wherein the variant has up to 5 substitutions, preferably up to 4 substitutions, preferably up to 3 substitutions, preferably up to 2 substitutions, preferably up to 1 substitution, selected from:

substitutions of an amino acid by a corresponding non-natural amino acid;

substitutions of an amino acid by a corresponding D-amino acid; and/or amino acid substitutions, preferably wherein the amino acid substitutions are conservative amino acid substitutions.

Preferably, the isolated or recombinant peptide comprises at least an amino acid sequence KVKKGVHRYFKKNKFY (SEQ ID NO:35), preferably RKVKKGVHRYFKKNKFY (SEQ ID NO:36); preferably FRKVKKGVHRYFKKNKFY (SEQ ID NO:37), preferably FFRKVKKGVHRYFKKNKFY (SEQ ID NO:38), preferably KFFRKVKKGVHRYFKKNKFY(SEQ ID NO:39), preferably KKFFRKVKKGVHRYFKKNKFY (SEQ ID NO:40), preferably FKKFFRKVKKGVHRYFKKNKFY (SEQ ID NO:41), preferably RFKKFFRKVKKGVHRYFKKNKFY(SEQ ID NO:42), preferably KRFKKFFRKVKKGVHRYFKKNKFY (SEQ ID NO:43).

Preferably, the peptide may in total may have up to 5 amino acid substitutions. For example, the peptide may have up to 2 amino acid substitutions in the amino acid sequence VKKGVHRYFKKNKFY (SEQ ID NO:34) and an additional 3 amino acid substitutions in the rest of the SP27 sequence (KRFKKFFRKVKKGVHRYFKKNKFYIAATIPYYG (SEQ ID NO:25)).

Preferred peptides comprise
a) an amino acid sequence selected from:

| | |
|---|---|
| SP27-63 | K R F K K F F R K V K K G V H R Y F K K N K F Y |
| SP27-64 | R F K K F F R K V K K G V H R Y F K K N K F Y I |
| SP27-65 | F K K F F R K V K K G V H R Y F K K N K F Y I A |
| SP27-66 | K K F F R K V K K G V H R Y F K K N K F Y I A A |
| SP27-67 | K F F R K V K K G V H R Y F K K N K F Y I A A T |
| SP27-68 | F F R K V K K G V H R Y F K K N K F Y I A A T I |
| SP27-69 | F R K V K K G V H R Y F K K N K F Y I A A T I P |
| SP27-70 | R K V K K G V H R Y F K K N K F Y I A A T I P Y |
| SP27-71 | K V K K G V H R Y F K K N K F Y I A A T I P Y Y |
| SP27-72 | V K K G V H R Y F K K N K F Y I A A T I P Y Y G |
| SP27-114 | K F F R K V K K G V H R Y F K K N K F Y |
| SP27-115 | V K K G V H R Y F K K N K F Y |

(see, SEQ ID NO: 97 and SEQ ID NO: 44-54, respectively);

b) a retro-inverso sequence of a); or
c) a functional variant of a) or b), wherein the variant:
 has one or more substitutions of an amino acid by a corresponding non-natural amino acid;
 has one or more substitutions of an amino acid by a corresponding D-amino acid; and/or
 has up to 5 amino acid substitutions, preferably wherein the amino acid substitutions are conservative amino acid substitutions.

The peptides and functional variants disclosed herein are useful for a number of applications including to inhibit biofilm formation or to degrade biofilms; as an anti-bacterial agent, anti-fungal agent, anti-viral agent, anti-parasitic agent, as a diagnostic, crop protectant, disinfectant, preservative anti-inflammatory agent, immune-modulating agent and/or anti-cancer agent as well as a therapeutic for the treatment of a bacterial, fungal, viral and/or parasitic infection, an inflammatory condition, or a cancer; or in the treatment of a condition resulting from bacterial, fungal, viral and/or parasitic infection, biofilm formation, an inflammatory condition, or a cancer. The peptides and functional variants disclosed herein preferably have bactericidal activity and in particular bactericidal activity on MDR *S. aureus* and/or MDR *P. aeruginosa*, preferably with low toxicity against human erythrocytes. Preferably, the peptide and functional variants disclosed herein have anti-bacterial, anti-viral, anti-fungal, anti-parasitic, anti-inflammatory and/or anti-cancer-activity.

The peptides as disclosed herein may be produced synthetically. For example, a peptide may be synthesized by commonly used solid-phase synthesis methods, e.g., methods that involve t-BOC or FMOC protection of alpha-amino groups, which are well known in the art. The peptides may also be produced using recombinant technology. Accordingly, Further provided are nucleic acid molecules encoding the peptides. A nucleic acid as used in the disclosure is typically, but not exclusively, a ribonucleic acid (RNA) or a deoxyribonucleic acid (DNA). Based on the genetic code, a skilled person may determine the nucleic acid sequence that encodes the antibody variants disclosed herein. Based on the degeneracy of the genetic code, sixty-four codons may be used to encode twenty amino acids and translational terminal signal. As is known to a skilled person, codon usage bias in different organisms may effect gene expression level. Various computational tools are available to the skilled person in order to optimize codon usage depending on which organisms the desired nucleic acid will be expressed.

Further provided are a vector comprising a nucleic acid sequence molecule according to this disclosure. The term "vector" as used herein refers to a nucleic acid molecule, such as a plasmid, bacteriophage or virus, capable of introducing a heterologous nucleic acid sequence into a host cell. A vector according to the disclosure allows the expression or production of a peptide encoded by the heterologous nucleic acid sequence in a host cell. It is within the purview of a skilled person to prepare suitable expression vectors for expressing the peptides disclosed herein. Suitable regulatory sequences including enhancers, promoters, translation initiation signals, and polyadenylation signals may be included. Additionally, depending on the host cell chosen and the vector employed, other sequences, such as an origin of replication, additional DNA restriction sites, enhancers, and sequences conferring inducibility of transcription may be incorporated into the expression vector. The expression vectors may also contain a selectable marker gene that facilitates the selection of host cells transformed or transfected. Examples of selectable marker genes are genes encoding a protein such as G418 and hygromycin that confer resistance to certain drugs, β-galactosidase, chloramphenicol acetyltransferase, and firefly luciferase.

When the nucleic acid is expressed in a cell, the cell produces a peptide according to the disclosure. Therefore, in one embodiment, a cell is provided comprising a nucleic acid or vector according to the disclosure. The host cells may be a mammalian, insect, plant, bacterial, or yeast cell. The disclosure further encompasses cell cultures that comprise the cells.

Further provided are methods for transforming a host cell with a nucleic acid or vector as disclosed herein. "Transformation" refers to the introduction of a foreign nucleic acid into a recipient cell. Transformation of a host cell may result in transient expression of a recombinant protein by the cell, meaning that the recombinant protein is only expressed for a defined period of time. Alternatively, transformation of a recipient cell may result in stable expression, meaning that the nucleic acid is introduced into the genome of the cell and thus passed on to next generations of cells. Additionally, inducible expression of a recombinant protein may be achieved. An inducible expression system requires the presence or absence of a molecule that allows for expression of a nucleic acid sequence encoding a polypeptide of this disclosure. Examples of inducible expression systems include, but are not limited to, Tet-On and Tet-Off expression systems, hormone inducible gene expression system such as, for instance, an ecdysone inducible gene expression system, an arabinose-inducible gene expression system, and a *Drosophila* inducible expression system using a pMT/BiP vector (Invitrogen) that comprises an inducible metallothioneine promoter.

Further provided are methods for producing the peptides of the disclosure comprising transforming a host cell with a vector as disclosed herein. Examples of suitable host cells include plant cells such as corn cells, rice cells, duckweed cells, tobacco cells (such as BY-2 or NT-1 cells), and potato cells. Examples of yeast cells are *Saccharomyces* and *Pichia*. Examples of insect cells are *Spodoptera frugiperda* cells, such as Tn5, SF-9 and SF-21 cells, and *Drosophila* cells, such as *Drosophila* Schneider 2 (S2) cells. Examples of mammalian cells that are suitable for expressing a peptide as disclosed include African Green Monkey kidney (Vero) cells, baby hamster kidney (such as BHK-21) cells, Human retina cells (for example, PER.C6 cells), human embryonic kidney cells (such as HEK293 cells), Madin-Darby Canine Kidney (MDCK) cells, Chicken embryo fibroblasts (CEF), Chicken embryo kidney cells (CEK cells), blastoderm-derived embryonic stem cells (e.g., EB14), mouse embryonic fibroblasts (such as 3T3 cells), Chinese hamster ovary (CHO) cells, and derivatives of these cell types.

In some embodiments, the methods for producing the peptides of the disclosure further comprise a step of harvesting, purifying and/or isolating the peptides. Methods for peptide purification are known to a skilled person and include, e.g., gel electrophoresis or chromatography methods.

In some embodiments, provided is a method for the preparation of a peptide as disclosed herein comprising:

- providing a nucleic acid molecule comprising a nucleic acid sequence encoding the peptide;
- transforming a host cell with the nucleic acid molecule;
- culturing the host cell under conditions that allow expression of the peptide;
- harvesting the peptide from the cells; and
- optionally, N-terminally or C-terminally modifying the peptide.

As disclosed further herein, the peptides of the disclosure exhibit a number of activities that may be advantageously used in both therapeutic and nontherapeutic applications. As such, Further provided are compositions comprising one or more peptides as disclosed herein that are suitable for such uses. In one embodiment, the compositions are useful as a medicament for use in an individual. An individual refers to a human or animal, preferably wherein the animal is a vertebrate, in particular a mammal or bird. An individual, as used herein, may also refer to other organisms, for example, a plant. Accordingly, provided is compositions comprising one or more peptides as disclosed herein together with at least one pharmaceutically acceptable carrier, diluent and/or excipient. As used herein, the term "pharmaceutically acceptable" refers to those compositions or combinations of agents, materials, or compositions, and/or their dosage forms, that are within the scope of sound medical judgment, suitable for use in contact with the tissues of human beings and animals without excessive toxicity, irritation, allergic response, or other problem or complication, commensurate with a reasonable benefit/risk ratio. Furthermore, the term "pharmaceutically acceptable diluent or carrier" refers to a pharmaceutically acceptable material, composition or vehicle, such as a liquid or solid filler, diluent, excipient, solvent or encapsulating material, involved in carrying or transporting the peptide from one organ, or portion of the body, to another organ, or portion of the body.

The pharmaceutical composition may be administered by any suitable route and mode. As will be appreciated by the person skilled in the art, the route and/or mode of administration will vary depending upon the desired results. The pharmaceutical compositions may be formulated in accordance with routine procedures for administration by any routes, such as parenteral, topical (including ocular), oral, sublingual, transdermal, or by inhalation. Parenteral administration includes, e.g., intravenous, intramuscular, intraarterial, intracoronary, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The compositions may be in any suitable forms, such as liquid, semi-solid and solid dosage forms. The compositions may be in the form of tablets, capsules, powders, granules, lozenges, creams or liquid preparations (in particular for administration to the skin or eye), such as sterile parenteral solutions or suspensions or in the form of a spray, aerosol or other conventional method for inhalation. The pharmaceutical compositions of the present disclosure include those suitable for oral, nasal, topical (including buccal and sublingual), rectal, vaginal and/or parenteral administration. In particular embodiments, the composition is a topical composition in the form of a cream, gel, ointment, lotion, foam, suspension, spray, aerosol, or powder aerosol. The compositions are particularly useful for administration to the skin.

The peptides may be formulated in the compositions for controlled release and/or targeted delivery carrier. As used herein, the term "controlled release" refers to the release of the peptide in a time-dependent manner. In one embodiment, controlled release refers to slow release. As used herein, the term "targeted delivery" refers to the release of the peptide in a site-directed manner. Preferably, a peptide is targeted to a site infected by bacteria, fungi, viruses and/or parasites or to the cancer. Controlled release and/or targeted delivery carriers are well known in the art. Non limiting examples of controlled release and/or targeted delivery vehicles are nanoparticles, microparticles, nanocapsules, microcapsules, liposomes, microspheres, hydrogels, polymers, lipid complexes, serum albumin, antibodies, cyclodextrins and dextrans. Targeted delivery is, for instance, achieved by providing a carrier with targeting groups on the surface thereof. Examples of such carrier comprising targeting groups are antibody-functionalized carriers, carriers having a site-specific ligand and carriers having a positive or negative surface charge. Preferred particles for controlled release and/or targeted delivery are nanoparticles, i.e., particles in the range of about 1 to 500 nm in diameter, preferably up to about 200 nm in diameter, and liposomes, optionally provided with targeting groups.

Actual dosage levels of the pharmaceutical compositions may be varied so as to obtain an amount of peptide that is effective ("effective amount") to achieve the desired therapeutic response for a particular patient, composition, and mode of administration, without being toxic to the patient.

The selected dosage level will depend upon a variety of pharmacokinetic factors including the activity of the peptide, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts. The dosage and scheduling for the formulation that is selected may be determined by standard procedures well known by a skilled person. Such procedures involve extrapolating and estimating dosing schedule from animal models, and then determining the optimal dosage in a human clinical dose ranging study. The dosage in pharmaceutical compositions will vary depending upon a number of factors, such as the desired release and pharmacodynamic characteristics. Typical doses of administration of the peptide are between 0.01 and 100 mg per kg body weight. As disclosed further herein, the peptide compositions may be used in the treatment of humans, animals, and crop plants.

Further provided are oral care products comprising a peptide as disclosed herein. Suitable oral care compositions include, e.g., toothpaste, dentifrice, tooth powder, tooth gel, subgingival gel, mouthrinse/mouthwash, artificial saliva, denture product, mouthspray, lozenge, oral tablet, and chewing gum.

The peptides are useful as disinfectants and may be used in cleaning compositions together with, or as alternatives to, other disinfectants commonly used in the art. Cleaning products include, e.g., surface cleaning compositions (for example, glass, floor, counter, bath, toilet bowl, sink, appliance and furniture cleaning compositions); deodorants (for example, solid, liquid and spray deodorants air and/or surface deodorants); disinfectants (for example, spray and solid air or surface disinfectants; waxes and other surface protecting and/or polishing compositions; laundry compositions (for example, detergents, fabric softeners and whiteners); and rug shampoo. Such cleaning compositions may further include detergents, enzymes (e.g., proteases), ethanol, propanol, propylene glycol, isopropanol, or other alcohols. The cleaning composition may be provided as a solution, including a concentrate that should be diluted prior to use, as well as in the form of wipes impregnated with the cleaning composition.

Further provided are method for disinfecting a surface or composition, the method comprising contacting the surface or composition or providing the surface or composition with the isolated or recombinant peptide and/or the composition as disclosed herein. Suitable surfaces and compositions are disclosed herein. For example, in an exemplary embodiment, a surface (e.g., a hospital floor or sink, dental unit water system) is contacted with a cleaning composition comprising one or more peptides of the disclosure.

The peptides are also useful as preservatives and may be used in compositions together with, or as alternatives to, other preservatives commonly used in the art. In some embodiments, the composition is a cosmetic product, e.g., a cosmetic cream, gel, lotion, shampoo, conditioner, body rinse, body lotion, color agent, skin color agent, eye color agent, or perfume. In some embodiments, the composition is an ophthalmic composition suitable for administration to the eye. Preferred ophthalmic compositions include contact lens solution, eyewash, eye drops, and eye gel.

In some embodiments, the composition is a food product. Pathogenic microorganisms in foods may cause infections or intoxication of subjects or change the look, consistency, flavor and/or odor of food products. The peptides of the disclosure may be applied directly to a food product (such as spraying or washing), mixed directly into a food product (e.g., added to a sauce or dairy product), or applied to the food packaging (e.g., a plastic container). Suitable food products include, e.g., vegetables, fruit, meat products, bakery products (baked goods) and dairy products.

Further provided are articles coated with the peptides disclosed herein. Suitable articles include cleaning products such as wipes and cloths that have been impregnated with the peptides. Suitable articles also include medical devices and surgical equipment, or articles for storing the devices and equipment or articles that come into contact with the devices and equipment. Medical devices include, e.g., wound or tissue dressings, prosthetics (hip implants, dental implants, prosthetic joint, a voice prosthetic, a penile prosthetic), stents (e.g., biliary, urethral, ureteral, tracheal, coronary, gastrointestinal and esophageal stents), a mechanical heart valve, a cardiac pacemaker, an arteriovenous shunt, a schleral buckle, catheters (e.g., central venous catheter, an intravascular catheter, an urinary catheter, a Hickman catheter, a peritoneal dialysis catheter, an endrotracheal catheter), tympanostomy tube, a tracheostomy tube, a surgical suture, a bone anchor, a bone screw, an intraocular lens, a contact lens, an intrauterine device, an aortofemoral graft, or a vascular graft. Surgical instruments include, e.g., clamp, forceps, scissor, skin hook, tubing, needle, retractor, scaler, drill, chisel, rasp, or saw. Suitable articles also include articles that come in contact with or store such medical devices or surgical equipment, e.g., a contact lens case.

In some embodiments, the article is coated with a peptide as disclosed herein, in particular wherein the coating allows for the slow release of the peptide. In particular, the coating is biodegradable and comprises a material selected from the group consisting of PLA (poly lactic acid), PGA (poly glycolic acid), polycaprolactone (PCA), polyethylene oxide (PEO), polydioxanone (PDS), polycaprolactone (PCL), polypropylene fumarate, polymers derived from lactones, such as lactide, glycolide and caprolactone, carbonates such as trimethylene carbonate and tetramethylene carbonate, dioxanones, ethylene glycol, polyester amide (PEA) ethylene oxide, esteramides, γ-hydroxyvalerate, β-hydroxypropionate, α-hydroxy acid, hydroxybuterates, hydroxy alkanoates, polyimide carbonates, polyurethanes, polyanhydrides, and combinations thereof, polysaccharides such as hyaluronic acid, chitosan and cellulose, and proteins such as gelatin and collagen.

The peptides and compositions disclosed herein are useful for treating and/or preventing various disorders and conditions. In some embodiments, the peptides and compositions disclosed herein are useful for treating and/or preventing bacterial infection, particularly in a human, animal and plants. As used herein, “treating and/or preventing bacterial infection” refers to delaying, inhibiting or preventing a bacterial infection as well as delaying, inhibiting, preventing, or reducing the severity of one or more symptoms of a bacterial infection. Examples of pathogenic bacteria that may cause infections in humans or animals that are treatable with the peptides disclosed herein include acinetobacters, listeriae, escherichiae, chlamydiae, rickettsial bacteria, *mycoplasma*’s, mycobacteria, staphylococci, streptococci, pneumonococci, meningococci, *klebsiella*, pseudomonae, legionellae, diphtheria, salmonellae, bacilli, *Vibrio cholerae*, tetanus, clostridiae, bacilli, yersiniae, and Leptospira bacteria. Preferably, the bacteria are gram-negative bacteria. Accordingly, provided is the use of the peptides as disclosed herein for treating, including prophylactic treatment, of a human or animal. The peptides, nucleic acids, vectors, or compositions comprising same, may be administered to an individual in need thereof by any means known to a skilled person and may be administered to an individual at risk of developing a bacterial infection or to an individual after a bacterial infection has been diagnosed.

The peptides and compositions disclosed herein are also useful for ex vivo applications, e.g., as anti-bacterial agents. Method are disclosed herein for inhibiting bacteria on a surface or in a composition comprising providing the surface or composition with a peptide as disclosed herein. As used herein, "inhibiting bacteria" refers to impairing, inhibiting or slowing bacterial growth as well as promoting bacteria death.

As used herein, a "surface" refers to any hard or soft surface, such as those found in household environments, in industrial environments, and surfaces of food products such as fruits, vegetables and meat. A surface includes glass, metal, porous, and non-porous surfaces. It also pertains to exterior and interior surfaces of equipment that may be contaminated, such as those found in the food industry or the medical equipment found in hospitals and health care facilities, as well as plumbing systems (e.g., sink drain), countertops, building materials, ductwork, and clean rooms. A surface also refers to the surface of a medical or surgical device. A surface also refers to the interior or exterior of pipes, for example, drains. A surface also includes the surfaces of plants (e.g., leaves, roots, seeds, etc.). In some embodiments, a surface refers to an exterior or interior surface of a human or animal body (e.g., mucosal membrane, oral cavity). In some embodiments, the surface is not an in vivo surface (or rather is not a surface of a human or animal body). Treatment of the surface is accomplished by any means known to those of ordinary skill in the art including, but not limited to, dipping, soaking, brushing, spraying, mopping, washing, or the like. The length of treatment required will vary according to treatment conditions, the selection of which is known to those skilled in the art.

As used herein, a "composition" may be liquid, solid, or semi-solid and may include one or more compounds or materials. Suitable compositions include those already described, e.g., medicaments/pharmaceutical preparations, oral care compositions, cleaning compositions, food products, cosmetic products, and ophthalmic compositions.

In some embodiments, the peptides are useful for inhibiting, inhibiting, and/or reducing antibiotic resistant bacteria. As used herein, "antibiotic-resistant bacteria" refers to bacteria that have acquired an inherited mutation/alteration allowing them to grow at higher concentrations of an antibiotic irrespective of the duration of treatment. This may be quantified by the minimum inhibitory concentration (MIC) of a particular antibiotic. MIC refers to the lowest concentration of an antibiotic that prevents the visible growth of a bacterium. In a preferred embodiment, the antibiotic resistant bacteria is selected from *Enterococcus faecium, Staphylococcus aureus, Klebsiella pneumoniae, Acinetobacter baumannii, Pseudomonas aeruginosa*, and *Enterobacter* species.

In some embodiments, the peptides are useful for inhibiting antibiotic tolerant bacteria. See, Brauner et al., *Nature* 2016, 14:321-330, for a review on antibiotic tolerance. As used herein, antibiotic tolerance refers to the ability of a micro-organism to survive transient exposure to high doses of an antibiotic for long periods. In contrast to antibiotic resistance, the MIC of a particular antibiotic does not change in case of an antibiotic tolerant bacterium. Tolerance may be inheritable or non-inheritable and is generally associated with the slowed growth or dormancy.

In some embodiments, the peptides are useful for inhibiting bacterial persisters. See, Brauner et al., *Nature* 2016, 14:321-330, for a review on persistence. As used herein, antibiotic persistence refer to the ability of a sub-population of bacteria to survive antibiotic treatment. Persistence may be detected by a bimodal time-kill curve, demonstrating the presence of at least two coexisting subpopulations of bacteria. Generally, bacterial persisters have a slower growth rate than the majority of the bacterial population or they have a transient decrease in antibiotic sensitivity, e.g., by the overexpression of a resistance factor.

In some embodiments, the peptides are useful for inhibiting biofilm formation or for removing or reducing a biofilm. As used herein, inhibiting biofilm formation refers to a reduction or prevention in the amount of biofilm formed as compared to the amount of biofilm that would have formed in the absence of treatment with the peptides. Such a reduction may be due to a decrease in microbial growth, an increase in microbial killing, degradation of the extracellular matrix, reduced production of matrix and/or a modulation in the ability of a microbe to attach to a surface. Similarly, removing or reducing a biofilm may include a decrease in microbial growth, an increase in microbial killing, degradation of the extracellular matrix, reduced production of matrix and/or a modulation in the ability of a microbe to attach/detach to a surface (in particular, detachment from a surface may be promoted). Further provided are methods for inhibiting biofilm formation on a surface (as disclosed herein) and/or degrading the biofilm from a surface, the method comprising contacting the surface with the isolated or recombinant peptide and/or the composition as disclosed herein.

As used herein, microbial biofilms develop when micro-organisms adhere to a surface and produce extracellular polymers that facilitate adhesion and provide a structural matrix. The extracellular matrix comprises exopolysaccharides, proteins and nucleic acids. Biofilms may form on living or non-living surfaces and are found in natural, industrial and hospital settings. Biofilms may contain many different types of micro-organisms, e.g., bacteria, archaea, protozoa, fungi and algae.

Biofilms may negatively impact human and animal health. Biofilms have been found to be involved in a wide variety of clinical infections in the body, by one estimates 80% of all infections. For example, biofilms are involved in bacterial vaginosis, urinary tract infections, catheter infections, middle ear infections, gingivitis, coating contact lenses. Examples of lethal infections whereby biofilms are involved are, endocarditis, infections in cystic fibrosis, infections of permanent implants such as joint prosthesis, heart valves and intervertebral disc indwelling devises, e.g., catheters, intravenous lines etc. Bacterial biofilms may delay cutaneous wound healing and reduce topical antibacterial efficiency of conventional antibiotics in healing or treating infected skin wounds, skin infections or urinary tract infections. In addition, biofilms may form on teeth of animals or humans as dental plaque. These biofilms contribute to tooth decay and gum disease. Biofilm formation may also occur along the gastrointestinal tract. A "healthy" biofilm of the gastrointestinal tract is beneficial and has lubricating and anti-inflammatory properties. However, a disruption in the normal biofilm of the intestine may lead to an "unhealthy" biofilm that is associated with bloating, stomach cramps, inflammatory bowel disease, ulcerative colitis, and Crohn's Disease (see, e.g., Von Rosenvinge et al., Pathog. Dis. 2013;

67(1): 25-38). *Helicobacter pylori* biofilms, for example, are associated with peptic ulcer disease.

Implantable or insertable medical devices are frequently susceptible to bacterial infection and/or biofilm formation. This is particularly relevant for devices that are adapted for long-term use, e.g., longer than a few days or weeks. Microbes often colonize on and around the medical device and, upon attaching to surfaces of the device, proliferate and form aggregates resulting in biofilm formation. This may lead to the failure of the working of the device.

Biofilms commonly grow in showers as well as on floors and counters making it difficult to maintain sanitary conditions in food preparation areas and medical settings. Biofilms are also found in marine engineering systems, such as pipelines of the offshore oil and gas industry may lead to substantial corrosion problems. At least 20% of corrosion is caused by micro-organisms that are attached to the metal subsurface. Biofilms may form on the surface of stagnant pools of water. Biofilms may be found on the surface of plants and may contribute to crop disease. Examples of crop disease related to biofilms include Citrus Canker, Pierce's Disease of grapes and Bacterial Spot of plants such as peppers and tomatoes.

Figure 4:
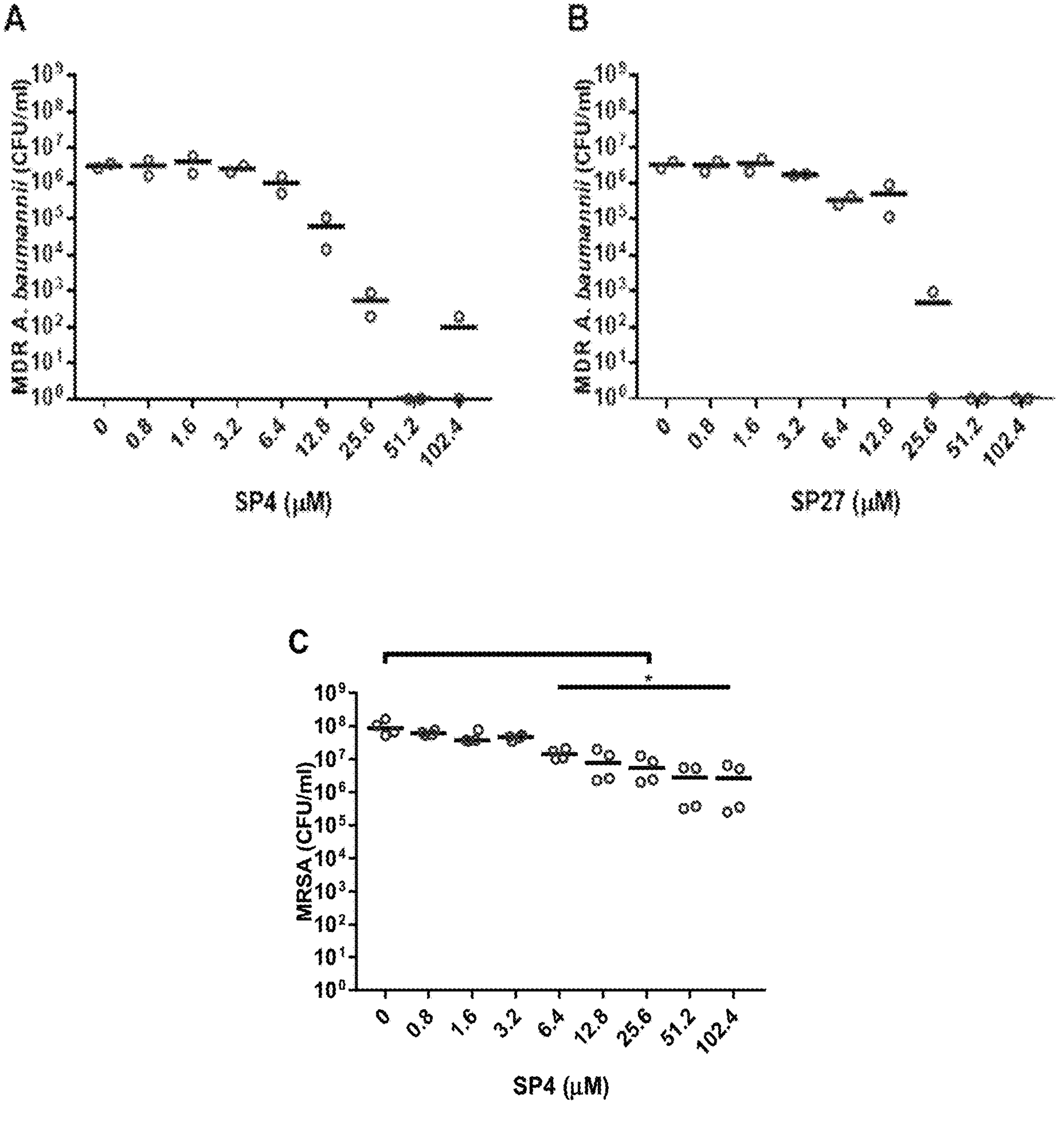
FIG. 4: Degradation of an established *A. baumannii* and *S. aureus* biofilm by SP4 and SP27. Dose-dependent degradation of a 24-hour biofilm of *A. baumannii* RUH 875 after a 2-hour treatment with SP4 (Panel A) and SP27 (Panel B). Results are expressed as the CFU/ml. Panel C) Dose-dependent degradation of a 24-hour matured biofilm of *S. aureus* LUH 14616 after a 2-hour treatment with SP4. The results are expressed as the CFU/ml. Significance compared to control (0 μM) was calculated with the Mann-Whitney U test (*P<0.05).
Figure 5:
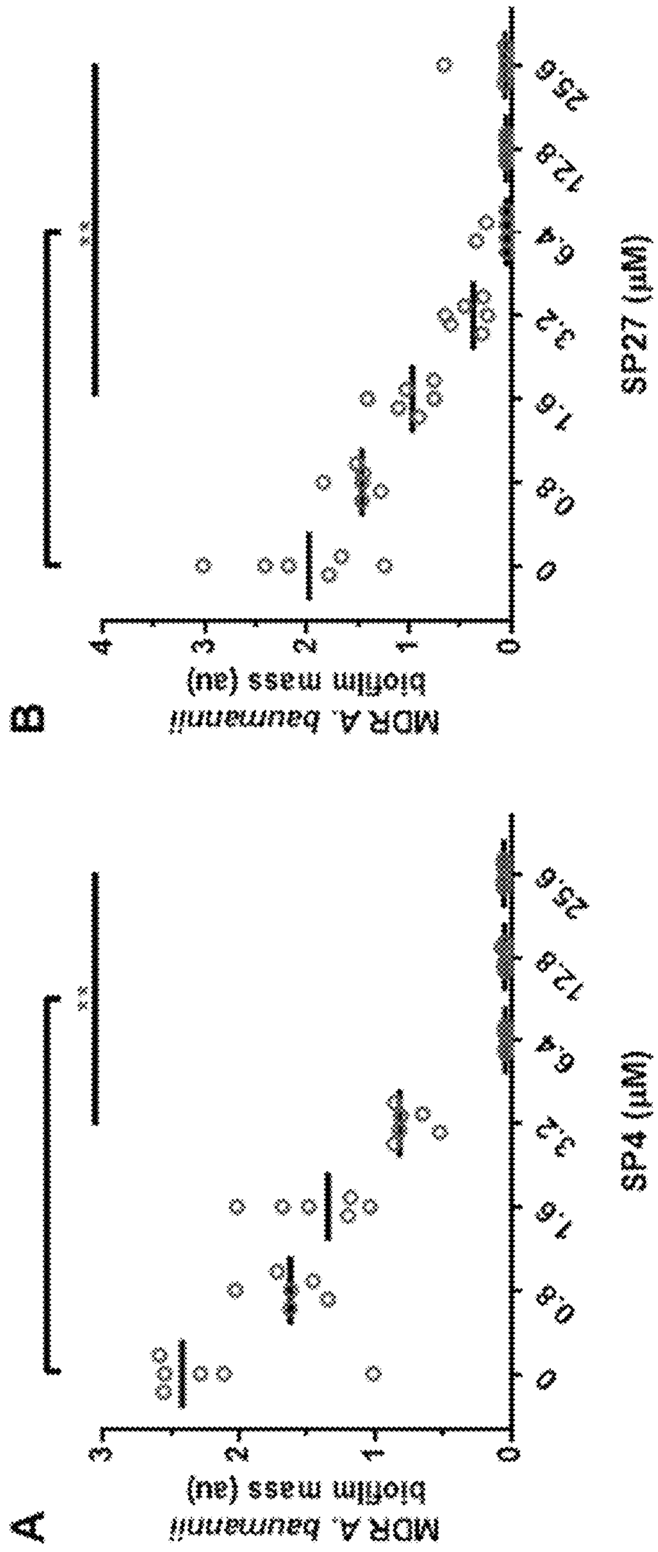
FIG. 5: Prevention of biofilm formation by SP4 and SP27. *A. baumannii* RUH 875 bacteria were incubated with increasing SP4 (A) and SP27 (B) concentrations in BM2 medium for 24 hours. Thereafter, biofilms were stained with crystal violet and the biofilm mass quantified by determining the optical density of the crystal violet staining. Results are medians of sixplicates from one experiment. Results are expressed as the biofilm mass in arbitrary units (au). Significance compared to control (0 μM) was calculated with the Mann-Whitney U test (**P<0.01).

Although not wanting to be bound by theory, the limited access to nutrients in a biofilm is thought to result in metabolically inactive bacteria leading to bacterial "tolerance" and "persistence" as described herein. The reliance of antibiotics on bacterial growth and multiplication renders these compounds generally ineffective against biofilm. In contrast, FIGS. 4 and 5 depict the ability of the peptides disclosed herein to degrade biofilms and prevent their formation, respectively.

The peptides and compositions disclosed herein are also useful for treating and/or preventing viral infection, particularly in a human or animal. As used herein, "treating and/or preventing viral infection" refers to delaying, inhibiting or preventing a viral infection, decreasing the viral load as compared to the viral load without treatment, as well as delaying, inhibiting, preventing, or reducing the severity of one or more symptoms of a viral infection. Examples of pathogenic viruses that may cause infections in humans or animals that are treatable with polypeptides and compositions of the disclosure include, but are not limited to, A, B or C hepatitis, herpes virus (for instance, VZV, HSV-I, HAV-6, HSV-II, CMV, Epstein-Barr virus), adenovirus, influenza virus, flaviviruses (e.g., yellow fever, dengue and chikungunya virus), echovirus, rhinovirus, coxsackie virus, coronavirus, respiratory syncytial virus (RSV), rotavirus, Morbillivirus, rubella virus, parvovirus, vaccinia virus, HTLV virus, papillomavirus, poliovirus, rabies virus and human immunodeficiency virus (HIV virus; e.g., type I and II). The peptides, nucleic acids, vectors, or compositions comprising same, may be administered to an individual in need thereof by any means known to a skilled person and may be administered to an individual at risk of developing a viral infection or to an individual after a viral infection has been diagnosed.

The peptides and compositions disclosed herein are useful for ex vivo applications, e.g., as anti-viral agents. Method are disclosed herein for inhibiting viruses on a surface or in a composition comprising providing the surface or composition with a peptide as disclosed herein. As used herein, "inhibiting a virus" refers to inhibiting or slowing viral growth/replication as well as promoting viral inactivation/degradation.

Virus plaque assays may be used to assess the antiviral activity of a peptide as disclosed herein. In short, a virus inoculum is exposed to the peptide prior to infection of a permissive cell monolayer. After a standard interval, the virus titer in the cellular extracts is determined using multiple dilutions of these extracts by infecting fresh cell monolayers and quantifying their effects on the cell monolayer.

The peptides and compositions disclosed herein are useful for treating and/or preventing fungal infection, particularly in a human, animal or crop plant. As used herein, "treating and/or preventing fungal infection" refers to delaying, inhibiting or preventing, or reducing the severity of one or more symptoms of a bacterial infection. Examples of pathogenic fungi that may cause infections in humans, animals or crop plants that are treatable with polypeptides and compositions of this disclosure include, but are not limited to *Candida* (e.g., *albicans, krusei, glabrata, tropicalis*), *Aspergillus* (e.g., *fumigatus, niger*), *Cryptococcus neoformans, Histoplasma capsulatum*, Genus Mucorales, *Blastomyces dermatitidis, Paracoccidioides brasiliensis*, and *Coccidioides immitis*. Accordingly, provided is the use of the peptides as disclosed herein for treating a human or animal. The peptides, nucleic acids, vectors, or compositions comprising same, may be administered to an individual in need thereof by any means known to a skilled person and may be administered to an individual at risk of developing a fungal infection or to an individual after a fungal infection has been diagnosed.

The peptides and compositions disclosed herein are useful for ex vivo applications, e.g., as anti-fungal agents. Method are disclosed herein for inhibiting fungi on a surface or in a composition comprising providing the surface or composition with a peptide as disclosed herein. As used herein, "inhibiting fungi" refers to inhibiting or slowing hyphenation, as well as promoting fungal death.

The peptides and compositions disclosed herein are useful for treating and/or preventing parasitic infection, particularly in a human or animal. As used herein, "treating and/or preventing parasitic infection" refers to delaying, inhibiting or preventing, or reducing the severity of one or more symptoms of a parasitic infection. Examples of pathogenic parasites that may cause infections in humans or animals that are treatable with polypeptides and compositions of the disclosure include, but are not limited to, *Entamoeba histolytica, Plasmodium* (e.g., *falciparum, vivax*), *Entamoeba, Giardia, Balantidium coli, Acanthamoeba, Cryptosporidium* sp., *Pneumocystis carinii, Babesia micron, Trypanosoma* (e.g., *brucei, cruzi*), *Leishmania* (e.g., *donovani*), and *Toxoplasma gondii*. Accordingly, provided is the use of the peptides as disclosed herein for treating a human or animal. The peptides, nucleic acids, vectors, or compositions comprising same, may be administered to an individual in need thereof by any means known to a skilled person and may be administered to an individual at risk of developing a parasitic infection or to an individual after a parasitic infection has been diagnosed.

The peptides and compositions disclosed herein are useful for ex vivo applications, e.g., as anti-parasitic agents. Method are disclosed herein for inhibiting parasites on a surface or in a composition comprising providing the surface or composition with a peptide as disclosed herein. As used herein, "inhibiting parasites" refers to inhibiting or slowing down parasitic growth and/or development as well as promoting parasitic death.

For assessment of anti-parasitic activity, a peptide as disclosed herein and a parasite are incubated for a standard time interval. Thereafter, the metabolic activity of the parasites may be analyzed directly, for instance, by an MTT assay, or the parasites are transferred to mammalian cells and, after incubation, parasite multiplication in these cells is assessed by microscopy.

The peptides and compositions disclosed herein are useful for treating an inflammatory condition or modulating an immune response, particularly in a human or animal. In particular, the inflammatory condition is an inflammatory response in an individual suffering from a bacterial, fungal, viral and/or parasitic infection. While not wishing to be bound by theory, the anti-inflammatory activity of peptides disclosed herein may be achieved by inhibiting, reducing or preventing the release of pro-inflammatory cytokines/molecules upon exposure to microbial compounds, such as lipoteichoic acid (LTA), peptidoglycan (PG) and/or lipopolysaccharides (LPS). The peptides are thus useful as anti-inflammatory agents as they neutralize the pro-inflammatory actions of microbial endotoxins such as lipoteichoic acid, peptidoglycan and lipopolysaccharides thereby inhibiting, reducing or preventing influx of neutrophils, macrophages/monocytes and lymphocytes and the release of pro-inflammatory compounds by the infected subject. Accordingly, Further provided are methods for inhibiting the release of pro-inflammatory compounds comprising contacting a cell capable of releasing pro-inflammatory compounds with a peptide as disclosed herein. Contacting may be performed in vivo and in vitro.

Anti-inflammatory activity may be measured by methods known in the art. One example of such method is a lipopolysaccharide neutralization assay. In this method, a polypeptide of the disclosure is mixed with 1 mg of lipopolysaccharides and incubated for 60 minutes. Thereafter, these mixtures were added to 4 times diluted fresh human blood and 18 hours thereafter the level of cytokines (IL-8, IL-12p40) in the blood sample are measured by ELISA.

Further provided are the use of peptides as disclosed herein to redirect the tumor-tolerating immune response towards a tumor-controlling response. Redirection of the immune response may be measured by methods known in the art. One example of such a method is the redirection of the MCF-driven as well as tumor conditioned medium-driven differentiation of monocytes towards macrophages with a pro-inflammatory signature.

Further provided are the use of the peptides as disclosed herein as diagnostics. In particular, the peptides may be used to detect a bacterial, fungal, viral and/or parasitic infection. For example, a peptide may be coupled to a suitable moiety such as a biotin, a fluorescein label, a near infrared dye or a radioactive isotope. The labelled peptide may then be administered to an individual having or suspected of having an infection. The peptide may then localize to the site of infection, if present, and may be detected by suitable means.

The peptides and compositions disclosed herein are useful for protecting plants and may be used in methods for treating and/or preventing infection of a plant, particularly in a crop plant. As used herein, "treating and/or preventing infection of a plant" refers to delaying, inhibiting or preventing, or reducing the severity of infection or of one or more symptoms of an infection in the plant. Examples of pathogenic infections that may cause infections of a plant that are treatable with polypeptides and compositions of the disclosure include, but are not limited to, fungi from the Ascomycetes and Basidiomycetes species, bacteria such as *Burkholderia*, Proteobacteria (e.g., *Xanthomonas* and *Pseudomonas*) and viruses such as Tobacco mosaic virus, Cauliflower mosaic virus, Cucumber green mottle mosaic virus and Pepino mosaic virus. Accordingly, provided is the use of the peptides as disclosed herein for plant protection.

The peptides, nucleic acids, vectors, or compositions comprising same, may be provided to a plant by any means known to a skilled person and may be provided to a plant at risk of developing an infection or after an infection has been diagnosed. For example, plants may be sprayed with a composition as disclosed herein if crops in a neighboring field are infected.

For assessment of protective activity, a peptide as disclosed herein is administered to a plant. Thereafter, the plant is infected with a pathogen, for instance, with a bacteria, virus, fungi or parasite. After incubation for a time sufficient to infect the plant, the plant is analyzed for infection symptoms. Preferably, the plant is compared to other plants infected with the same pathogen that were not pre-treated with the peptide.

Further provided are a method for protecting a plant comprising contacting the plant with a peptide, nucleic acid molecule, vector, and/or composition as disclosed herein. As used herein, "protecting a plant" refers to protecting a plant against disease and/or infection. Preferably, protecting against infection with bacteria, fungi, viruses and/or parasites, and/or reducing the severity of bacterial, fungal, virus and/or parasite infections. Protection may result in a reduction of the multiplication of the bacteria, fungi, viruses and parasites. Protection may result from killing the bacteria, fungi, viruses and/or parasites. Preferably, the methods as described herein comprise exposing a plant or plant part to an effective dosage of the peptide as described herein.

The peptides and compositions disclosed herein are useful for treating a cancer in an individual. In some embodiments, the peptides and compositions disclosed herein are useful for promoting an anti-tumor immune response. In some embodiments, topical compositions are provided comprising the peptides disclosed herein. In some embodiments, the cancer is selected from melanomas, epithelioid cervix carcinomas and ovarian carcinomas.

Further provided are the use of the peptides disclosed herein in screening and research applications. In some embodiments, methods are provided comprising providing the isolated or recombinant peptide, the nucleic acid molecule, the vector and/or the composition as disclosed herein to a system. Exemplary systems include cell culture, cell-free in-vitro systems, animal models, and organoid cultures. As used herein, cell culture refers to any kind of cell culture, including mammalian cell culture, insect cell culture, plant cell culture, bacterial cell culture, yeast cell culture. Cell culture includes both small and large scale cell culture, for example, at industrial scale.

In such systems, the peptides may be used to induce or inhibit various processes. For example, the growth of in vitro cultured carcinoma cells may be reduced or the excretion of cytokines by in vitro-cultured immune cells may be influenced. The disclosed systems are also useful for performing screening assays.

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, the additional component(s) not altering the unique characteristic of the disclosure.

The articles "a" and "an" are used herein to refer to one or to more than one (i.e., to at least one) of the grammatical object of the article. By way of example, "an element" means one element or more than one element.

REFERENCES

Bahar A. A., Ren D. "Antimicrobial peptides." Pharmaceuticals. 2013; Vol. 6: p1543-15'75; doi:10.3390/ph6121543.

Boucher H. W., Talbot G. H. et al. "*Bad Bugs, No Drugs*: No ESKAPE! An Update from the Infectious Diseases Society of America." *Clin. Infect. Dis.* 2009; Vol. 48: p1-12.

Brauner et al. Distinguishing between resistance, tolerance and persistence to antibiotic treatment. *Nature* 2016, Vol. 14: p321-330.

Cai S., Qiao X. et al. "Python cathelicidin CATHPb1 protects against multidrug-resistant staphylococcal infections by antimicrobial-immunomodulatory duality." *J. medicinal chemistry* 2018; Vol. 61: p2075-2086.

Cho Y. C., Lee S. H. et al. "Enhanched IL-12p40 production in LPS-stimulated macrophages by inhibiting JNK activation by artemisinin." *Arh. Pharm. Res.* 2012; Vol. 35: p1951-1968.

De Kraker M. E. A., Stewardson A. J., Harbarth S. "Will 10 Million People Die a Year due to Antimicrobial Resistance by 2050*?" PLoS Med.* 2016; doi:10.1371/journal.

De Latour F. A., Amer L. S. et al. "Antimicrobial activity of the *Naja atra* cathelicidin and related small peptides." *BBRC.* 2010; Vol. 396: p825-830.

Dean S. N. et al. "Natural and synthetic cathelicidin peptides with anti-microbial and anti-biofilm activity against *Staphylococcus aureus." BMC Microbiology* 2011; doi: 10.1186/1471-2180-11-114.

Falcao C. B. et al. Vipericidins; a novel family of cathelicidin-related peptides from the venom gland of South American pit vipers. *Aminoacids* 2014; Vol 46: p2561-2571.

Høiby N., Bjarnsholt T. et al. "Antibiotic resistance of bacterial biofilms." *International J. Antimicrobial Agents* 2010; Vol. 35: p322-332.

Kościuczuk E. M., Lisowski P. et al. "Cathelicidins: family of antimicrobial peptides. A review." *Mol. Biol. Rep.* 2012; Vol. 39: p10957-10970.

O'Neill. "Tackling drug-resistant infections globally: Final report and recommendations." 2016; on the world-wide web at amr-review.org/sites/default/file s/160518_Final %20paper_with %20cover.pdf.

Olsen I. "Biofilms-specific antibiotic tolerance and resistance." *Eur. J. Clin. Microbiol.* Infect. Dis. 2015; Vol. 34: p877-886.

Overhage J., Campisano A. et al. "Human host defense peptide LL-37 prevents bacterial biofilm formation." *Infect. Immun.* 2008; Vol. 76: p4176-4182.

Scott M. G., Davidson D. J. et al. "The human antimicrobial peptide LL-37 is a multifunctional modulator of innate immune responses." *J. Immunol.* 2002; Vol. 169: p3883-3891.

Shek K. C., Tsui K. L. et al. "Oral bacterial flora of the Chinese cobra (*Naja atra*) and bamboo pit viper (*Trimeresurus albolabris*) in Hong Kong SAR, China." *Hong Kong Med. J.* 2009; Vol. 15: p183-190.

Van der Does A. M. et al. LL-37 directs macrophage differentiation toward macrophages with a pro-inflammatory signature. *J. Immunol.* 2010; Vol 185: p1442-1449.

Von Rosenvinge et al. *Microbial biofilms and gastrointestinal diseases*. Pathog. Dis. 2013; 67: p25-38.

Wang H. et al. *BF*30 *selectively inhibits melanoma cell proliferation via cytoplasmic membrane permeabilization and DNA-binding in vitro and in B* 16*F*10*-bearing mice. Eur. J. Pharmacol.* 2013; Vol 707: p1-10.

Zhao F., Lan X. Q. et al. "King cobra peptide OH-CATH30 as a potential candidate drug through clinic drug-resistant isolates." *Zoological research.* 2018; Vol. 39: p8'7-96.

The disclosure is further explained in the following examples. These examples do not limit the scope of the disclosure, but merely serve to clarify the disclosure.

EXAMPLES

Example 1

The present study is to identify optimal candidates for the development of novel agents. In this connection, first compared were the antibacterial and hemolytic activities of cathelicidins from various snakes. From this screening, the two most promising peptides were selected for further investigation studies of, i.e., their ability to kill multidrug resistant bacteria, to interfere with biofilm formation, to induce resistance, to modulate inflammatory responses, and to kill cancer cells.

In order to select promising antimicrobial peptides sequences encoding for cathelicidins found in the genome of various snakes were tested for their bactericidal activity against MRSA and multi drug resistant (MDR) *P. aeruginosa* with an in vitro killing assay. The peptides were also tested for their hemolytic activity as an indicator for their toxicity. In this hemolysis assay, red blood cells were mixed with the peptide. If the peptide was toxic, the cells would lyse and thereby release their hemoglobin, which could be measured. As a positive control TRITON® X-100 was used, this is a surfactant that lyses the red blood cells.

The snake peptides that had a promising antimicrobial activity and a low toxicity were selected and tested more extensively. As a start the two most potent peptides, being SP4 and SP27, were tested further for antibacterial activity against the multidrug resistant strains of the ESKAPE panel and colistin-resistant *E. coli* in a killing assay.

Next, the ability of MRSA to form resistance against SP4 and SP27 was assessed in a resistance development assay. In this assay the bacteria are incubated with peptide in a serial passing, with the half MIC being used for the subsequent passage to select for resistant isolates.

The peptides were tested on MDR *A. baumannii* for biofilm degrading activity and the ability to prevent biofilm formation. For the biofilm degradation an established biofilm of 24 hours was grown and then treated with the peptide, where after sonicating the number of viable bacteria could be determined. For the biofilm preventing ability the bacteria and peptide are incubated together for 24 hours. This incubation takes place in biofilm medium 2 (BM2), this is a minimal medium allowing bacteria to survive and form a biofilm (Overhage et al., 2008). After incubation a crystal violet stain was used to assess the mass of the formed biofilms.

To simulate a more in vivo like experiment the ability of SP4 and SP27 to reduce a MRSA colonization on ex vivo human skin was tested. Therefore, ex vivo skin punches have been inoculated with bacteria and thereafter treated with peptide. After treatment the number of viable bacteria could be determined.

To determine if the peptides also have immunomodulatory effects, the chemotactic activity, the lipopolysaccharide (LPS) neutralizing effect and the ability to redirect M-CSF-driven monocyte-macrophage differentiation were examined. For the chemotactic effect neutrophils were obtained after ficoll separation and the use subsequent lysis of the red blood cells within the neutrophil-containing fraction. The neutrophils were added to an insert with the peptide in the lower compartment as chemoattractant. As a positive control fMLP (N-formyl-Met-Leu-Phe) was used, this is a peptide with potent chemotaxis activities (sigma Aldrich cat number F3506). After the incubation period the number of migrated neutrophils in the lower compartment was measured by FACS. The ability of the peptides to neutralize LPS was tested in a LPS neutralization assay. The LPS was pre-incubated with the peptide and added to whole blood. If the LPS is neutralized by the peptide it will not be able to stimulate the IL-12p40 production by the blood cells (Cho et al., 2012), measured with an ELISA. The ability of the peptides to redirect monocyte-macrophage differentiation was assessed in cultures of human monocytes exposed to M-CSF (van der Does at al., 2010). Finally, the tumoricidal activity of the peptides was assessed in cultures of primary human melanocytes and 4 different melanoma cell line cells.

Materials and Methods

Bacterial Strains and Culturing

*Enterococcus faecium* (LUH 15122), *Staphylococcus aureus* (LUH 14616), *Klebsiella pneumoniae* (LUH 15104), *Acinetobacter baumannii* (RUH 875), *Pseudomonas aeruginosa* (LUH 15103), *Enterobacter cloacae* (LUH 15114) and *Escherichia coli* (LUH 15117) were used. Prior to experimentation the bacteria were taken from a glycerol stock stored at −80° C. and cultured overnight on sheep blood agar plates at 37° C. On the day of experimentation the bacteria were cultured in tryptic soy broth (TSB; Oxoid) for 2.5 hours at 37° C. and 200 rpm to a mid-logarithmic phase. The bacterial suspension was washed in phosphate buffered saline (PBS; pH 7.4), centrifuged for 10 minutes at 3000 rpm, and resuspended in PBS to the desired concentration, as determined by measuring the absorbance at 600 nm.

Peptides

Mining the genomes of 17 different snake species (see Table 1) for genes encoding members of the cathelicidin family resulted in the identification of 35 different genomic sequences. The predicted amino acid sequences of the various mature snake cathelicidins were produced using solid phase peptide synthesis by F-MOC technology. The peptides were over 98% pure as assessed by HPLC. In addition, batch of HPLC-purified SP4 and SP27 were prepared. Furthermore, a set of snake peptide 4 shortened at the N and the C termini with one up to 10 amino acids was prepared.

Bactericidal Activity of Peptides

A bacterial suspension of $5\times10^6$ CFU/ml was added to peptides solutions ranging from final concentrations of 0.8 μM to 102.4 μM in PBS with either 50% (v/v) pooled human plasma (Sanquin) or 50% pooled urine (from healthy volunteers) in a polypropylene 96-well flat-bottom plate (Greiner). As a control the bacteria were also incubated in PBS with either 50% plasma or 50% urine without peptide. The plate was incubated for 2 hours at 37° C. and 200 rpm. After incubation the number of viable bacteria was determined microbiologically by plating the samples and a 10-times dilution series in PBS on diagnostic sensitivity test agar plates (DST; Sigma). The DST plates were incubated overnight at 37° C. Results were expressed as lethal concentration 99.9, or $LC_{99.9}$, which represents the lowest concentration of peptide that killed 99.9% of the bacteria within 2 hours of incubation.

Hemolysis Assay

Whole blood was collected (from healthy volunteers) in citrate tubes and centrifuged for 10 minutes at 3000 rpm. The pellet containing the erythrocytes was washed in PBS three times for 10 minutes at 1000 rpm. From the pellet a 20% erythrocyte suspension was made in PBS. The 20% erythrocyte suspension was diluted 10 times to form a 2% (v/v) erythrocyte suspension. In a polypropylene V-bottom plate 50 μl of human plasma were added to 25 μl of peptide solutions with final concentrations ranging from 12.8 μM to 204.8 μM in triplicate. Next, 25 μl of the 2% erythrocyte solution were added to the wells containing peptide and plasma. As a negative control wells containing 25 μl of PBS instead of peptide were included. As a positive control wells with 25 μl of 5% (v/v) TRITON®-X (Sigma-Aldrich) were included. The plate was sealed off with sealing tape (Costar) and the suspensions mixed by shaking for 10 seconds at 300 rpm. Thereafter, the plate was incubated for 1 hour at 37° C. For analysis, the plate was centrifuged for 5 minutes at 2000 rpm. From the supernatant 75 μl were transferred to a polystyrene 96-well flat-bottom plate and the absorbance at 415 nm was assessed. Results were expressed as the highest concentration that resulted in <5% erythrocyte lysis.

Resistance Development Assay

A bacterial culture was prepared and washed as described before. The bacterial culture was diluted to a concentration of $5\times10^6$ CFU/ml in modified RPMI 1640 comprising 20 mM HEPES, L-glutamine and without sodium bicarbonate (RPMImod; Sigma-Aldrich). In a polypropylene 96-well plate, a two-fold peptide dilution series was made in RPMI-mod with concentrations ranging from 0.94 μM to 240 μM. An antibiotic dilution series of ciprofloxacin and rifampicin (Sigma-Aldrich) was added with concentrations ranging from 0.25 μg/ml to 500 μg/ml in RPMImod. A negative control of RPMImod without peptide or an antibiotic was included for both dilution series. A contamination control was included containing only RPMImod. To all the wells, except the contamination control wells, 5 μl of the bacterial suspension were added. The plate was sealed and incubated overnight at 37° C. and 200 rpm. After incubation the MIC was determined as the well with the lowest peptide concentration and no bacterial growth. The well with half the MIC was diluted 2.5-fold with RPMImod and transferred to an Eppendorf tube. For the next passage the peptide and antibiotic series were prepared as described before and 5 μl of the half MIC were added. The results were expressed as the fold increase of the MIC compared to the MIC at the first passage.

Biofilm Breakdown as Say

To a polypropylene 96-well flat-bottom plate (Greiner) 50 μl of a bacterial suspension at a concentration of $1\times10^7$ CFU/ml in BM2 medium (Overhage et al., 2008) were added. A control comprising BM2 medium alone was included. The plate was sealed off with a seal (Costar) and incubated in a humidified environment for 24 hours at 37° C. Thereafter the wells were washed 2 times with PBS. Next, the wells were exposed to 100 μl of peptide solution ranging from final concentrations of 0.8 μM to 102.4 μM, and a control without peptide was included. The plate was sealed off and incubated for 2 hours at 37° C. and 200 rpm. For analysis the plate was sonicated (Ultrasoonbad BRANSONIC® m1800H-E; Boom b.v.) for 5 minutes to detach the biofilm bacteria. The number of viable bacteria in the sonicates was determined microbiologically by plating the samples and a 10-times dilution series on DST agar plates and incubating these overnight at 37° C. Results were expressed as the LC99.9.

Biofilm Prevention Assay

In a polypropylene 96-well flat-bottom plate 50 μl of peptide solution in BM2 medium was added to achieve final concentrations ranging from 0.8 μM to 25.6 μM in sixplicate. From a bacterial suspension with a concentration of $1\times10^7$ CFU/ml in BM2 medium 50 μl was added to the wells with peptide. As an untreated control the bacteria were added to BM2 medium without peptide. As a contamination control BM2 medium alone was included. The plate was sealed off and incubated for 24 hours at 37° C. in a humidified environment. After incubation the wells were washed four times with PBS. Next, the biofilm bacteria were stained with 1% crystal violet (Sigma-Aldrich) for 10 minutes at room temperature. The excess crystal violet was washed away with PBS four times. Subsequently, 96% ethanol was added to the wells and incubated for 10 minutes at room temperature. The supernatant was transferred to a polystyrene 96-well flat-bottom plate and the absorbance at 595 nm measured. Results were expressed as arbitrary units (au), i.e., biofilm mass, as measured after crystal violet staining.

Ex Vivo Skin Model

The donor skin was transported to the LUMC in RPMI 1640 medium (Gibco) supplemented with penicillin/streptomycin (Gibco). Skin samples were washed in PBS and left overnight in RPMI 1640 medium without antibiotics. On the day of the experiment the skin was again washed in PBS, then spread out and punches with a diameter of 8 mm diameter were made with a biopsy punch (Stiefel). The skin samples were dried with a cotton swab. A liquid dam was made with LC Block-Out Resin (Ultradent) on the edge of the skin samples to prevent liquids from dripping off. The liquid dam was solidified by 4 seconds exposure of UV light (Super 1200 led; ECO). The skin samples were placed on grids in a 12-well plate (Costar) filled underneath with medium comprising Ham F12, DMEM and FCS (Gibco). An *S. aureus* LUH 14616 bacterial suspension was cultured and washed as described before. The skin punches were inoculated with 5 μl of the bacterial suspension ($1\times10^8$ CFU/ml) for one hour at 37° C. and 5% $CO_2$. Peptide concentrations ranging from 2.5 μM-204.8 μM were made in PBS. The infected skin was treated for 1 hour at 37° C. and 5% $CO_2$ with 10 μl of the peptide solutions, including a control with 10 μl of PBS alone. Polypropylene tubes were filed with glass beads (1.7 mm diameter) and 1 ml of PBS. The liquid dam was removed from the skin after treatment. The skin was transferred to the tubes with beads and beated two times for 20 seconds in the MINILYS® bead beater (Bertin Technologies), the samples were placed on ice between the beatings. The beated samples were diluted in a 2-times dilution series and plated on a DST agar plate. The DST plates were incubated overnight at 37° C. Results were expressed as the number of viable bacteria (CFU/ml) after treatment.

Neutrophil Migration Assay

Heparinized blood was collected from healthy human volunteers. Next, 10 ml of blood were mixed to 15 ml of PBS in a tube. Underneath the diluted blood, 10 ml of Ficoll (Pharmacy, LUMC) were added. The tube was spun at 1800 rpm for 20 minutes without brake. The supernatant was removed and 40 ml of erythrocyte lysis buffer (0.1 mM EDTA, 0.18 M NH4Cl, 10 mM KHCO3) were added to the pellet. This mixture was incubated at room temperature until erythrocyte lysis was evident. The tube was centrifuged at 1200 rpm for 10 minutes, the supernatant was discarded. The pellet was washed again with PBS the same way. The pellet was resuspended in RPMI 1640 medium and the cells were counted with a counting chamber. The cells were diluted to $2\times10^6$ cells/ml of RPMI 1640. The inserts with a 3.0 μm pore size in a 12-well plate (HTS transwell; Costar) were blocked with 400 μl of PBS with 0.1% w/v BSA for 10 minutes at room temperature after which the BSA solution was discarded. The $2\times10^6$ cells/ml suspension was diluted with RPMI to add 400 μl of a $2\times10^5$ cells/ml suspension to the inserts. Peptide solutions with concentrations ranging from 3.2 μM to 12.8 μM were made in RPMI 1640 as chemoattractant. In the lower compartment 1 ml of the chemoattractant was added. A positive control 10 nM fMLP (Sigma-Aldrich) in RPMI supplemented with 10% v/v heat inactivated fetal calf serum (FCSi; Gibco) and as a negative control 1 ml of RPMI were used. The plate was incubated for 90 minutes at 37° C. and 5% $CO_2$. After incubation 50 μl of 50 mM EDTA (Sigma) were added to the lower compartment. The cells that had migrated to the lower compartment were transferred to a FACS tube and enumerated on the Accuri flowcytometer C6 (BD). Results were expressed as the percentage of migrated neutrophils compared to the positive FMLP control, and corrected for the negative control.

LPS Neutralization by Peptides

Heparinized blood collected from healthy human volunteers was diluted five times in RPMI 1640. Next, 195 μl of diluted blood were pipetted in to the wells of a 96-well cell culture plate. In another 96-well polypropylene V-bottom plate, 15 μl of peptide solution with final concentrations of 1 nM to 1000 nM were mixed with 15 μl of 500 ng/ml lipopolysaccharide from *E. coli* J5 (LPS; Sigma) for 30 minutes at 37° C. and 200 rpm. After incubation the mixtures were diluted five times with 120 μl of RPMI. From the diluted mixtures 5 μl were transferred to the wells of the plate containing the 195 μl of blood. The plate was incubated for 20 hours at 37° C. and 5% $CO_2$. The plate was centrifuged for 5 minutes at 1200 rpm. The supernatants were stored as aliquots at −20° C. until analysis of the cytokine level by ELISA. The IL-12p40 sandwich ELISA from Invitrogen was used. ELISAs were performed according to manufacturer's instructions. Results were expressed as the concentration IL-12p40 in pg/ml.

Selective Killing of Melanoma Cells by Peptides

Normal melanocytes (up to 4 passages) and 4 melanoma cell lines (mel 11.11, mel 12.13, mel 05.18, mel 09.03) were cultured overnight 37° C. at a concentration of $2\times10^4$ cells/well in 100 μl of DMEM supplemented with 7.5% (v/v) fetal calf serum in a humidified 5% $CO_2$ atmosphere. The next day 75 μl of medium were removed and then 25 μl of double concentrated peptide (SP4 and SP27) solutions prepared in DMEM supplemented with 0.5% human serum were added. After an incubation for 4 hours in a humidified 5% $CO_2$ atmosphere at 37° C. the supernatant was removed for measurement of the LDH release using the Roche kit. The background LDH release by the cells, determined by exposing the cells to DMEM with 0.5% serum without peptide, was subtracted from the values for the peptide-exposed cells. Finally, the results ae expressed as the percentage LDH release using the values found for triton-exposed cells as 100%.

Statistical Analysis

The comparison of two samples was first made with a Kruskal-Wallis analysis. Next, a Mann-Whitney U test was used. The Samples were considered statistically significant for $P<0.05$.

Results

Screening of Snake Peptides for Bactericidal Activity and Toxic Effect

To select candidates for development as a novel agent for treatment for infections caused by multi-drug resistant (MDR) bacteria, 35 synthetic snake peptides were screened for their bactericidal activity on a MDR *S. aureus* and a MDR *P. aeruginosa* strain in 50% v/v human plasma. The experiment (Table 1) revealed that the peptides may be categorized into three groups. Group I comprises 7 of 35 peptides with a LC99.9 of ≤6.4 μM for both MRSA and *P. aeruginosa*; Group II comprises 19 out of 35 peptides with a LC99.9>6.4 μM for MRSA and ≤12.8 μM for *P. aeruginosa*; Group III comprises 9 out of 35 peptides with a LC99.9≥102.4 μM for MRSA and >12.8 μM for *P. aeruginosa*.

Most peptides were more effective against the MDR *P. aeruginosa* strain than the MDR *S. aureus* strain. The LC99.9 for the peptides against MDR *S. aureus* differed among the panel of snake peptides ranging from 3.2 μM (SP4) to more than 102.4 μM (multiple peptides). Interestingly, the LC99.9 for the peptides against MDR *P. aeruginosa* ranged from as low as 0.2 μM (SP23) to concentrations higher than 102.4 μM (multiple peptides).

The snake peptides killed the bacteria in a dose-dependent manner. For example, SP4 requires a submicromolar concentration of 0.4 μM to kill 99.9% of the *P. aeruginosa* bacteria (FIG. 1, Panel A) and 3.2 μM for *S. aureus* (FIG. 1, Panel B). SP27 needs slightly higher concentrations, i.e., 0.8 μM for *P. aeruginosa* and 6.4 μM for *S. aureus* (FIG. 1, Panels C and D).

To determine its active domain, shorter versions of SP4 were synthesized and tested for bactericidal activity. Results indicated that a couple shorter versions were equally effective as SP4 (Table 2).

The snake peptides were also tested for their toxic effect on human erythrocytes. All snake peptides displayed low toxicity against human erythrocytes, for 23 out of 35 peptides a concentration of 204.8 μM resulted in less than 5% lysis of the erythrocytes (Table 1). Snake peptides 4 and 27 showed promising results in their bactericidal activity and their toxicity and, therefore, are selected for further testing.

Resistance Development Against SP4 and SP27

Next, the ability of SP4 and SP27 to select for resistance in *S. aureus* LUH 14616, *A. Baumannii* and *E. coli* was assessed. The MIC for both SP4 and SP27 remained constant for all 20 passages, whereas the MIC for imipenem and rifampicin started to increase after already a couple of passages. Together, the fold increase for SP4 and SP27 was considerable less than for the antibiotics.

Effect of Snake Peptides 4 and 27 on MDR Strains of the ESKAPE and Colistin-Resistant *E. coli*

Figure 3:
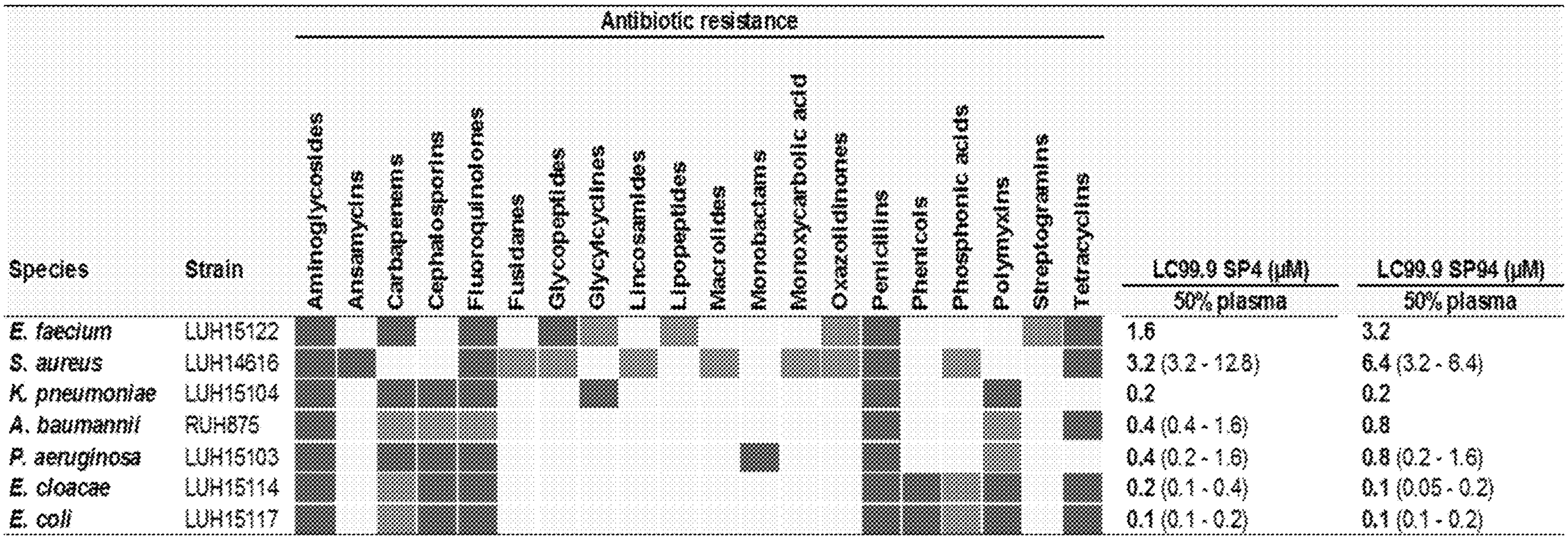
FIG. 3: Bactericidal activity of SP4 and SP27 on MDR ESKAPE strains and colistin-resistant *E. coli*. Bacteria were exposed to increasing concentrations of the snake peptides in 50% v/v human plasma (in the case of *E. coli* also in 50% pooled urine). After 2 hours, the surviving bacteria were plated on blood agar for microbiological assessment of the number of viable bacteria compared to the negative control, i.e., no peptide. The antibiotic resistance profiles of the various bacteria are indicated. If the bacteria are sensitive for the antibiotic class a green box is shown, the red box means that the bacteria is intermediate or resistant for at least one of the antibiotics in the class. A gray box means the susceptibility for that class has not been accessed. The bactericidal activity is expressed as the $LC_{99.9}$, i.e., the lowest dose of the peptide resulting in killing of 99.95 of the bacteria within 2 hours.

Thereafter, it was determined that the activity of the two most promising peptides, i.e., SP4 and SP27, against multidrug resistant strains of the ESKAPE panel and an *E. coli* resistant for colistin, a last resort antibiotic. The results showed that SP4 and SP27 are extremely effective (submicromolar concentrations) against MDR *K. pneumoniae, A. baumannii, P. aeruginosa, E. cloacae* and *E. coli* in PBS with 50% plasma (FIG. 3). For *E. faecium* and *S. aureus* low micromolar concentrations of SP4 and SP27 were sufficient to kill 99.9% of the bacteria. Determination of the ability of these snake peptides to kill *E. coli* in 50% v/v urine revealed a LC99.9 of 0.8 μM with a range of 0.8-1.6 μM for both peptides. Together, SP27 requires a slightly higher concentration than SP4 to kill the different species, except for the MDR *E. cloacae* and *E. coli* strains.

Biofilm Breakdown by SP4 and SP27

Next, the ability of SP4 and SP27 to degrade an established biofilm was determined. The results revealed that SP4 and SP27 dose-dependently degraded a 24 hours biofilm of *A. baumannii* with complete elimination of the biofilms seen at 51.2 μM peptide (FIG. 4, Panels A and B). MRSA biofilms were not efficiently degraded by SP4 at concentrations up to 102.4 μM (FIG. 4, Panel C).

Prevention of Biofilm Formation by SP4 and SP27

As *A. baumannii* biofilms were effectively degraded by SP4 and SP27, the ability of these peptides to prevent the formation of biofilms was then determined. The results revealed that SP4 and SP27 both completely prevented the biofilm formation of *A. baumannii* at ≥6.4 μM peptide (FIG. 5). As a control, the ability of these peptides to kill *A. baumannii* in BM2 medium was assessed. The results revealed that SP4 and SP27 eliminate all bacteria at concentrations of 1.6 μM peptide and higher and with 0.8 μM peptide reduce the amount of viable bacteria with 2 log, indicating that the bacteria may still kill the bacteria in the BM2 medium.

Elimination of *S. aureus* from Ex Vivo Human Skin by SP4 and SP27

Figure 6:
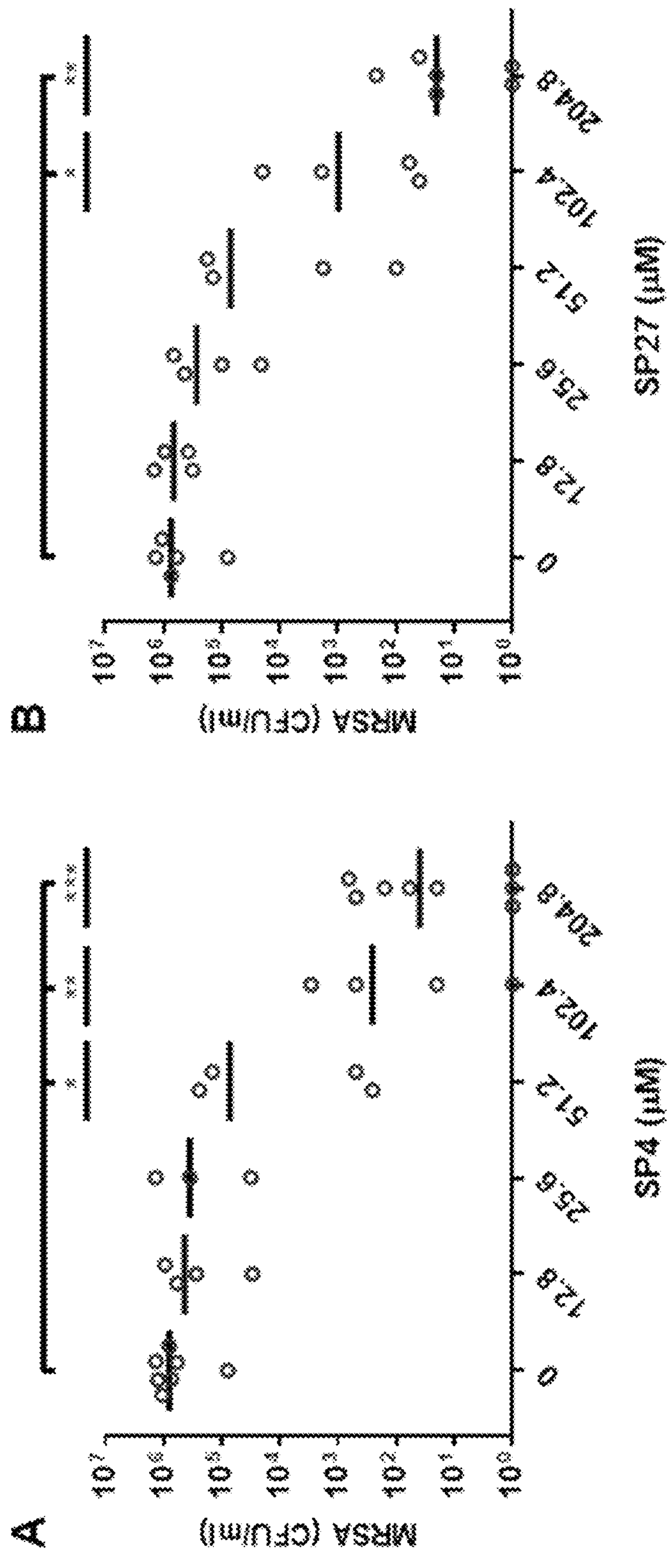
FIG. 6: Elimination of an MRSA infection on ex vivo human skin by SP4 and SP27. Ex vivo skin inoculated with MRSA treated for 1 hour with increasing concentrations SP4 (Panel A) and SP27 (Panel B). Significance compared to control (0 μM) was calculated with the Mann-Whitney U test (*P<0.05, P<0.01 and *P<0.001).

The ability of SP4 and SP27 to eliminate MRSA from ex vivo human skin was assessed. The results revealed that 10 μl of 102.4 μM SP4 was able to kill 99.9% of the MRSA (FIG. 6, Panel A). SP927 was slightly less effective in eliminating MRSA from the skin, with 99.9% elimination at 204.8 μM (FIG. 6, Panel B).

Effect of SP4 and SP27 on Neutrophil Migration

Figure 7:
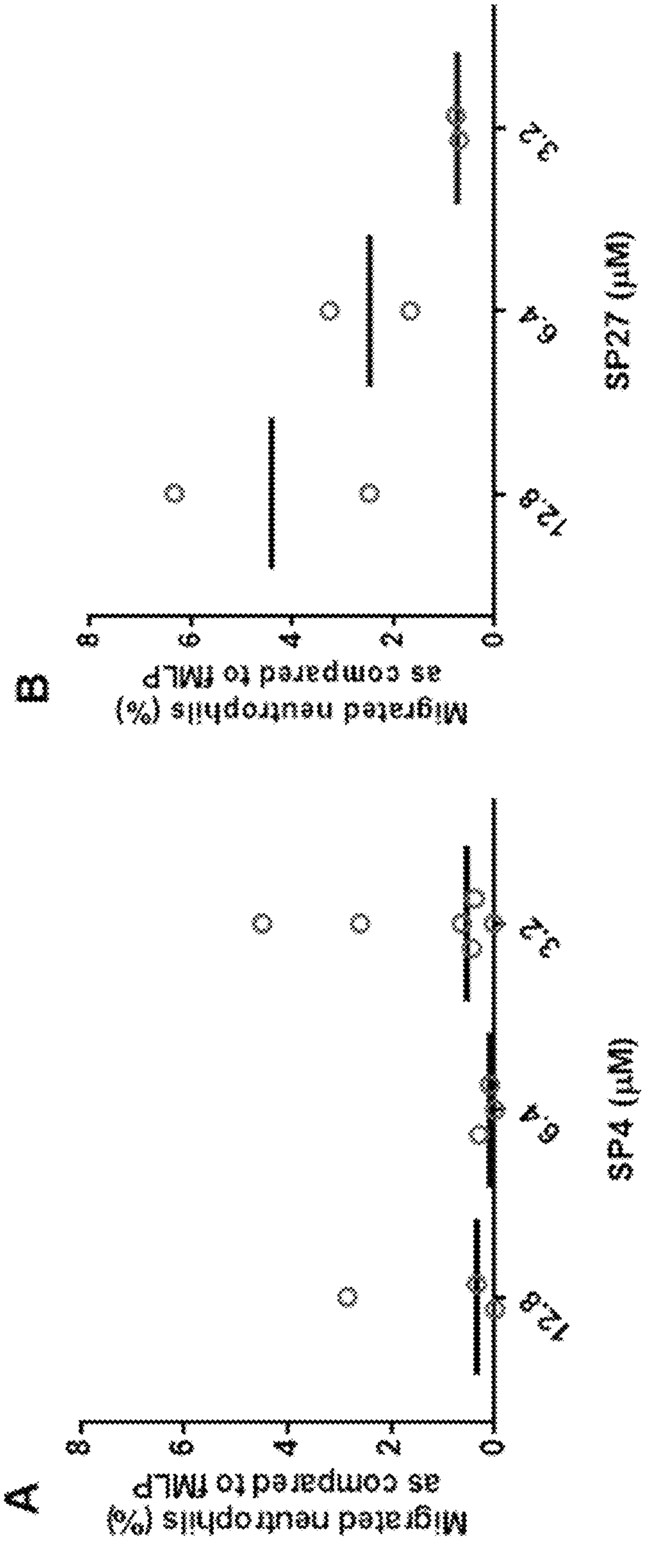
FIG. 7: Chemotactic effect of SP4 and SP27 on human neutrophils. Increasing concentrations of SP4 (Panel A) and SP27 (Panel B) were used as a chemoattractant to attract neutrophils from the upper compartment through an insert to the lower compartment during 90 minutes. Results are expressed as the percentage of migrated neutrophils compared to fMLP, the positive control (100%) and corrected for background migration (the negative control).

To obtain some information on the immunomodulatory abilities of the snake peptides, the chemotactic effects of SP4 and SP27 on human neutrophils were assessed. Results revealed that SP4 is poorly chemotactic at concentrations up to 12.8 μM (causes less than 1% of the neutrophils to migrate), compared to the positive control peptide fMLP (FIG. 7, Panel A). SP27 attracts the neutrophils in a dose-response, with 4.4% migrated neutrophils at 12.8 μM of peptide (FIG. 7, Panel B). LL-37 induces 5.6% of the neutrophils to migrate at a concentration of 3.2 μM peptide. So SP4 has little effect as chemo-attractant, while for SP27 the amount of migrated neutrophils increases with the concentration peptide.

LPS Neutralizing Ability of SP4

Figure 8:
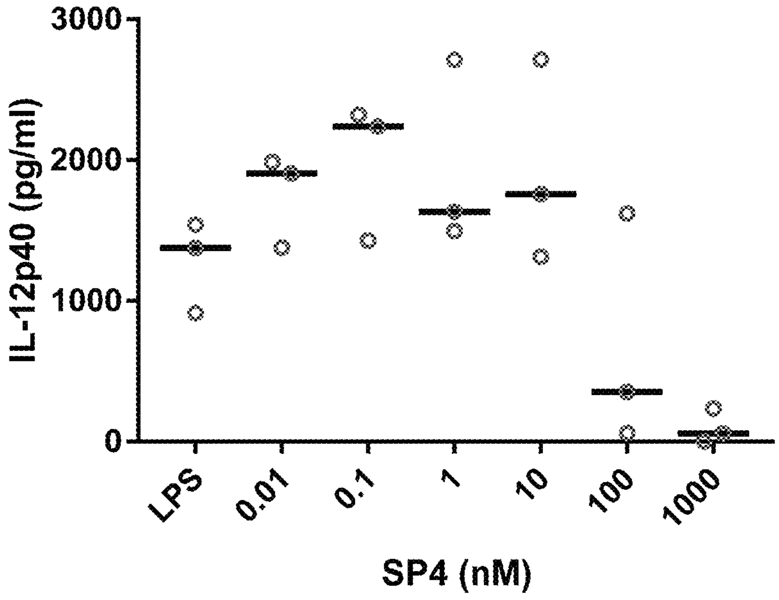
FIG. 8: LPS neutralization by SP4. In short, whole blood was incubated with 500 ng/ml LPS that had been pre-treated with increasing concentrations of SP4. After incubation for 20 hours, the concentration IL-12p40 in the supernatant was measured with an ELISA.

To obtain some information on the inflammatory process, the ability of SP4 to neutralize LPS using the whole blood assay and IL-12p40 production as read-out was measured. The results (FIG. 8) indicate that at a concentration of 100 nM SP4 neutralizes LPS by 74%, and at 1000 nM SP4 almost completely (96%) as compared to the LPS control.

Selective Killing of Cancer Cells by SP4 and SP27

To obtain some data on the selective carcinoma toxic activity of the snake-derived peptides, it was determined that the cytotoxic effects of increasing does of SP4 and SP27 on normal human melanocytes and 4 melanoma cell lines using the LDH release assay. The results indicate that at a dose of 51.2 μM SP4 and SP27 did not affect the viability of normal melanocytes, but exerted a significant toxic effect on the melanoma cells.

CONCLUSION

The threat of infections that cannot be effectively treated with antibiotics and the associated need for novel agents to combat such infections are widely acknowledged. For the development of such novel agents, two candidates were selected from a panel of 35 synthetic snake cathelicidins based on the following findings. First, the selected snake peptides (SP) 4 and 27 are highly efficient in killing a multidrug resistant (MDR) *S. aureus* and a MDR *P. aeruginosa* strain in vitro without being toxic to human erythrocytes. The selectivity index, i.e., the ratio between the highest non-toxic concentration of the peptide and the lowest concentration of the peptide resulting in 99.9% reduction of an inoculum of about 1 million bacteria (the lethal concentration 99.9 or LC99.9), amounted to 64 and 512 for SP4 and to 16 and 128 for SP27 for MDR *S. aureus* and *P. aeruginosa*, respectively. This data indicates an excellent therapeutic window. Second, in biologically relevant in vitro conditions, i.e., 50% v/v human plasma or urine, these snake peptides were highly effective against MDR strains of the ESKAPE panel and colistin resistant *E. coli*. Third, SP4 and SP27 induced limited resistance in *S. aureus* compared to the antibiotics ciprofloxacin and rifampicin.

As the biofilm is the main life-stage of many (MDR) bacteria and the majority of clinical infections are biofilm-associated infections, the preliminary observations made that a 2-hour exposure to SP4 and SP27 is effective in degrading MDR *A. baumannii* biofilms, but less effective against MRSA biofilms, are of clinical relevance. As SP4 and SP27 are effective in killing bacteria in BM2 medium, the finding that these peptides prevent biofilm formation may be attributed to the killing of the bacteria before they may form a biofilm. Another important aspect of the successful treatment of biofilms concerns activity against persisters, i.e., bacterial cells in a dormant state with a high tolerance to antibiotics. It was revealed that SP4 is highly effective against persisters originating from matured, antibiotic-exposed, MRSA biofilms. Furthermore, it was have found that SP4 in vitro may neutralize the bacterial endotoxin lipopolysaccharide (LPS), indicating that this peptide may affect the inflammatory reaction at the site of infection.

Most of the snake peptides were more effective against MDR *P. aeruginosa* than against MDR *S. aureus*. In agreement, the gram-negative bacteria within the ESKAPE panel were more susceptible to SP4 and SP27 than the gram-positive bacteria, confirming that snake peptides display selective efficacy to (MDR) gram negative bacteria. Of note, SP18 was not effective against *S. aureus* (LC99.9>102.4 μM), while being highly effective against MDR *P. aeruginosa* (LC99.9 of 0.8 μM). Unfortunately, an explanation for this difference in susceptibility to snake peptides between gram-negative and gram-positive bacteria cannot be provided. As cathelicidins with their positively charged face interact with negatively charged plasma membrane constituents differences in the plasma membrane and other cell wall components of gram-negative and gram-positive bacteria may play an important role. Biophysical experiments with artificial bacterial membranes and molecular dynamics may be instrumental in understanding why snake peptides selective affect gram-negative bacteria. Interestingly, gram-negative rods are overrepresented in the oral flora of (non-poisonous) snakes (Shek et al., 2009). Thus, it may be speculated that snakes produce peptides that are highly effective against the gram-negative bacteria to control bacterial growth in the oral cavities. Anyhow, the selectivity of the snake peptides may be advantageous for the treatment of infections with gram negative bacteria not responding to current antibiotics.

Several peptides in the snake peptide panel have been reported earlier by others. CATHPb1 and CATHPb3 found in *Phyton bivittatus* are identical to SP15 and SP16 (Cai et al., 2018). Comparison of the activities of SP15 and CATHPb1 revealed that they were significantly less effective against MRSA than against *P. aeruginosa*, while SP16 and CATPb3 both exerted no bactericidal effect against MRSA and *P. aeruginosa*. Whereas SP15 and SP16 showed no toxicity against erythrocytes (still safe around 800 μg/ml), CATHPb1 and CATHPb3 showed 6.63% and 9.14% hemolysis at 100 μg/ml, respectively. This difference in hemolytic activity may be attributed to the presence of 50% v/v human plasma in the experiments disclosed herein as opposed to PBS alone. Another peptide, i.e., SP13, is similar to OH-CATH30, a peptide from the king cobra only four amino acids shorter than SP13 (Zhao et al., 2018). SP13 shows a slightly higher bactericidal activity than OH-CATH30 against MRSA, i.e., an LC99.9 of 24.5 mg/ml (5.9 μM) for SP13 compared to a MIC90 of 32 mg/ml for OH-CATH30. The latter peptide seems to be more toxic than SP13 (70% hemolysis at 250 μg/ml for OH-CATH30 and <5% at 851 μg/ml for SP4). It would be interesting to see if this difference is related to the additional four amino acids in OH-CATH30. Furthermore, similar data on the bactericidal activity of SP2 (identical to crotalicidin) and SP3 (identical to bathroxicidin) have been reported by others (Falcao C. B. et al., 2014). Surprisingly, these authors reported the sequence of SP4 (identical to lutztcidin) and SP9 (identical to lachesicidin) without any functional activities.

The finding that snake peptides displayed low toxicity against human erythrocytes indicates that they may be considered for systemic application. Another important finding pertains to the ability of SP4 and SP27 to eliminate MRSA from ex vivo human skin. Preliminary experiments revealed that already, within a 1-hour exposure, these peptides eliminated the bacteria from intact human skin in a dose-dependent fashion with SP4 being slightly more effective than SP27.

Experiments will be performed to confirm the effects of the peptides disclosed herein on wounded ex vivo skin models colonized by gram-positive and gram-negative bacteria as well as wounded ex vivo human skin with a biofilm. Furthermore, multiple exposure durations will be performed. These models are useful to determine the effects of the peptides on the wound healing process. The peptides will be tested as an ointment for topical application on wounds.

Finally, Wang et al. have reported that the snake cathelicidin BF30 (identical to SP5) inhibits melanoma cells and other cancer cells in vitro and reduces the tumor load in melanoma-bearing mice. In this connection, it was found that SP4 and SP27 is toxic to melanoma cells at concentrations that are safe for primary human melanocytes, indicating that these peptides may be candidates for the treatment of melanomas and other cancers.

TABLE 1

Figure 10:
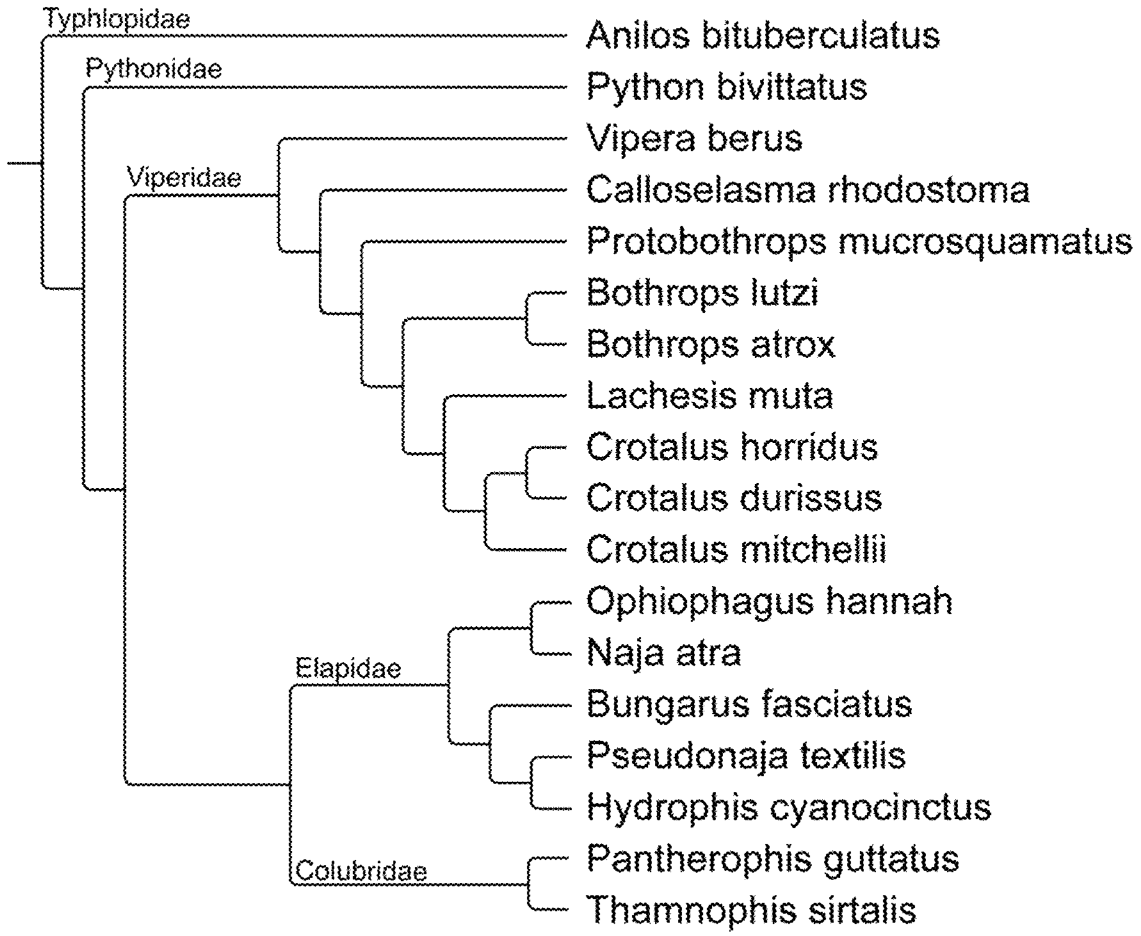
FIG. 10: Phylogenetic tree of the snake species described in examples.

Bactericidal effect on MDR *S. aureus* and *P. aeruginosa* and cytotoxic effect of snake peptides. The bactericidal activity of the snake peptides on MDR *S. aureus* (LUH 14616) and MDR *P. aeruginosa* (LUH 15103) was determined after a 2-hour treatment in the presence of 50% v/v human plasma. Bactericidal activity is expressed as the LC99.9, i.e., the lowest concentration of peptide that kills ≥99.9% of the bacteria. Results are medians (and range) of three to thirteen independent experiments, each in duplicate. If no range is shown the LC99.9 did not differ between the experiments or the peptide is tested once. Toxic effect of the peptides was assessed by exposing human erythrocytes to increasing peptide concentrations for 1 hour in the presence of human plasma. Results are expressed as the highest peptide concentration that resulted in <5% erythrocyte lysis as compared to the positive control triton-X. Snake species sorted by phylogenetic tree (FIG. 10).

| Species | Peptide | Alternative name in literature | LC99.9 (μM) MRSA in 50% plasma | LC99.9 (μM) MDR *P. aeruginosa* in 50% plasma | Hemolysis (μM) in 50% plasma |
|---|---|---|---|---|---|
| *Anilos bituberculatus* | SP27 | | 6.4 (3.2-6.4) | 0.8 (0.2-1.6) | 102.4 |
| *Python bivittatus* | SP15 | CATHPb1 | 12.8 | 0.8 | 204.8 |
| | SP16 | CATHPb3 | >102.4 | >102.4 | 204.8 |
| *Calloselasma* | SP14 | | 12.8 | 0.4 | 204.8 |
| *rhodostoma* | SP21 | | >102.4 | >102.4 | 204.8 |
| *Protobothrops* | SP23 | | 4.8 (3.2-6.4) | 0.2 | 204.8 |
| *mucrosquamatus* | SP33 | | >102.4 | >102.4 | 204.8 |
| *Bothrops lutzi* | SP4 | Lutzicidin | 3.2 (3.2-12.8 | 0.4 (0.2-16) | 204.8 |
| *Bothrops atrox* | SP3 | Batroxicidin | 3.2 | 0.8 | 204.8 |
| *Lachesis muta* | SP9 | Lachesicidin | 51.2 (25.6-51.2) | 1.6 | 204.8 |
| *Crotalus horridus* | SP34 | | >102.4 | >102.4 | 204.8 |
| *Crotalus durissus* | SP2 | Crotalicidin | 25.6 | 0.4 | 204.8 |
| | SP6 | | 57.6 (12.8-102.4) | 0.4 | 204.8 |
| | SP7 | | 38.4 (25.6-51.2) | 0.8 | 204.8 |
| *Crotalus mitchellii* | SP25 | | 12.8 | 0.4 | 102.4 |
| | SP26 | | >102.4 | 12.8 | 102.4 |
| *Ophiophagus hannah* | SP1 | OH-CATH | >102.4 | 3.2 | 51.2 |
| | SP13 | | 5.9 (1.6-12.3) | 0.4 | 204.8 |
| | SP17 | | >102.4 | >102.4 | 51.2 |
| | SP18 | | 102.4 | 0.8 | 204.8 |
| | SP19 | | >102.4 | 12.8 | 204.8 |
| | SP20 | | >102.4 | >102.4 | 204.8 |
| *Naja atra* | SP10 | | 16 (6.4-15.6) | 0.8 | 204.8 |
| *Bungarus fasciatus* | SP5 | Bf-CRAMP/ BF-30 | 25.6 | 0.4 | 204.8 |
| *Pseudonaja textillis* | SP11 | | 3.2 | 0.4 | 204.8 |
| | SP12 | | 25.6 (12.8->102.4) | 3.2 | 51.2 |
| *Hydrophis cyanocinctus* | SP8 | | 25.6 | 1.6 | 102.4 |
| *Pantherophis guttatus* | SP28 | | 51.2 | 6.4 | 204.8 |
| | SP29 | | >102.4 | 51.2 | 102.4 |
| | SP30 | | 51.2 | 2.4 (1.6-3.2) | 204.8 |
| | SP35 | | 51.2 | 1.6 | 204.8 |
| *Thamnophis sirtalis* | SP22 | | 102.4 | 51.2 | 102.4 |
| | SP24 | | 6.4 | 1.6 | 102.4 |
| | SP31 | | 102.4 | 25.6 | 102.4 |
| | SP32 | | 25.6 | 12.8 | 102.4 |

TABLE 2

Bactericidal effect on MDR *S. aureus* by shortened versions of SP4. The peptide SP4 and its shortened versions from either the N-terminus or C-terminus were screened for bactericidal activity against MDR *S. aureus* in 50% v/v humane plasma. The results are expressed as the concentration that induced a 3 log reduction of viable bacteria compared to the control (0 μM).

| Peptide | Number of amino acids shortened at N terminus | Number of amino acids shortened at C terminus | LC99.9 (μM) |
|---|---|---|---|
| SP4 | 0 | 0 | 3.2 |
| SP4-1 | 0 | 1 | 3.2 |
| SP4-2 | 1 | 0 | 3.2 |
| SP4-3 | 0 | 2 | 3.2 |
| SP4-4 | 1 | 1 | 3.2 |
| SP4-5 | 2 | 0 | 6.4 |
| SP4-6 | 0 | 3 | 32 |
| SP4-7 | 1 | 2 | 4.8 |
| SP4-8 | 2 | 1 | 12.8 |

TABLE 2-continued

Bactericidal effect on MDR *S. aureus* by shortened versions of SP4. The peptide SP4 and its shortened versions from either the N-terminus or C-terminus were screened for bactericidal activity against MDR *S. aureus* in 50% v/v humane plasma. The results are expressed as the concentration that induced a 3 log reduction of viable bacteria compared to the control (0 μM).

| Peptide | Number of amino acids shortened at N terminus | Number of amino acids shortened at C terminus | LC99.9 (μM) |
|---|---|---|---|
| SP4-9 | 3 | 0 | 25.6 |
| SP4-10 | 0 | 4 | 12.8 |
| SP4-11 | 1 | 3 | 38.4 |
| SP4-12 | 2 | 2 | 51.2 |
| SP4-13 | 3 | 1 | 76.8 |
| SP4-14 | 4 | 0 | 51.2 |
| SP4-15 | 0 | 5 | 102.4 |
| SP4-16 | 1 | 4 | 64 |
| SP4-17 | 2 | 3 | 51.2 |

TABLE 2-continued

Bactericidal effect on MDR *S. aureus* by shortened versions of SP4. The peptide SP4 and its shortened versions from either the N-terminus or C-terminus were screened for bactericidal activity against MDR *S. aureus* in 50% v/v humane plasma. The results are expressed as the concentration that induced a 3 log reduction of viable bacteria compared to the control (0 μM).

| Peptide | Number of amino acids shortened at N terminus | Number of amino acids shortened at C terminus | LC99.9 (μM) |
|---|---|---|---|
| SP4-18 | 3 | 2 | 19.2 |
| SP4-19 | 4 | 1 | 38.4 |
| SP4-20 | 5 | 0 | 6.4 |
| SP4-21 | 0 | 6 | 12.8 |
| SP4-22 | 1 | 5 | 38.4 |
| SP4-23 | 2 | 4 | 19.2 |
| SP4-24 | 3 | 3 | >102.4 |
| SP4-25 | 4 | 2 | 38.4 |
| SP4-26 | 5 | 1 | 76.8 |
| SP4-27 | 6 | 0 | 38.4 |
| SP4-28 | 0 | 7 | 25.6 |
| SP4-29 | 1 | 6 | 12.8 |
| SP4-30 | 2 | 5 | 64 |
| SP4-31 | 3 | 4 | 102.4 |
| SP4-32 | 4 | 3 | 76.8 |
| SP4-33 | 5 | 2 | 19.2 |
| SP4-34 | 6 | 1 | 51.2 |
| SP4-35 | 7 | 0 | 32 |
| SP4-36 | 0 | 8 | 9.6 |
| SP4-37 | 1 | 7 | 12.8 |
| SP4-38 | 2 | 6 | 12.8 |
| SP4-39 | 3 | 5 | 76.8 |
| SP4-40 | 4 | 4 | >102.4 |
| SP4-41 | 5 | 3 | >102.4 |
| SP4-42 | 6 | 2 | >102.4 |
| SP4-43 | 7 | 1 | >102.4 |
| SP4-44 | 8 | 0 | 51.2 |
| SP4-45 | 0 | 9 | 19.2 |
| SP4-46 | 1 | 8 | 28.8 |
| SP4-47 | 2 | 7 | 19.2 |

TABLE 2-continued

Bactericidal effect on MDR *S. aureus* by shortened versions of SP4. The peptide SP4 and its shortened versions from either the N-terminus or C-terminus were screened for bactericidal activity against MDR *S. aureus* in 50% v/v humane plasma. The results are expressed as the concentration that induced a 3 log reduction of viable bacteria compared to the control (0 μM).

| Peptide | Number of amino acids shortened at N terminus | Number of amino acids shortened at C terminus | LC99.9 (μM) |
|---|---|---|---|
| SP4-48 | 3 | 6 | 102.4 |
| SP4-49 | 4 | 5 | >102.4 |
| SP4-50 | 5 | 4 | >102.4 |
| SP4-51 | 6 | 3 | >102.4 |
| SP4-52 | 7 | 2 | >102.4 |
| SP4-53 | 8 | 1 | >102.4 |
| SP4-54 | 9 | 0 | 102.4 |
| SP4-55 | 0 | 10 | 19.2 |
| SP4-56 | 1 | 9 | 19.2 |
| SP4-57 | 2 | 8 | 25.6 |
| SP4-58 | 3 | 7 | 51.2 |
| SP4-59 | 4 | 6 | 38.4 |
| SP4-60 | 5 | 5 | 51.2 |
| SP4-61 | 6 | 4 | >102.4 |
| SP4-62 | 7 | 3 | >102.4 |
| SP4-63 | 8 | 2 | 102.4 |
| SP4-64 | 9 | 1 | >102.4 |
| SP4-65 | 10 | 0 | >102.4 |

Example 2— Alanine Scan

The amino acids of the SP27 peptide were substituted at various positions with Alanine. The substituted peptides were tested on *A. baumannii* and *E. coli* bacterial strains for having antimicrobial activity. Furthermore, the substituted peptides were tested for their hemolytic activity as an indicator for their toxicity.

TABLE 3

Alanine scan

LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. *A. baumannii* is the multidrug resistant strain *Acinetobacter baumannii* RUH875; *E. coli* is the drug-sensitive strain *Escherichia coli* LUH15108. Substituted alanines are underlined.

| Peptide | LC99.9 (μM) *A. baumannii* | LC99.9 (μM) *E. coli* | Toxicity (μM) | Sequence |
|---|---|---|---|---|
| SP27 | 0.8 | 1.6 | 102.4 | K R F K K F F R K V K K G V H R Y F K K N K F Y I A A T I P Y Y G |
| SP27-1 | 1.6 | 1.6 | 102.4 | **A** R F K K F F R K V K K G V H R Y F K K N K F Y I A A T I P Y Y G |
| SP27-2 | 0.8 | 1.6 | 102.4 | K **A** F K K F F R K V K K G V H R Y F K K N K F Y I A A T I P Y Y G |
| SP27-3 | 0.8 | 1.6 | 102.4 | K R **A** K K F F R K V K K G V H R Y F K K N K F Y I A A T I P Y Y G |
| SP27-4 | 1.6 | 1.6 | ≥204.8 | K R F **A** K F F R K V K K G V H R Y F K K N K F Y I A A T I P Y Y G |
| SP27-5 | 1.6 | 3.2 | ≥204.8 | K R F K **A** F F R K V K K G V H R Y F K K N K F Y I A A T I P Y Y G |
| SP27-6 | 0.4 | 1.6 | 102.4 | K R F K K **A** F R K V K K G V H R Y F K K N K F Y I A A T I P Y Y G |
| SP27-7 | 0.4 | 2.6 | ≥204.8 | K R F K K F **A** R K V K K G V H R Y F K K N K F Y I A A T I P Y Y G |
| SP27-8 | 0.8 | 1.6 | ≥204.8 | K R F K K F F **A** K V K K G V H R Y F K K N K F Y I A A T I P Y Y G |
| SP27-9 | 1.6 | 1.6 | 182.4 | K R F K K F F R **A** V K K G V H R Y F K K N K F Y I A A T I P Y Y G |
| SP27-10 | 0.4 | 1.6 | ≥204.8 | K R F K K F F R K **A** K K G V H R Y F K K N K F Y I A A T I P Y Y G |
| SP27-11 | 1.6 | 2.6 | 102.4 | K R F K K F F R K V **A** K G V H R Y F K K N K F Y I A A T I P Y Y G |
| SP27-12 | 0.8 | 1.6 | 102.4 | K R F K K F F R K V K **A** G V H R Y F K K N K F Y I A A T I P Y Y G |
| SP27-13 | 1.6 | 1.6 | 102.4 | K R F K K F F R K V K K **A** V H R Y F K K N K F Y I A A T I P Y Y G |
| SP27-14 | 0.8 | 1.6 | ≥204.8 | K R F K K F F R K V K K G **A** H R Y F K K N K F Y I A A T I P Y Y G |
| SP27-15 | 3.2 | 3.2 | ≥204.8 | K R F K K F F R K V K K G V **A** R Y F K K N K F Y I A A T I P Y Y G |
| SP27-16 | 0.8 | 1.6 | 202.4 | K R F K K F F R K V K K G V H **A** Y F K K N K F Y I A A T I P Y Y G |
| EP27-17 | 0.8 | 1.6 | ≥204.8 | K R F K K F F R K V K K G V H R **A** F K K N K F Y I A A T I P Y Y G |
| SP27-18 | 0.8 | 1.6 | ≥204.8 | K R F K K F F R K V K K G V H R Y **A** K K N K F Y I A A T I P Y Y G |
| SP27-19 | 0.8 | 1.6 | 102.4 | K R F K K F F R K V K K G V H R Y F **A** K N K F Y I A A T I P Y Y G |
| SP27-20 | 0.8 | 1.6 | 102.4 | K R F K K F F R K V K K G V H R Y F K **A** N K F Y I A A T I P Y Y G |
| SP27-21 | 8.8 | 1.6 | 51.2 | K R F K K F F R K V K K G V H R Y F K K **A** K F Y I A A T I P Y Y G |
| SP27-22 | 1.6 | 1.6 | ≥204.8 | K R F K K F F R K V K K G V H R Y F K K N **A** F Y I A A T I P Y Y G |
| SP27-23 | 0.4 | 1.6 | ≥204.8 | K R F K K F F R K V K K G V H R Y F K K N K **A** Y I A A T I P Y Y G |
| SP27-24 | 3.8 | 0.8 | ≥204.8 | K R F K K F F R K V K K G V H R Y F K K N K F **A** I A A T I P Y Y G |
| SP27-25 | 1.6 | 1.6 | ≥204.8 | K R F K K F F R K V K K G V H R Y F K K N K F Y **A** A A T I P Y Y G |
| SP27-26 | 0.8 | 1.6 | 102.4 | K R F K K F F R K V K K G V H R Y F K K N K F Y I A A **A** I P Y Y G |
| SP27-27 | 0.8 | 1.6 | ≥204.8 | K R F K K F F R K V K K G V H R Y F K K N K F Y I A A T **A** P Y Y G |
| SP27-28 | 0.8 | 0.8 | 25.6 | K R F K K F F R K V K K G V H R Y F K K N K F Y I A A T I **A** Y Y G |
| SP27-29 | 1.6 | 1.6 | ≥204.8 | K R F K K F F R K V K K G V H R Y F K K N K F Y I A A T I P **A** Y G |
| SP27-30 | 0.8 | 1.6 | ≥204.8 | K R F K K F F R K V K K G V H R Y F K K N K F Y I A A T I P Y **A** G |
| SP27-31 | 0.8 | 3.6 | ≥204.8 | K R F K K F F R K V K K G V H R Y F K K N K F Y I A A T I P Y Y **A** |

Example 3— D-Amino Acid Substitutions

The amino acids of the SP27 peptide were substituted at various positions with the corresponding D-amino acid. In addition, a peptide containing all D-amino acids and a retro-inverse of SP27 were synthesized. The substituted peptides were tested on an *A. baumannii* bacterial strain for having antimicrobial activity. Furthermore, the substituted peptides were tested for their hemolytic activity as an indicator for their toxicity. The results for antimicrobial activity and toxicity of the modified peptides are shown in Table 4.

TABLE 4

D-amino acid substitutions
LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. *A. baumannii* is the multidrug resistant strain *Acinetobacter baumannii* RUH875. L-amino acids in capital letters and D-amino acids in small letters and underlined.

| Peptide | LC99.9 (μM) *A. baumannii* | Toxicity (μM) | Sequence | | | | | | | | | | | | | | | | |
|---|---|---|---|---|---|---|---|---|---|---|---|---|---|---|---|---|---|---|---|
| SP27 | 0.8 | 102.4 | K | R | F | K | K | F | F | R | K | V | K | K | G | V | H | R | Y |
| SP27-RI | 6.4 | 51.2 | G | y | y | p | i | t | a | a | i | y | f | k | n | k | k | f | y |
| SP27-D | 1.6 | 51.2 | k | r | f | k | k | f | f | r | k | v | k | k | G | v | h | r | y |
| SP27-32 | 0.8 | 51.2 | **k** | R | F | K | K | F | F | R | K | V | K | K | G | V | H | R | Y |
| SP27-33 | 0.8 | 102.4 | K | **r** | F | K | K | F | F | R | K | V | K | K | G | V | H | R | Y |
| SP27-34 | 0.8 | 102.4 | K | R | **f** | K | K | F | F | R | K | V | K | K | G | V | H | R | Y |
| SP27-35 | 1.6 | 102.4 | K | R | F | **k** | K | F | F | R | K | V | K | K | G | V | H | R | Y |
| SP27-36 | 0.8 | ≥204.8 | K | R | F | K | **k** | F | F | R | K | V | K | K | G | V | H | R | Y |
| SP27-37 | 0.8 | ≥204.8 | K | R | F | K | K | **f** | F | R | K | V | K | K | G | V | H | R | Y |
| SP27-38 | 0.8 | 102.4 | K | R | F | K | K | F | **f** | R | K | V | K | K | G | V | H | R | Y |
| SP27-39 | 0.8 | 102.4 | K | R | F | K | K | F | F | **r** | K | V | K | K | G | V | H | R | Y |
| SP27-40 | 0.4 | ≥204.8 | K | R | F | K | K | F | F | R | **k** | V | K | K | G | V | H | R | Y |
| SP27-41 | 0.8 | ≥204.8 | K | R | F | K | K | F | F | R | K | **v** | K | K | G | V | H | R | Y |
| SP27-42 | 0.8 | ≥204.8 | K | R | F | K | K | F | F | R | K | V | **k** | K | G | V | H | R | Y |
| SP27-43 | 0.3 | 53.2 | K | R | F | K | K | F | F | R | K | V | K | **k** | G | V | H | R | Y |
| SP27-44 | 1.6 | ≥204.8 | K | R | F | K | K | F | F | R | K | V | K | K | G | **v** | H | R | Y |
| SP27-45 | 0.8 | 102.4 | K | R | F | K | K | F | F | R | K | V | K | K | G | V | **h** | R | Y |
| SP27-46 | 1.6 | 51.2 | K | R | F | K | K | F | F | R | K | V | K | K | G | V | H | **r** | Y |
| SP27-47 | 1.6 | 51.2 | K | R | F | K | K | F | F | R | K | V | K | K | G | V | H | R | **y** |
| SP27-48 | 1.6 | 204.8 | K | R | F | K | K | F | F | R | K | V | K | K | G | V | H | R | Y |
| SP27-49 | 0.8 | ≥204.8 | K | R | F | K | K | F | F | R | K | V | K | K | G | V | H | R | Y |
| SP27-50 | 0.8 | 102.4 | K | R | F | K | K | F | F | R | K | V | K | K | G | V | H | R | Y |
| SP27-51 | 0.8 | 102.4 | K | R | F | K | K | F | F | R | K | V | K | K | G | V | H | R | Y |
| SP27-52 | 0.4 | ≥204.8 | K | R | F | K | K | F | F | R | K | V | K | K | G | V | H | R | Y |
| SP27-53 | 0.4 | ≥204.8 | K | R | F | K | K | F | F | R | K | V | K | K | G | V | H | R | Y |
| SP27-54 | 0.4 | 53.2 | K | R | F | K | K | F | F | R | K | V | K | K | G | V | H | R | Y |
| SP27-55 | 0.8 | 51.2 | K | R | F | K | K | F | F | R | K | V | K | K | G | V | H | R | Y |
| SP27-56 | 0.4 | 51.2 | K | R | F | K | K | F | F | R | K | V | K | K | G | V | H | R | Y |
| SP27-57 | 0.8 | 51.2 | K | R | F | K | K | F | F | R | K | V | K | K | G | V | H | R | Y |
| SP27-58 | 0.8 | ≥204.3 | K | R | F | K | K | F | F | R | K | V | K | K | G | V | H | R | Y |
| SP27-59 | 0.8 | 51.2 | K | R | F | K | K | F | F | R | K | V | K | K | G | V | H | R | Y |
| SP27-60 | 0.8 | 51.2 | K | R | F | K | K | F | F | R | K | V | K | K | G | V | H | R | Y |
| SP27-61 | 1.6 | 51.2 | K | R | F | K | K | F | F | R | K | V | K | K | G | V | H | R | Y |
| SP27-62 | 0.8 | 51.2 | K | R | F | K | K | F | F | R | K | V | K | K | G | V | H | R | Y |

| Peptide | Sequence | | | | | | | | | | | | | | |
|---|---|---|---|---|---|---|---|---|---|---|---|---|---|---|---|
| SP27 | F | K | K | N | K | F | Y | I | A | A | T | I | P | Y | Y | G |
| SP27-RI | r | h | v | G | k | k | v | k | r | f | f | k | k | f | r | k |
| SP27-D | f | k | k | n | k | f | y | i | a | a | t | i | p | y | y | G |
| SP27-32 | F | K | K | N | K | F | Y | I | A | A | T | I | P | Y | Y | G |
| SP27-33 | F | K | K | N | K | F | Y | I | A | A | T | I | P | Y | Y | G |
| SP27-34 | F | K | K | N | K | F | Y | I | A | A | T | I | P | Y | Y | G |
| SP27-35 | F | K | K | N | K | F | Y | I | A | A | T | I | P | Y | Y | G |
| SP27-36 | F | K | K | N | K | F | Y | I | A | A | T | I | P | Y | Y | G |
| SP27-37 | F | K | K | N | K | F | Y | I | A | A | T | I | P | Y | Y | G |
| SP27-38 | F | K | K | N | K | F | Y | I | A | A | T | I | P | Y | Y | G |
| SP27-39 | F | K | K | N | K | F | Y | I | A | A | T | I | P | Y | Y | G |
| SP27-40 | F | K | K | N | K | F | Y | I | A | A | T | I | P | Y | Y | G |
| SP27-41 | F | K | K | N | K | F | Y | I | A | A | T | I | P | Y | Y | G |
| SP27-42 | F | K | K | N | K | F | Y | I | A | A | T | I | P | Y | Y | G |
| SP27-43 | F | K | K | N | K | F | Y | I | A | A | T | I | P | Y | Y | G |
| SP27-44 | F | K | K | N | K | F | Y | I | A | A | T | I | P | Y | Y | G |
| SP27-45 | F | K | K | N | K | F | Y | I | A | A | T | I | P | Y | Y | G |
| SP27-46 | F | K | K | N | K | F | Y | I | A | A | T | I | P | Y | Y | G |
| SP27-47 | F | K | K | N | K | F | Y | I | A | A | T | I | P | Y | Y | G |
| SP27-48 | **f** | K | K | N | K | F | Y | I | A | A | T | I | P | Y | Y | G |
| SP27-49 | F | **k** | K | N | K | F | Y | I | A | A | T | I | P | Y | Y | G |
| SP27-50 | F | K | **k** | N | K | F | Y | I | A | A | T | I | P | Y | Y | G |
| SP27-51 | F | K | K | **n** | K | F | Y | I | A | A | T | I | P | Y | Y | G |

TABLE 4-continued

D-amino acid substitutions
LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. *A. baumannii* is the multidrug resistant strain *Acinetobacter baumannii* RUH875. L-amino acids in capital letters and D-amino acids in small letters and underlined.

| | | | | | | | | | | | | | | | | |
|---|---|---|---|---|---|---|---|---|---|---|---|---|---|---|---|---|
| SP27-52 | F | K | K | N | **k** | F | Y | I | A | A | T | I | P | Y | Y | G |
| SP27-53 | F | K | K | N | K | **f** | Y | I | A | A | T | I | P | Y | Y | G |
| SP27-54 | F | K | K | N | K | F | **y** | I | A | A | T | I | P | Y | Y | G |
| SP27-55 | F | K | K | N | K | F | Y | **i** | A | A | T | I | P | Y | Y | G |
| SP27-56 | F | K | K | N | K | F | Y | I | **a** | A | T | I | P | Y | Y | G |
| SP27-57 | F | K | K | N | K | F | Y | I | A | **a** | T | I | P | Y | Y | G |
| SP27-58 | F | K | K | N | K | F | Y | I | A | A | **t** | I | P | Y | Y | G |
| SP27-59 | F | K | K | N | K | F | Y | I | A | A | T | **i** | P | Y | Y | G |
| SP27-60 | F | K | K | N | K | F | Y | I | A | A | T | I | **p** | Y | Y | G |
| SP27-61 | F | K | K | N | K | F | Y | I | A | A | T | I | P | **y** | Y | G |
| SP27-62 | F | K | K | N | K | F | Y | I | A | A | T | I | P | Y | **y** | G |

Example 4— Length Variations

Shorter variants of the SP27 peptide were tested for their antimicrobial activity on an *A. baumannii* bacterial strain. In this test, both N-terminally and C-terminally amino acids of the SP27 peptide were deleted. Furthermore, the substituted peptides were tested for their hemolytic activity as an indicator for their toxicity.

TABLE 5 length variations
LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour. *A. baumannii* is the multidrug resistant strain *Acinetobacter baumannii* RUH875.

| Peptide | LC99.9 (μM) *A. baumannii* | Toxicity (μM) | Sequence | | | | | | | | | | | | | | | | |
|---|---|---|---|---|---|---|---|---|---|---|---|---|---|---|---|---|---|---|---|
| SP27 | 0.8 | 102.4 | K | R | F | K | K | F | F | R | K | V | K | K | G | V | H | R | Y |
| SP27-63 | 0.4 | ≥409.6 | K | R | F | K | K | F | F | R | K | V | K | K | G | V | H | R | Y |
| SP27-64 | 0.8 | 204.8 | | R | F | K | K | F | F | R | K | V | K | K | G | V | H | R | Y |
| SP27-65 | 1.6 | 204.8 | | | F | K | K | F | F | R | K | V | K | K | G | V | H | R | Y |
| SP27-66 | 1.6 | ≥409.6 | | | | K | K | F | F | R | K | V | K | K | G | V | H | R | Y |
| SP27-67 | 3.2 | ≥409.6 | | | | | K | F | F | R | K | V | K | K | G | V | H | R | Y |
| SP27-68 | 12.8 | 204.8 | | | | | | F | F | R | K | V | K | K | G | V | H | R | Y |
| SP27-69 | 25.6 | 409.6 | | | | | | | F | R | K | V | K | K | G | V | H | R | Y |
| SP27-70 | 12.8 | ≥408.6 | | | | | | | | R | K | V | K | K | G | V | H | R | Y |
| SP27-71 | 12.8 | 204.8 | | | | | | | | | K | V | K | K | G | V | H | R | Y |
| SP27-72 | 25.6 | 204.8 | | | | | | | | | | V | K | K | G | V | H | R | Y |

| Peptide | Sequence | | | | | | | | | | | | | | | |
|---|---|---|---|---|---|---|---|---|---|---|---|---|---|---|---|---|
| SP27 | F | K | K | N | K | F | Y | I | A | A | T | I | P | Y | Y | G |
| SP27-63 | F | K | K | N | K | F | Y | | | | | | | | | |
| SP27-64 | F | K | K | N | K | F | Y | I | | | | | | | | |
| SP27-65 | F | K | K | N | K | F | Y | I | A | | | | | | | |
| SP27-66 | F | K | K | N | K | F | Y | I | A | A | | | | | | |
| SP27-67 | F | K | K | N | K | F | Y | I | A | A | T | | | | | |
| SP27-68 | F | K | K | N | K | F | Y | I | A | A | T | I | | | | |
| SP27-69 | F | K | K | N | K | F | Y | I | A | A | T | I | P | | | |
| SP27-70 | F | K | K | N | K | F | Y | I | A | A | T | I | P | Y | | |
| SP27-71 | F | K | K | N | K | F | Y | I | A | A | T | I | P | Y | Y | |
| SP27-72 | F | K | K | N | K | F | Y | I | A | A | T | I | P | Y | Y | G |

Example 5— Peptides that are N-Terminally or C-Terminally Modified with a Polyethylene Glycol (PEG) Group The SP27 peptide was coupled to a Polyethylene glycol (PEG) on either the N-terminal or C-terminal of the peptide Modified amino acid molecules were used to couple the PEG-groups to the peptides. These modified amino acids contain an amine (—NH2) and carboxyl (—COOH) functional group. The amine functional group is protected with an Fmoc-group, which is removed after coupling the PEG-group to the peptide. For this experiment, the following PEG polymer chains were used: PEG2, PEGS, PEGS, PEG11, and PEG27.

Fmoc-NH-(PEG)2-COOH (Merck, CAS 867062-95-1)

Fmoc-NH-(PEG)3-COOH (Merck, CAS 557756-85-1)

Fmoc-NH-(PEG)5-COOH (Merck, CAS 882847-34-9)

Fmoc-NH-(PEG)11-COOH (Polypure, CAS 756526-01-9)

Fmoc-NH-(PEG)27-COOH (Polypure)

The substituted peptides were tested on an *A. baumannii* bacterial strain for having antimicrobial activity. Furthermore, the substituted peptides were tested for their hemolytic activity as an indicator for their toxicity.

TABLE 6

Peptides that are N-terminally or C-terminally modified with a PEG group
LC99.9 is the lowest concentration of the peptide that kills 99.9% of an inoculum of about one million bacteria in the presence of 50% (v/v) human plasma within 2 hours.
Toxicity is expressed as the highest concentration of the peptide that lyses less than 5% of the human erythrocytes in human plasma within 1 hour. A. baumannii is the multidrug resistant strain Acinetobacter baumannii RUH875.
X = PEG is polyethyleneglycol; B = amide

| Peptide | LC99.9 (μM) *A. baumannii* | Toxicity (μM) | Sequence | | | | | | | | | | | | | | | | | |
|---|---|---|---|---|---|---|---|---|---|---|---|---|---|---|---|---|---|---|---|---|
| SP27 | 0.8 | 102.4 | K | R | F | K | K | F | F | R | K | V | K | K | G | V | H | R | Y | F |
| SP27-PEG2 | 3.2 | 204.3 | K | R | F | K | K | F | F | R | K | V | K | K | G | V | H | R | Y | F |
| SP27-PEG3 | 1.6 | 102.4 | K | R | F | K | K | F | F | R | K | V | K | K | G | V | H | R | Y | F |
| SP27-PEG5 | 1.6 | 102.4 | K | R | F | K | K | F | F | R | K | V | K | K | G | V | H | R | Y | F |
| SP27-PEG11 | 1.6 | 204.3 | K | R | F | K | K | F | F | R | K | V | K | K | G | V | H | R | Y | F |
| SP27-PEG27 | 0.8 | ≥409.6 | K | R | F | K | K | F | F | R | K | V | K | K | G | V | H | R | Y | F |
| PEG2-SP27 | 0.8 | 102.4 | X | K | R | F | K | K | F | F | R | K | V | K | K | G | V | H | R | Y |
| PEG3-SP27 | 0.8 | 102.4 | X | K | R | F | K | K | F | F | R | K | V | K | K | G | V | H | R | Y |
| PEG5-SP27 | 0.8 | 102.4 | X | K | R | F | K | K | F | F | R | K | V | K | K | G | V | H | R | Y |
| PEC11-SP27 | 0.9 | 102.4 | X | K | R | F | K | K | F | F | R | K | V | K | K | G | V | H | R | Y |
| PEG27-SP27 | 8.8 | 102.4 | X | K | R | F | K | K | F | F | R | K | V | K | K | G | V | H | R | Y |
| SP27-63 | 0.4 | ≥409.6 | **K** | **R** | **F** | **K** | **K** | **F** | **F** | **R** | **K** | **V** | **K** | **K** | **G** | **V** | **H** | **R** | **Y** | **F** |
| SP27-63-PEG2 | 0.8 | ≥409.6 | K | R | F | K | K | F | F | R | K | V | K | K | G | V | H | R | Y | F |
| SP27-63-PEG3 | 0.8 | ≥409.6 | K | R | F | K | K | F | F | R | K | V | K | K | G | V | H | R | Y | F |
| SP27-63-PEG5 | 1.6 | 409.6 | K | R | F | K | K | F | F | R | K | V | K | K | G | V | H | R | Y | F |
| SP27-63-PEG11 | 3.2 | ≥409.6 | K | R | F | K | K | F | F | R | K | V | K | K | G | V | H | R | Y | F |
| SP27-63-PEG27 | 12.8 | ≥409.6 | K | R | F | K | K | F | F | R | K | V | K | K | G | V | H | R | Y | F |
| PEG2-SP27-63 | 0.4 | ≥409.6 | **X** | K | R | F | K | K | F | F | R | K | V | K | K | G | V | H | R | Y |
| PEG3-SP27-63 | 8.4 | ≥409.6 | **X** | K | R | F | K | K | F | F | R | K | V | K | K | G | V | H | R | Y |
| PEG5-SP27-63 | 0.4 | ≥409.6 | **X** | K | R | F | K | K | F | F | R | K | V | K | K | G | V | H | R | Y |
| PEG11-SP27-63 | 0.8 | ≥409.6 | **X** | K | R | F | K | K | F | F | R | K | V | K | K | G | V | H | R | Y |
| PEG27-SP27-63 | 2.6 | ≥409.6 | **X** | K | R | F | K | K | F | F | R | K | V | K | K | G | V | H | R | Y |

| Peptide | Sequence | | | | | | | | | | | | | | | | |
|---|---|---|---|---|---|---|---|---|---|---|---|---|---|---|---|---|---|
| SP27 | K | K | N | K | F | Y | I | A | A | T | I | P | Y | Y | G | | |
| SP27-PEG2 | K | K | N | K | F | Y | I | A | A | T | I | P | Y | Y | G | **X** | B |
| SP27-PEG3 | K | K | N | K | F | Y | I | A | A | T | I | P | Y | Y | G | **X** | B |
| SP27-PEG5 | K | K | N | K | F | Y | I | A | A | T | I | P | Y | Y | G | **X** | B |
| SP27-PEG11 | K | K | N | K | F | Y | I | A | A | T | I | P | Y | Y | G | **X** | B |
| SP27-PEG27 | K | K | N | K | F | Y | I | A | A | T | I | P | Y | Y | G | **X** | B |
| PEG2-SP27 | F | K | K | N | K | F | Y | I | A | A | T | I | P | Y | Y | G | |
| PEG3-SP27 | F | K | K | N | K | F | Y | I | A | A | T | I | P | Y | Y | G | |
| PEG5-SP27 | F | K | K | N | K | F | Y | I | A | A | T | I | P | Y | Y | G | |
| PEC11-SP27 | F | K | K | N | K | F | Y | I | A | A | T | I | P | Y | Y | G | |
| PEG27-SP27 | F | K | K | N | K | F | Y | I | A | A | T | I | P | Y | Y | G | |
| SP27-63 | **K** | **K** | **N** | **K** | **F** | **Y** | | | | | | | | | | | |
| SP27-63-PEG2 | K | K | N | K | F | Y | **X** | B | | | | | | | | | |
| SP27-63-PEG3 | K | K | N | K | F | Y | **X** | B | | | | | | | | | |
| SP27-63-PEG5 | K | K | N | K | F | Y | **X** | B | | | | | | | | | |
| SP27-63-PEG11 | K | K | N | K | F | Y | **X** | B | | | | | | | | | |
| SP27-63-PEG27 | K | K | N | K | F | Y | **X** | B | | | | | | | | | |
| PEG2-SP27-63 | F | K | K | N | K | F | Y | | | | | | | | | | |
| PEG3-SP27-63 | F | K | K | N | K | F | Y | | | | | | | | | | |
| PEG5-SP27-63 | F | K | K | N | K | F | Y | | | | | | | | | | |
| PEG11-SP27-63 | F | K | K | N | K | F | Y | | | | | | | | | | |
| PEG27-SP27-63 | F | K | K | N | K | F | Y | | | | | | | | | | |

Example 6— Non-Natural Substitutions

The amino acids of the SP27 peptide were substituted at various positions with non-natural amino acids. The substituted peptides were tested on an *A. baumannii* bacterial strain for having antimicrobial activity. Furthermore, the substituted peptides were tested for their hemolytic activity as an indicator for their toxicity.

TABLE 7

Non-natural substitutions
LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour.
*A. baumannii* is the multidrug resistant strain *A. baumannii* RUH875.

| Peptide | LC99.9 (μM) *A. baumannii* | Toxicity (μM) | Sequence | X |
|---|---|---|---|---|
| SP27 | 0.8 | 102.4 | **K R F K K F F R K V K K G V H R Y F K K N K F Y I A A T I P Y Y G** | |
| SP27-73 | 0.8 | 51.2 | X R F K K F F R K V K K G V H R Y F K K N K F Y I A A T I P Y Y G | Homolysine (hLys) |
| SP27-74 | 8.8 | 182.4 | X R F K K F F R K V K K G V H R Y F K K N K F Y I A A T I P Y Y G | s-Methyl lysine (Lys(Me)) |
| SP27-75 | 0.8 | 102.4 | X R F K K F F R K V K K G V H R Y F K K N K F Y I A A T I P Y Y G | s, ε-Dimethyl lysine (Lys(Me)$_2$) |
| SP27-76 | 0.8 | 122.4 | X R F K K F F R K V K K G V H R Y F K K N K F Y I A A T I P Y Y G | s, s, ε-Trimethyl lysine (Lys (Me)$_6$) |
| SP27-77 | 0.8 | 102.4 | X R F K K F F R K V K K G V H R Y F K K N K F Y I A A T I P Y Y G | Ornithine (Orn) |
| SP27-78 | 0.8 | 102.4 | X R F K K F F R K V K K G V H R Y F K K N K F Y I A A T I P Y Y G | 2, 3-Diaminopropanoic acid (Dap) |
| SP27-79 | 0.8 | 102.4 | X R F K K F F R K V K K G V H R Y F K K N K F Y I A A T I P Y Y G | 2,4-Diaminobutanoic acid (Dab) |
| SP27-80 | 0.8 | 102.4 | K R F K K F F R K V K K G V H R Y F K K N K F Y I A A T I P Y Y G | Homoarginine (hArg) |
| SP27-81 | 0.8 | 102.4 | K R F K K F F R K V K K G V H R Y F K K N K F Y I A A T I P Y Y G | Methylarginine (Arg(Me)) |
| SP27-82 | | 102.4 | K R F K K F F R K V K K G V H R Y F K K N K F Y I A A T I P Y Y G | Asym. dimethylarginine (ADMA) |
| SP27-83 | 0.8 | 51.2 | K R F K K F F R K V K K G V H R Y F K K N K F Y I A A T I P Y Y G | Shortend Arg (Agb) |
| SP27-84 | 0.6 | 102.4 | K R F K K F F R K V K K G V H R Y F K K N K F Y I A A T I P Y Y G | Citrulline (Cit) |
| SP27-85 | 0.8 | 51.2 | K R F K K F F R K V K K G V H R Y F K K N K F Y I A A T I P Y Y G | Homophenylalanine (hPhe) |
| SP27-86 | | 102.4 | K R F K K F F R K V K K G V H R Y F K K N K F Y I A A T I P Y Y G | Homotyrosine (hTyr) |
| SP27-87 | 0.8 | ≥204.8 | K R F K K F F R K V K K G V H R Y F K K N K F Y I A A T I P Y Y G | Phenylglycine (Phg) |
| SP27-88 | 0.8 | ≥204.8 | K R F K K F F R K V K K G V H R Y F K K N K F Y I A A T I P Y Y G | 4-Fluorophenylalanine (Phe (4-F)) |
| SP27-89 | 1.6 | 102.4 | K R F K K F F R K V K K G V H R Y F K K N K F Y I A A T I P Y Y G | 4-Chlorophenylalanine (Phe(4-Cl)) |
| SP27-90 | 0.8 | 102.4 | K R F K K F F R K V K K G V H R Y F K K N K F Y I A A T I P Y Y G | 4-Cyanophenylalamine (Phe(4-CN)) |
| SP27-91 | 0.8 | 102.2 | K R F K K F F R K V K K G V H R Y F K K N K F Y I A A T I P Y Y G | 4-Nitrophenylalanine (Phe(4-NO$_2$)) |
| SP27-92 | 1.6 | 102.4 | K R F K K F F R K V K K G V H R Y F K K N K F Y I A A T I P Y Y G | Cyclohexylalanine (Cha) |
| SP27-93 | 0.8 | ≥204.8 | K R F K K F F R K V K K G V H R Y F K K N K F Y I A A T I P Y Y G | Norvaline (Nva) |
| SP27-94 | 1.6 | 51.2 | K R F K K F F R K V K K G V H R Y F K K N K F Y I A A T I P Y Y G | homoleucine (hLeu) |
| SP27-95 | 0.8 | 102.4 | K R F K K F F R K V K K G V H R Y F K K N K F Y I A A T I P Y Y G | Nozleucine (Nle) |
| SP27-96 | 0.8 | 51.2 | K R F K K F F R K V K K G V H R Y F K K N K F Y I A A T I P Y Y G | 2-Aminobutyric acid (Abs) |
| SP27-97 | 0.8 | 51.2 | K R F K K F F R K V K K G V H R Y F K K N K F Y I A A T I P Y Y G | 1-Methylhistidine (His(1-Me) |

TABLE 7-continued

Non-natural substitutions
LC99.9 is the lowest concentration of the peptide that kills 99.9% of an inoculum of about one million bacteria in the presence of 50% (v/v) human plasma within 2 hours. Toxicity is expressed as the highest concentration of the peptide that lyses less than 5% of the human erythrocytes in human plasma within 1 hour.
*A. baumannii* is the multidrug resistant strain *A. baumannii* RUH875.

| Peptide | LC99.9 (μM) *A. baumannii* | Toxicity (μM) | Sequence | X |
|---|---|---|---|---|
| SP27-98 | 0.8 | 51.2 | K R F K K F F R K V K K G V H R Y F K K N K F Y I A A T I P Y Y G | 3-Methylhistidine (His(3-Me) |
| SP27-99 | 0.8 | ≥204.8 | K R F K K F F R K V K K G V H R Y F K K N K F Y I A A T I P Y Y G | O-Methyltyrosine (Tyr(OMe)) |
| SP27-100 | 1.6 | ≥204.8 | K R F K K F F R K V K K G V H R Y F K K N K F Y I A A T I P Y Y G | Homotyrosine (hTyr) |
| SP27-101 | 1.6 | ≥204.8 | K R F K K F F R K V K K G V H R Y F K K N K F Y I A A T I P Y Y G | Homophenylalanine (hPhe) |
| SP27-102 | 0.8 | 204.8 | K R F K K F F R K V K K G V H R Y F K K N K F Y I A A T I P Y Y G | 4-Fluorophenylalanine (Phe(4-F)) |
| SP27-103 | 0.8 | 51.2 | K R F K K F F R K V K K G V H R Y F K K N K F Y I A A T I P Y Y G | 4-Chlorophenylalanine (Phe(4-Cl)) |
| SP27-104 | 0.8 | 102.4 | K R F K K F F R K V K K G V H R Y F K K N K F Y I A A T I P Y Y G | 4-Cyanophenylalanine (Phe(4-CN)) |
| SP27-105 | 0.8 | 102.4 | K R F K K F F R K V K K G V H R Y F K K N K F Y I A A T I P Y Y G | 4-Nitrophenylalanine (Phe(4-$NO_2$)) |
| SP27-106 | 0.8 | ≥204.8 | K R F K K F F R K V K K G V H R Y F K K N K F Y I A A T I P Y Y G | Dihydroxyphenylalanine (DOPA) |
| SP27-107 | 0.8 | 51.2 | K R F K K F F R K V K K G V H R Y F K K N K F Y I A A T I P Y Y G | Norvaline (Nva) |
| SP27-108 | 0.8 | 51.2 | K R F K K F F R K V K K G V H R Y F K K N K F Y I A A T I P Y Y G | Homcleucine (hLeu) |
| SP27-109 | 0.8 | 51.2 | K R F K K F F R K V K K G V H R Y F K K N K F Y I A A T I P Y Y G | Norleucine (Nle) |
| SP27-110 | 0.8 | ≥204.8 | K R F K K F F R K V K K G V H R Y F K K N K F Y I A A T I P Y Y G | 2-Aminobutyric acid (Abu) |
| SP27-111 | 0.8 | 51.2 | K R F K K F F R K V K K G V H R Y F K K N K F Y I A A T I P Y Y G | Hydroxyproline (Hyp) |
| SP27-112 | 0.4 | 51.2 | K R F K K F F R K V K K G V H R Y F K K N K F Y I A A T I P Y Y G | Isonipecotic acid (Isn) |
| SP27-113 | 0.8 | 102.4 | K R F K K F F R K V K K G V H R Y F K K N K F Y I A A T I P Y Y G | Thiaproline (Thz) |

What is claimed is:

1. An isolated, synthetic or recombinant peptide or a pharmaceutically acceptable salt thereof having antimicrobial activity and having between 20-200 amino acids, said peptide comprising:

at least 20 consecutive amino acids of SEQ ID NO:25, and which comprises at least SEQ ID NO:34, wherein the peptide is N-terminally and/or C-terminally modified, and wherein the peptide has no more than 200 amino acids.

2. The isolated, synthetic or recombinant peptide (Currently pharmaceutically acceptable salt thereof of claim 1, wherein the N-terminal and/or C-terminal modification comprises an N-terminal and/or C-terminal polyethylene glycol (PEG), polysaccharide, and/or lipid.

3. A method of using the isolated, synthetic or recombinant peptide or pharmaceutically acceptable salt thereof according to claim 1 for therapy of a subject, wherein the therapy is treatment of the subject for bacterial infection or as a disinfectant, wherein the method comprises administering the peptide to the subject.

4. The method according to claim 3, wherein the treatment is of a bacterial infection caused by a bacteria that is an antibiotic-resistant bacteria, an antibiotic-tolerant bacteria, a persistent bacteria and/or a biofilm.

5. A method of utilizing the isolated, synthetic or recombinant peptide or pharmaceutically acceptable salt thereof of claim 1 to inhibit biofilm formation or to degrade biofilms as an anti-bacterial agent or disinfectant, wherein the method comprises applying the peptide or pharmaceutically acceptable salt thereof so as to inhibit biofilm formation or to degrade a biofilm.

6. A method of using a peptide or pharmaceutically acceptable salt thereof to treat a subject for a bacterial, infection, or as a disinfectant, wherein the method comprises:

administering the peptide or pharmaceutically acceptable salt thereof to the subject, wherein the peptide has antimicrobial activity and has between 20-200 amino acids, and wherein the peptide comprises at least 20 consecutive amino acids of SEQ ID NO:25 and comprises at least the amino acid sequence of SEQ ID NO:34.

7. A method of utilizing a peptide or pharmaceutically acceptable salt thereof to inhibit biofilm formation or to degrade biofilms as an anti-bacterial agent or as a disinfectant, wherein the method comprises:

applying the peptide or pharmaceutically acceptable salt thereof to a biofilm so as to inhibit biofilm formation or to degrade the biofilm, wherein the peptide has antimicrobial activity and has between 20-200 amino acids, and wherein the peptide comprises at least 20 consecutive amino acids of SEQ ID NO:25, which peptide comprises at least the amino acid sequence of SEQ ID NO:34.

8. The isolated, synthetic or recombinant peptide or pharmaceutically acceptable salt thereof according to claim 1, wherein the peptide has been produced synthetically.

9. The isolated, synthetic or recombinant peptide or pharmaceutically acceptable salt thereof according to claim 1, wherein the peptide has been expressed in a mammalian cell, insect cell, plant cell, bacterial cell, or yeast cell.

* * * * *

UNITED STATES PATENT AND TRADEMARK OFFICE

CERTIFICATE OF CORRECTION

PATENT NO. : 12,037,372 B2
APPLICATION NO. : 18/322507
DATED : July 16, 2024
INVENTOR(S) : Harald Martijn Ijsbrand Kerkkamp et al.

It is certified that error appears in the above-identified patent and that said Letters Patent is hereby corrected as shown below:

In the Specification

| | | | |
|---|---|---|---|
| | Column 1, | Line 51, | change "(N. Høibyet al.," to --(N. Høiby et al.,-- |
| | Column 1, | Line 58, | change "(N. Høibyet al.," to --(N. Høiby et al.,-- |
| | Column 12, | Line 63, | change "that kills≥99.9% of" to --that kills ≥99.9% of-- |
| | Column 15, | Line 40, | change "(SEQ ID NO:25))." to --(SEQ ID NO:25),).-- |
| | Column 16, | Lines 27-28, | change "3-β-methyl-4-nitrobenzyl)-L-histidine" to --3-(3-methyl-4-nitrobenzyl)-L-histidine-- |
| | Column 16, | Lines 36-37, | change "lysine, 6,6,6-trimethyl lysine," to --lysine, ε,ε,ε-trimethyl lysine,-- |
| | Column 18, | Lines 44-45, | change "include PEG2, PEGS, PEGS, PEG11," to --include PEG2, PEG3, PEG5, PEG11,-- |
| | Column 19, | Line 54, | change "(SP 11) (SEQ ID" to --(SP11) (SEQ ID-- |
| | Column 21, | Line 23, | change "SEQ ID NO: 97 and SEQ ID NO: 44-54," to --SEQ ID NO:97 and SEQ ID NO:44-54,-- |
| | Column 30, | Line 46, | change "*carinii, Babesia micron, Trypanosoma*" to --*carinii, Babesia microti, Trypanosoma*-- |
| | Column 33, | Line 43, | change "/sites/default/file s/160518" to --/sites/default/files/160518-- |
| | Column 33, | Line 66, | change "*in B 16F10-bearing mice.*" to --*in B16F10-bearing mice.*-- |
| | Column 34, | Line 3, | change "Vol. 39: p8′7-96." to --Vol. 39: p87-96.-- |
| | Column 52, | Line 24, | change "PEG2, PEGS, PEGS, PEG11," to --PEG2, PEG3, PEG5, PEG11,-- |

In the Claims

| | | | |
|---|---|---|---|
| Claim 2, | Column 103, | Lines 18-19, | change "peptide (Currently pharmaceutically" to --peptide pharmaceutically -- |

Signed and Sealed this
Twenty-second Day of October, 2024

Katherine Kelly Vidal
*Director of the United States Patent and Trademark Office*

| | | | |
|---|---|---|---|
| Claim 3, | Column 103, | Line 26, | change "for bacterial infection" to --for a bacterial infection-- |

SEQUENCE LISTING

```
Sequence total quantity: 179
SEQ ID NO: 1            moltype = AA  length = 40
FEATURE                 Location/Qualifiers
source                  1..40
                        mol_type = protein
                        organism = synthetic construct
SEQUENCE: 1
RKFKKSFKKI RKWVKKATKI AGEVAVEILI TKVILGSVGL                          40

SEQ ID NO: 2            moltype = AA  length = 37
FEATURE                 Location/Qualifiers
source                  1..37
                        mol_type = protein
                        organism = synthetic construct
SEQUENCE: 2
KRVKRFKKFF KKVKKSVKKR LKKIFKKPMV IGVTIPF                             37

SEQ ID NO: 3            moltype = AA  length = 34
FEATURE                 Location/Qualifiers
source                  1..34
                        mol_type = protein
                        organism = synthetic construct
SEQUENCE: 3
KRFKKFFKKL KNSVKKRVKK FFRKPRVIGV TFPF                                34

SEQ ID NO: 4            moltype = AA  length = 34
FEATURE                 Location/Qualifiers
source                  1..34
                        mol_type = protein
                        organism = synthetic construct
SEQUENCE: 4
KRFKKFFKKL KNNVKKRVKK FFRKPRVIGV TIPF                                34

SEQ ID NO: 5            moltype = AA  length = 34
FEATURE                 Location/Qualifiers
source                  1..34
                        mol_type = protein
                        organism = synthetic construct
SEQUENCE: 5
KRFKKFFRKL KKSVKKRAKE FFKKPRVIGV SIPF                                34

SEQ ID NO: 6            moltype = AA  length = 34
FEATURE                 Location/Qualifiers
source                  1..34
                        mol_type = protein
                        organism = synthetic construct
SEQUENCE: 6
KRFKKFFKKV KKSVKKRLKK IFKKPMVIGV TIPF                                34

SEQ ID NO: 7            moltype = AA  length = 34
FEATURE                 Location/Qualifiers
source                  1..34
                        mol_type = protein
                        organism = synthetic construct
SEQUENCE: 7
KRFKKFFKKV KKSVKKRLKK IFKKPMVIGV SIPF                                34

SEQ ID NO: 8            moltype = AA  length = 34
FEATURE                 Location/Qualifiers
source                  1..34
                        mol_type = protein
                        organism = synthetic construct
SEQUENCE: 8
KRFRKFFKRL LKSVRRAVKK FRKKPRLIGL STLL                                34

SEQ ID NO: 9            moltype = AA  length = 34
FEATURE                 Location/Qualifiers
source                  1..34
                        mol_type = protein
                        organism = synthetic construct
SEQUENCE: 9
KRFKKFFKKV KKSVKKRLKK IFKKPMVIGV TFPF                                34

SEQ ID NO: 10           moltype = AA  length = 34
FEATURE                 Location/Qualifiers
source                  1..34
                        mol_type = protein
                        organism = synthetic construct
```

-continued

```
SEQUENCE: 10
KRFKKFFRKL KKSVKKRVKK FFKKPRVIGV TIPF                       34

SEQ ID NO: 11           moltype = AA  length = 34
FEATURE                 Location/Qualifiers
source                  1..34
                        mol_type = protein
                        organism = synthetic construct
SEQUENCE: 11
KRFKKFFMKL KKSVKKRVMK FFKKPMVIGV TFPF                       34

SEQ ID NO: 12           moltype = AA  length = 34
FEATURE                 Location/Qualifiers
source                  1..34
                        mol_type = protein
                        organism = synthetic construct
SEQUENCE: 12
KRFKKFFKKA KKSVKKRLKK FFNKTRVIGV SIPF                       34

SEQ ID NO: 13           moltype = AA  length = 31
FEATURE                 Location/Qualifiers
source                  1..31
                        mol_type = protein
                        organism = synthetic construct
SEQUENCE: 13
KRFKKFFRKI KKGFRKIFKK TKIFIGGTIP I                          31

SEQ ID NO: 14           moltype = AA  length = 31
FEATURE                 Location/Qualifiers
source                  1..31
                        mol_type = protein
                        organism = synthetic construct
SEQUENCE: 14
KRFQNFFREL EKKFREFFRV YRITIGATIR F                          31

SEQ ID NO: 15           moltype = AA  length = 31
FEATURE                 Location/Qualifiers
source                  1..31
                        mol_type = protein
                        organism = synthetic construct
SEQUENCE: 15
KRFKDFFHRI RDGVRDFFRN NHFVCGVNFR F                          31

SEQ ID NO: 16           moltype = AA  length = 31
FEATURE                 Location/Qualifiers
source                  1..31
                        mol_type = protein
                        organism = synthetic construct
SEQUENCE: 16
KRFKKFFKKI KTGIKKVIKK TKQAIASHFR W                          31

SEQ ID NO: 17           moltype = AA  length = 30
FEATURE                 Location/Qualifiers
source                  1..30
                        mol_type = protein
                        organism = synthetic construct
SEQUENCE: 17
KRFLRVFKKL KRGIRKLFKK KKIVTGPLTS                            30

SEQ ID NO: 18           moltype = AA  length = 25
FEATURE                 Location/Qualifiers
source                  1..25
                        mol_type = protein
                        organism = synthetic construct
SEQUENCE: 18
AREKSFLQKM KVILQLSSQD QIQAF                                 25

SEQ ID NO: 19           moltype = AA  length = 17
FEATURE                 Location/Qualifiers
source                  1..17
                        mol_type = protein
                        organism = synthetic construct
SEQUENCE: 19
KRFAGFFQFV IGVSFHF                                          17

SEQ ID NO: 20           moltype = AA  length = 42
FEATURE                 Location/Qualifiers
source                  1..42
                        mol_type = protein
```

```
                        organism = synthetic construct
SEQUENCE: 20
DQVERGNFAK DGSKARVKKS LTKWVKFLKK IIAKLGRPLI GF                      42

SEQ ID NO: 21           moltype = AA  length = 34
FEATURE                 Location/Qualifiers
source                  1..34
                        mol_type = protein
                        organism = synthetic construct
SEQUENCE: 21
KRFKKFFKKI KNSVKKRVKK FFKKPRVIGV SIPF                               34

SEQ ID NO: 22           moltype = AA  length = 34
FEATURE                 Location/Qualifiers
source                  1..34
                        mol_type = protein
                        organism = synthetic construct
SEQUENCE: 22
KRFKKFFKKL KNSVRKCAKK FFKKLRVIRV SIPF                               34

SEQ ID NO: 23           moltype = AA  length = 34
FEATURE                 Location/Qualifiers
source                  1..34
                        mol_type = protein
                        organism = synthetic construct
SEQUENCE: 23
KRFKKFFKKV KKSVKKRLKK IFKKPIVIGV SIPF                               34

SEQ ID NO: 24           moltype = AA  length = 33
FEATURE                 Location/Qualifiers
source                  1..33
                        mol_type = protein
                        organism = synthetic construct
SEQUENCE: 24
KRFTFYKKVK KNVENLLNKF FKKLRVIGDS IPF                                33

SEQ ID NO: 25           moltype = AA  length = 33
FEATURE                 Location/Qualifiers
source                  1..33
                        mol_type = protein
                        organism = synthetic construct
SEQUENCE: 25
KRFKKFFRKV KKGVHRYFKK NKFYIAATIP YYG                                33

SEQ ID NO: 26           moltype = AA  length = 32
FEATURE                 Location/Qualifiers
source                  1..32
                        mol_type = protein
                        organism = synthetic construct
SEQUENCE: 26
KRFLRLVVFK KLKKGLRKLF KKKKIVTGHV TS                                 32

SEQ ID NO: 27           moltype = AA  length = 31
FEATURE                 Location/Qualifiers
source                  1..31
                        mol_type = protein
                        organism = synthetic construct
SEQUENCE: 27
KRFKNFFKKI RDGIHEFIHN NRFVIGVNFR F                                  31

SEQ ID NO: 28           moltype = AA  length = 31
FEATURE                 Location/Qualifiers
source                  1..31
                        mol_type = protein
                        organism = synthetic construct
SEQUENCE: 28
KRFKKFFKKI KNGIKTFIKK TQMAIGSHFR W                                  31

SEQ ID NO: 29           moltype = AA  length = 31
FEATURE                 Location/Qualifiers
source                  1..31
                        mol_type = protein
                        organism = synthetic construct
SEQUENCE: 29
KRFKNFFKRV RDGIRDFFRK NHIVIGVNFR F                                  31

SEQ ID NO: 30           moltype = AA  length = 30
FEATURE                 Location/Qualifiers
source                  1..30
```

```
                        mol_type = protein
                        organism = synthetic construct
SEQUENCE: 30
KRFLRVFRKL KKGLKKLFKR KKVVTGYVTA                                   30

SEQ ID NO: 31           moltype = AA  length = 17
FEATURE                 Location/Qualifiers
source                  1..17
                        mol_type = protein
                        organism = synthetic construct
SEQUENCE: 31
KRFAGFFQFV VGVSFRF                                                 17

SEQ ID NO: 32           moltype = AA  length = 17
FEATURE                 Location/Qualifiers
source                  1..17
                        mol_type = protein
                        organism = synthetic construct
SEQUENCE: 32
KRFVGSFQLV VGVSFRF                                                 17

SEQ ID NO: 33           moltype = AA  length = 30
FEATURE                 Location/Qualifiers
source                  1..30
                        mol_type = protein
                        organism = synthetic construct
SEQUENCE: 33
KRFKKFLKKL KKSVKKHVKE FFKKPRVIGV                                   30

SEQ ID NO: 34           moltype = AA  length = 15
FEATURE                 Location/Qualifiers
source                  1..15
                        mol_type = protein
                        organism = synthetic construct
SEQUENCE: 34
VKKGVHRYFK KNKFY                                                   15

SEQ ID NO: 35           moltype = AA  length = 16
FEATURE                 Location/Qualifiers
source                  1..16
                        mol_type = protein
                        organism = synthetic construct
SEQUENCE: 35
KVKKGVHRYF KKNKFY                                                  16

SEQ ID NO: 36           moltype = AA  length = 17
FEATURE                 Location/Qualifiers
source                  1..17
                        mol_type = protein
                        organism = synthetic construct
SEQUENCE: 36
RKVKKGVHRY FKKNKFY                                                 17

SEQ ID NO: 37           moltype = AA  length = 18
FEATURE                 Location/Qualifiers
source                  1..18
                        mol_type = protein
                        organism = synthetic construct
SEQUENCE: 37
FRKVKKGVHR YFKKNKFY                                                18

SEQ ID NO: 38           moltype = AA  length = 19
FEATURE                 Location/Qualifiers
source                  1..19
                        mol_type = protein
                        organism = synthetic construct
SEQUENCE: 38
FFRKVKKGVH RYFKKNKFY                                               19

SEQ ID NO: 39           moltype = AA  length = 20
FEATURE                 Location/Qualifiers
source                  1..20
                        mol_type = protein
                        organism = synthetic construct
SEQUENCE: 39
KFFRKVKKGV HRYFKKNKFY                                              20

SEQ ID NO: 40           moltype = AA  length = 21
FEATURE                 Location/Qualifiers
```

```
source                  1..21
                        mol_type = protein
                        organism = synthetic construct
SEQUENCE: 40
KKFFRKVKKG VHRYFKKNKF Y                                                21

SEQ ID NO: 41           moltype = AA  length = 22
FEATURE                 Location/Qualifiers
source                  1..22
                        mol_type = protein
                        organism = synthetic construct
SEQUENCE: 41
FKKFFRKVKK GVHRYFKKNK FY                                               22

SEQ ID NO: 42           moltype = AA  length = 23
FEATURE                 Location/Qualifiers
source                  1..23
                        mol_type = protein
                        organism = synthetic construct
SEQUENCE: 42
RFKKFFRKVK KGVHRYFKKN KFY                                              23

SEQ ID NO: 43           moltype = AA  length = 24
FEATURE                 Location/Qualifiers
source                  1..24
                        mol_type = protein
                        organism = synthetic construct
SEQUENCE: 43
KRFKKFFRKV KKGVHRYFKK NKFY                                             24

SEQ ID NO: 44           moltype = AA  length = 24
FEATURE                 Location/Qualifiers
source                  1..24
                        mol_type = protein
                        organism = synthetic construct
SEQUENCE: 44
RFKKFFRKVK KGVHRYFKKN KFYI                                             24

SEQ ID NO: 45           moltype = AA  length = 24
FEATURE                 Location/Qualifiers
source                  1..24
                        mol_type = protein
                        organism = synthetic construct
SEQUENCE: 45
FKKFFRKVKK GVHRYFKKNK FYIA                                             24

SEQ ID NO: 46           moltype = AA  length = 24
FEATURE                 Location/Qualifiers
source                  1..24
                        mol_type = protein
                        organism = synthetic construct
SEQUENCE: 46
KKFFRKVKKG VHRYFKKNKF YIAA                                             24

SEQ ID NO: 47           moltype = AA  length = 24
FEATURE                 Location/Qualifiers
source                  1..24
                        mol_type = protein
                        organism = synthetic construct
SEQUENCE: 47
KFFRKVKKGV HRYFKKNKFY IAAT                                             24

SEQ ID NO: 48           moltype = AA  length = 24
FEATURE                 Location/Qualifiers
source                  1..24
                        mol_type = protein
                        organism = synthetic construct
SEQUENCE: 48
FFRKVKKGVH RYFKKNKFYI AATI                                             24

SEQ ID NO: 49           moltype = AA  length = 24
FEATURE                 Location/Qualifiers
source                  1..24
                        mol_type = protein
                        organism = synthetic construct
SEQUENCE: 49
FRKVKKGVHR YFKKNKFYIA ATIP                                             24

SEQ ID NO: 50           moltype = AA  length = 24
```

```
FEATURE                Location/Qualifiers
source                 1..24
                       mol_type = protein
                       organism = synthetic construct
SEQUENCE: 50
RKVKKGVHRY FKKNKFYIAA TIPY                                          24

SEQ ID NO: 51          moltype = AA  length = 24
FEATURE                Location/Qualifiers
source                 1..24
                       mol_type = protein
                       organism = synthetic construct
SEQUENCE: 51
KVKKGVHRYF KKNKFYIAAT IPYY                                          24

SEQ ID NO: 52          moltype = AA  length = 24
FEATURE                Location/Qualifiers
source                 1..24
                       mol_type = protein
                       organism = synthetic construct
SEQUENCE: 52
VKKGVHRYFK KNKFYIAATI PYYG                                          24

SEQ ID NO: 53          moltype = AA  length = 20
FEATURE                Location/Qualifiers
source                 1..20
                       mol_type = protein
                       organism = synthetic construct
SEQUENCE: 53
KFFRKVKKGV HRYFKKNKFY                                               20

SEQ ID NO: 54          moltype = AA  length = 15
FEATURE                Location/Qualifiers
source                 1..15
                       mol_type = protein
                       organism = synthetic construct
SEQUENCE: 54
VKKGVHRYFK KNKFY                                                    15

SEQ ID NO: 55          moltype = AA  length = 33
FEATURE                Location/Qualifiers
source                 1..33
                       mol_type = protein
                       organism = synthetic construct
SEQUENCE: 55
ARFKKFFRKV KKGVHRYFKK NKFYIAATIP YYG                                33

SEQ ID NO: 56          moltype = AA  length = 33
FEATURE                Location/Qualifiers
source                 1..33
                       mol_type = protein
                       organism = synthetic construct
SEQUENCE: 56
KAFKKFFRKV KKGVHRYFKK NKFYIAATIP YYG                                33

SEQ ID NO: 57          moltype = AA  length = 33
FEATURE                Location/Qualifiers
source                 1..33
                       mol_type = protein
                       organism = synthetic construct
SEQUENCE: 57
KRAKKFFRKV KKGVHRYFKK NKFYIAATIP YYG                                33

SEQ ID NO: 58          moltype = AA  length = 33
FEATURE                Location/Qualifiers
source                 1..33
                       mol_type = protein
                       organism = synthetic construct
SEQUENCE: 58
KRFAKFFRKV KKGVHRYFKK NKFYIAATIP YYG                                33

SEQ ID NO: 59          moltype = AA  length = 33
FEATURE                Location/Qualifiers
source                 1..33
                       mol_type = protein
                       organism = synthetic construct
SEQUENCE: 59
KRFKAFFRKV KKGVHRYFKK NKFYIAATIP YYG                                33
```

-continued

```
SEQ ID NO: 60          moltype = AA  length = 33
FEATURE                Location/Qualifiers
source                 1..33
                       mol_type = protein
                       organism = synthetic construct
SEQUENCE: 60
KRFKKAFRKV KKGVHRYFKK NKFYIAATIP YYG                              33

SEQ ID NO: 61          moltype = AA  length = 33
FEATURE                Location/Qualifiers
source                 1..33
                       mol_type = protein
                       organism = synthetic construct
SEQUENCE: 61
KRFKKFARKV KKGVHRYFKK NKFYIAATIP YYG                              33

SEQ ID NO: 62          moltype = AA  length = 33
FEATURE                Location/Qualifiers
source                 1..33
                       mol_type = protein
                       organism = synthetic construct
SEQUENCE: 62
KRFKKFFAKV KKGVHRYFKK NKFYIAATIP YYG                              33

SEQ ID NO: 63          moltype = AA  length = 33
FEATURE                Location/Qualifiers
source                 1..33
                       mol_type = protein
                       organism = synthetic construct
SEQUENCE: 63
KRFKKFFRAV KKGVHRYFKK NKFYIAATIP YYG                              33

SEQ ID NO: 64          moltype = AA  length = 33
FEATURE                Location/Qualifiers
source                 1..33
                       mol_type = protein
                       organism = synthetic construct
SEQUENCE: 64
KRFKKFFRKA KKGVHRYFKK NKFYIAATIP YYG                              33

SEQ ID NO: 65          moltype = AA  length = 33
FEATURE                Location/Qualifiers
source                 1..33
                       mol_type = protein
                       organism = synthetic construct
SEQUENCE: 65
KRFKKFFRKV AKGVHRYFKK NKFYIAATIP YYG                              33

SEQ ID NO: 66          moltype = AA  length = 33
FEATURE                Location/Qualifiers
source                 1..33
                       mol_type = protein
                       organism = synthetic construct
SEQUENCE: 66
KRFKKFFRKV KAGVHRYFKK NKFYIAATIP YYG                              33

SEQ ID NO: 67          moltype = AA  length = 33
FEATURE                Location/Qualifiers
source                 1..33
                       mol_type = protein
                       organism = synthetic construct
SEQUENCE: 67
KRFKKFFRKV KKAVHRYFKK NKFYIAATIP YYG                              33

SEQ ID NO: 68          moltype = AA  length = 33
FEATURE                Location/Qualifiers
source                 1..33
                       mol_type = protein
                       organism = synthetic construct
SEQUENCE: 68
KRFKKFFRKV KKGAHRYFKK NKFYIAATIP YYG                              33

SEQ ID NO: 69          moltype = AA  length = 33
FEATURE                Location/Qualifiers
source                 1..33
                       mol_type = protein
                       organism = synthetic construct
SEQUENCE: 69
KRFKKFFRKV KKGVARYFKK NKFYIAATIP YYG                              33
```

```
SEQ ID NO: 70          moltype = AA  length = 33
FEATURE                Location/Qualifiers
source                 1..33
                       mol_type = protein
                       organism = synthetic construct
SEQUENCE: 70
KRFKKFFRKV KKGVHAYFKK NKFYIAATIP YYG                              33

SEQ ID NO: 71          moltype = AA  length = 33
FEATURE                Location/Qualifiers
source                 1..33
                       mol_type = protein
                       organism = synthetic construct
SEQUENCE: 71
KRFKKFFRKV KKGVHRAFKK NKFYIAATIP YYG                              33

SEQ ID NO: 72          moltype = AA  length = 33
FEATURE                Location/Qualifiers
source                 1..33
                       mol_type = protein
                       organism = synthetic construct
SEQUENCE: 72
KRFKKFFRKV KKGVHRYAKK NKFYIAATIP YYG                              33

SEQ ID NO: 73          moltype = AA  length = 33
FEATURE                Location/Qualifiers
source                 1..33
                       mol_type = protein
                       organism = synthetic construct
SEQUENCE: 73
KRFKKFFRKV KKGVHRYFAK NKFYIAATIP YYG                              33

SEQ ID NO: 74          moltype = AA  length = 33
FEATURE                Location/Qualifiers
source                 1..33
                       mol_type = protein
                       organism = synthetic construct
SEQUENCE: 74
KRFKKFFRKV KKGVHRYFKA NKFYIAATIP YYG                              33

SEQ ID NO: 75          moltype = AA  length = 33
FEATURE                Location/Qualifiers
source                 1..33
                       mol_type = protein
                       organism = synthetic construct
SEQUENCE: 75
KRFKKFFRKV KKGVHRYFKK AKFYIAATIP YYG                              33

SEQ ID NO: 76          moltype = AA  length = 33
FEATURE                Location/Qualifiers
source                 1..33
                       mol_type = protein
                       organism = synthetic construct
SEQUENCE: 76
KRFKKFFRKV KKGVHRYFKK NAFYIAATIP YYG                              33

SEQ ID NO: 77          moltype = AA  length = 33
FEATURE                Location/Qualifiers
source                 1..33
                       mol_type = protein
                       organism = synthetic construct
SEQUENCE: 77
KRFKKFFRKV KKGVHRYFKK NKAYIAATIP YYG                              33

SEQ ID NO: 78          moltype = AA  length = 33
FEATURE                Location/Qualifiers
source                 1..33
                       mol_type = protein
                       organism = synthetic construct
SEQUENCE: 78
KRFKKFFRKV KKGVHRYFKK NKFAIAATIP YYG                              33

SEQ ID NO: 79          moltype = AA  length = 33
FEATURE                Location/Qualifiers
source                 1..33
                       mol_type = protein
                       organism = synthetic construct
SEQUENCE: 79
```

-continued

```
KRFKKFFRKV KKGVHRYFKK NKFYAAATIP YYG                        33

SEQ ID NO: 80          moltype = AA  length = 33
FEATURE                Location/Qualifiers
source                 1..33
                       mol_type = protein
                       organism = synthetic construct
SEQUENCE: 80
KRFKKFFRKV KKGVHRYFKK NKFYIAAAIP YYG                        33

SEQ ID NO: 81          moltype = AA  length = 33
FEATURE                Location/Qualifiers
source                 1..33
                       mol_type = protein
                       organism = synthetic construct
SEQUENCE: 81
KRFKKFFRKV KKGVHRYFKK NKFYIAATAP YYG                        33

SEQ ID NO: 82          moltype = AA  length = 33
FEATURE                Location/Qualifiers
source                 1..33
                       mol_type = protein
                       organism = synthetic construct
SEQUENCE: 82
KRFKKFFRKV KKGVHRYFKK NKFYIAATIA YYG                        33

SEQ ID NO: 83          moltype = AA  length = 33
FEATURE                Location/Qualifiers
source                 1..33
                       mol_type = protein
                       organism = synthetic construct
SEQUENCE: 83
KRFKKFFRKV KKGVHRYFKK NKFYIAATIP AYG                        33

SEQ ID NO: 84          moltype = AA  length = 33
FEATURE                Location/Qualifiers
source                 1..33
                       mol_type = protein
                       organism = synthetic construct
SEQUENCE: 84
KRFKKFFRKV KKGVHRYFKK NKFYIAATIP YAG                        33

SEQ ID NO: 85          moltype = AA  length = 33
FEATURE                Location/Qualifiers
source                 1..33
                       mol_type = protein
                       organism = synthetic construct
SEQUENCE: 85
KRFKKFFRKV KKGVHRYFKK NKFYIAATIP YYA                        33

SEQ ID NO: 86          moltype = AA  length = 33
FEATURE                Location/Qualifiers
source                 1..33
                       mol_type = protein
                       organism = synthetic construct
SITE                   2
                       note = D-tyrosine
SITE                   3
                       note = D-tyrosine
SITE                   4
                       note = D-proline
SITE                   5
                       note = D-isoleucine
SITE                   6
                       note = D-threonine
SITE                   7
                       note = D-alanine
SITE                   8
                       note = D-alanine
SITE                   9
                       note = D-isoleucine
SITE                   10
                       note = D-tyrosine
SITE                   11
                       note = D-phenylalanine
SITE                   12
                       note = D-lysine
SITE                   13
                       note = D-asparagine
```

```
SITE                  14
                      note = D-lysine
SITE                  15
                      note = D-lysine
SITE                  16
                      note = D-phenylalanine
SITE                  17
                      note = D-tyrosine
SITE                  18
                      note = D-arginine
SITE                  19
                      note = D-histidine
SITE                  20
                      note = D-valine
SITE                  22
                      note = D-lysine
SITE                  23
                      note = D-lysine
SITE                  24
                      note = D-valine
SITE                  25
                      note = D-lysine
SITE                  26
                      note = D-arginine
SITE                  27
                      note = D-phenylalanine
SITE                  28
                      note = D-phenylalanine
SITE                  29
                      note = D-lysine
SITE                  30
                      note = D-lysine
SITE                  31
                      note = D-phenylalanine
SITE                  32
                      note = D-arginine
SITE                  33
                      note = D-lysine
SEQUENCE: 86
GYYPITAAIY FKNKKFYRHV GKKVKRFFKK FRK                               33

SEQ ID NO: 87         moltype = AA  length = 33
FEATURE               Location/Qualifiers
SITE                  33
                      note = coupled to PEG2
source                1..33
                      mol_type = protein
                      organism = synthetic construct
SEQUENCE: 87
KRFKKFFRKV KKGVHRYFKK NKFYIAATIP YYG                               33

SEQ ID NO: 88         moltype = AA  length = 33
FEATURE               Location/Qualifiers
SITE                  33
                      note = coupled to PEG3
source                1..33
                      mol_type = protein
                      organism = synthetic construct
SEQUENCE: 88
KRFKKFFRKV KKGVHRYFKK NKFYIAATIP YYG                               33

SEQ ID NO: 89         moltype = AA  length = 33
FEATURE               Location/Qualifiers
SITE                  33
                      note = coupled to PEG5
source                1..33
                      mol_type = protein
                      organism = synthetic construct
SEQUENCE: 89
KRFKKFFRKV KKGVHRYFKK NKFYIAATIP YYG                               33

SEQ ID NO: 90         moltype = AA  length = 33
FEATURE               Location/Qualifiers
SITE                  33
                      note = coupled to PEG11
source                1..33
                      mol_type = protein
                      organism = synthetic construct
SEQUENCE: 90
```

```
KRFKKFFRKV KKGVHRYFKK NKFYIAATIP YYG                      33

SEQ ID NO: 91          moltype = AA  length = 33
FEATURE                Location/Qualifiers
SITE                   33
                       note = coupled to PEG27
source                 1..33
                       mol_type = protein
                       organism = synthetic construct
SEQUENCE: 91
KRFKKFFRKV KKGVHRYFKK NKFYIAATIP YYG                      33

SEQ ID NO: 92          moltype = AA  length = 33
FEATURE                Location/Qualifiers
SITE                   1
                       note = coupled to PEG2
source                 1..33
                       mol_type = protein
                       organism = synthetic construct
SEQUENCE: 92
KRFKKFFRKV KKGVHRYFKK NKFYIAATIP YYG                      33

SEQ ID NO: 93          moltype = AA  length = 33
FEATURE                Location/Qualifiers
SITE                   1
                       note = coupled to PEG3
source                 1..33
                       mol_type = protein
                       organism = synthetic construct
SEQUENCE: 93
KRFKKFFRKV KKGVHRYFKK NKFYIAATIP YYG                      33

SEQ ID NO: 94          moltype = AA  length = 33
FEATURE                Location/Qualifiers
SITE                   1
                       note = coupled to PEG5
source                 1..33
                       mol_type = protein
                       organism = synthetic construct
SEQUENCE: 94
KRFKKFFRKV KKGVHRYFKK NKFYIAATIP YYG                      33

SEQ ID NO: 95          moltype = AA  length = 33
FEATURE                Location/Qualifiers
SITE                   1
                       note = coupled to PEG11
source                 1..33
                       mol_type = protein
                       organism = synthetic construct
SEQUENCE: 95
KRFKKFFRKV KKGVHRYFKK NKFYIAATIP YYG                      33

SEQ ID NO: 96          moltype = AA  length = 33
FEATURE                Location/Qualifiers
SITE                   1
                       note = coupled to PEG27
source                 1..33
                       mol_type = protein
                       organism = synthetic construct
SEQUENCE: 96
KRFKKFFRKV KKGVHRYFKK NKFYIAATIP YYG                      33

SEQ ID NO: 97          moltype = AA  length = 24
FEATURE                Location/Qualifiers
SITE                   24
                       note = coupled to PEG2
source                 1..24
                       mol_type = protein
                       organism = synthetic construct
SEQUENCE: 97
KRFKKFFRKV KKGVHRYFKK NKFY                                24

SEQ ID NO: 98          moltype = AA  length = 24
FEATURE                Location/Qualifiers
SITE                   24
                       note = coupled to PEG3
source                 1..24
                       mol_type = protein
                       organism = synthetic construct
```

```
SEQUENCE: 98
KRFKKFFRKV KKGVHRYFKK NKFY                                       24

SEQ ID NO: 99          moltype = AA  length = 24
FEATURE                Location/Qualifiers
SITE                   24
                       note = coupled to PEG5
source                 1..24
                       mol_type = protein
                       organism = synthetic construct
SEQUENCE: 99
KRFKKFFRKV KKGVHRYFKK NKFY                                       24

SEQ ID NO: 100         moltype = AA  length = 24
FEATURE                Location/Qualifiers
SITE                   24
                       note = coupled to PEG11
source                 1..24
                       mol_type = protein
                       organism = synthetic construct
SEQUENCE: 100
KRFKKFFRKV KKGVHRYFKK NKFY                                       24

SEQ ID NO: 101         moltype = AA  length = 24
FEATURE                Location/Qualifiers
SITE                   24
                       note = coupled to PEG27
source                 1..24
                       mol_type = protein
                       organism = synthetic construct
SEQUENCE: 101
KRFKKFFRKV KKGVHRYFKK NKFY                                       24

SEQ ID NO: 102         moltype = AA  length = 24
FEATURE                Location/Qualifiers
SITE                   1
                       note = coupled to PEG2
source                 1..24
                       mol_type = protein
                       organism = synthetic construct
SEQUENCE: 102
KRFKKFFRKV KKGVHRYFKK NKFY                                       24

SEQ ID NO: 103         moltype = AA  length = 24
FEATURE                Location/Qualifiers
SITE                   1
                       note = coupled to PEG3
source                 1..24
                       mol_type = protein
                       organism = synthetic construct
SEQUENCE: 103
KRFKKFFRKV KKGVHRYFKK NKFY                                       24

SEQ ID NO: 104         moltype = AA  length = 24
FEATURE                Location/Qualifiers
SITE                   1
                       note = coupled to PEG5
source                 1..24
                       mol_type = protein
                       organism = synthetic construct
SEQUENCE: 104
KRFKKFFRKV KKGVHRYFKK NKFY                                       24

SEQ ID NO: 105         moltype = AA  length = 24
FEATURE                Location/Qualifiers
SITE                   1
                       note = coupled to PEG11
source                 1..24
                       mol_type = protein
                       organism = synthetic construct
SEQUENCE: 105
KRFKKFFRKV KKGVHRYFKK NKFY                                       24

SEQ ID NO: 106         moltype = AA  length = 24
FEATURE                Location/Qualifiers
SITE                   1
                       note = coupled to PEG27
source                 1..24
                       mol_type = protein
```

```
                          organism = synthetic construct
SEQUENCE: 106
KRFKKFFRKV KKGVHRYFKK NKFY                                           24

SEQ ID NO: 107            moltype = AA  length = 33
FEATURE                   Location/Qualifiers
SITE                      1
                          note = Homolysine (hLys)
source                    1..33
                          mol_type = protein
                          organism = synthetic construct
SEQUENCE: 107
XRFKKFFRKV KKGVHRYFKK NKFYIAATIP YYG                                 33

SEQ ID NO: 108            moltype = AA  length = 33
FEATURE                   Location/Qualifiers
SITE                      1
                          note = epsilon-Methyl lysine (Lys(Me))
source                    1..33
                          mol_type = protein
                          organism = synthetic construct
SEQUENCE: 108
XRFKKFFRKV KKGVHRYFKK NKFYIAATIP YYG                                 33

SEQ ID NO: 109            moltype = AA  length = 33
FEATURE                   Location/Qualifiers
SITE                      1
                          note = epsilon, epsilon -Dimethyl lysine (Lys(Me)2)
source                    1..33
                          mol_type = protein
                          organism = synthetic construct
SEQUENCE: 109
XRFKKFFRKV KKGVHRYFKK NKFYIAATIP YYG                                 33

SEQ ID NO: 110            moltype = AA  length = 33
FEATURE                   Location/Qualifiers
SITE                      1
                          note = epsilon, epsilon, epsilon -Trimethyl lysine
                           (Lys(Me)3)
source                    1..33
                          mol_type = protein
                          organism = synthetic construct
SEQUENCE: 110
XRFKKFFRKV KKGVHRYFKK NKFYIAATIP YYG                                 33

SEQ ID NO: 111            moltype = AA  length = 33
FEATURE                   Location/Qualifiers
SITE                      1
                          note = Ornithine (Orn)
source                    1..33
                          mol_type = protein
                          organism = synthetic construct
SEQUENCE: 111
XRFKKFFRKV KKGVHRYFKK NKFYIAATIP YYG                                 33

SEQ ID NO: 112            moltype = AA  length = 33
FEATURE                   Location/Qualifiers
SITE                      1
                          note = 2,3-Diaminopropanoic acid (Dap)
source                    1..33
                          mol_type = protein
                          organism = synthetic construct
SEQUENCE: 112
XRFKKFFRKV KKGVHRYFKK NKFYIAATIP YYG                                 33

SEQ ID NO: 113            moltype = AA  length = 33
FEATURE                   Location/Qualifiers
SITE                      1
                          note = 2,4-Diaminobutanoic acid (Dab)
source                    1..33
                          mol_type = protein
                          organism = synthetic construct
SEQUENCE: 113
XRFKKFFRKV KKGVHRYFKK NKFYIAATIP YYG                                 33

SEQ ID NO: 114            moltype = AA  length = 33
FEATURE                   Location/Qualifiers
SITE                      2
                          note = Homoarginine (hArg)
```

```
source                1..33
                      mol_type = protein
                      organism = synthetic construct
SEQUENCE: 114
KXFKKFFRKV KKGVHRYFKK NKFYIAATIP YYG                              33

SEQ ID NO: 115        moltype = AA  length = 33
FEATURE               Location/Qualifiers
SITE                  2
                      note = Methylarginine (Arg(Me))
source                1..33
                      mol_type = protein
                      organism = synthetic construct
SEQUENCE: 115
KXFKKFFRKV KKGVHRYFKK NKFYIAATIP YYG                              33

SEQ ID NO: 116        moltype = AA  length = 33
FEATURE               Location/Qualifiers
SITE                  2
                      note = Asym. dimethylarginine (ADMA)
source                1..33
                      mol_type = protein
                      organism = synthetic construct
SEQUENCE: 116
KXFKKFFRKV KKGVHRYFKK NKFYIAATIP YYG                              33

SEQ ID NO: 117        moltype = AA  length = 33
FEATURE               Location/Qualifiers
SITE                  2
                      note = Shortend Arg (Agb)
source                1..33
                      mol_type = protein
                      organism = synthetic construct
SEQUENCE: 117
KXFKKFFRKV KKGVHRYFKK NKFYIAATIP YYG                              33

SEQ ID NO: 118        moltype = AA  length = 33
FEATURE               Location/Qualifiers
SITE                  2
                      note = Citrulline (Cit)
source                1..33
                      mol_type = protein
                      organism = synthetic construct
SEQUENCE: 118
KXFKKFFRKV KKGVHRYFKK NKFYIAATIP YYG                              33

SEQ ID NO: 119        moltype = AA  length = 33
FEATURE               Location/Qualifiers
SITE                  3
                      note = Homophenylalanine (hPhe)
source                1..33
                      mol_type = protein
                      organism = synthetic construct
SEQUENCE: 119
KRXKKFFRKV KKGVHRYFKK NKFYIAATIP YYG                              33

SEQ ID NO: 120        moltype = AA  length = 33
FEATURE               Location/Qualifiers
SITE                  3
                      note = Homotyrosine (hTyr)
source                1..33
                      mol_type = protein
                      organism = synthetic construct
SEQUENCE: 120
KRXKKFFRKV KKGVHRYFKK NKFYIAATIP YYG                              33

SEQ ID NO: 121        moltype = AA  length = 33
FEATURE               Location/Qualifiers
SITE                  3
                      note = Phenylglycine (Phg)
source                1..33
                      mol_type = protein
                      organism = synthetic construct
SEQUENCE: 121
KRXKKFFRKV KKGVHRYFKK NKFYIAATIP YYG                              33

SEQ ID NO: 122        moltype = AA  length = 33
FEATURE               Location/Qualifiers
SITE                  3
```

-continued

```
                         note = 4-Fluorophenylalanine (Phe(4-F))
source                   1..33
                         mol_type = protein
                         organism = synthetic construct
SEQUENCE: 122
KRXKKFFRKV KKGVHRYFKK NKFYIAATIP YYG                                33

SEQ ID NO: 123           moltype = AA  length = 33
FEATURE                  Location/Qualifiers
SITE                     3
                         note = 4-Chlorophenylalanine (Phe(4-Cl))
source                   1..33
                         mol_type = protein
                         organism = synthetic construct
SEQUENCE: 123
KRXKKFFRKV KKGVHRYFKK NKFYIAATIP YYG                                33

SEQ ID NO: 124           moltype = AA  length = 33
FEATURE                  Location/Qualifiers
SITE                     3
                         note = 4-Cyanophenylalanine (Phe(4-CN))
source                   1..33
                         mol_type = protein
                         organism = synthetic construct
SEQUENCE: 124
KRXKKFFRKV KKGVHRYFKK NKFYIAATIP YYG                                33

SEQ ID NO: 125           moltype = AA  length = 33
FEATURE                  Location/Qualifiers
SITE                     3
                         note = 4-Nitrophenylalanine (Phe(4-NO2))
source                   1..33
                         mol_type = protein
                         organism = synthetic construct
SEQUENCE: 125
KRXKKFFRKV KKGVHRYFKK NKFYIAATIP YYG                                33

SEQ ID NO: 126           moltype = AA  length = 33
FEATURE                  Location/Qualifiers
SITE                     3
                         note = Cyclohexylalanine (Cha)
source                   1..33
                         mol_type = protein
                         organism = synthetic construct
SEQUENCE: 126
KRXKKFFRKV KKGVHRYFKK NKFYIAATIP YYG                                33

SEQ ID NO: 127           moltype = AA  length = 33
FEATURE                  Location/Qualifiers
SITE                     10
                         note = Norvaline (Nva)
source                   1..33
                         mol_type = protein
                         organism = synthetic construct
SEQUENCE: 127
KRFKKFFRKX KKGVHRYFKK NKFYIAATIP YYG                                33

SEQ ID NO: 128           moltype = AA  length = 33
FEATURE                  Location/Qualifiers
SITE                     10
                         note = homoleucine (hLeu)
source                   1..33
                         mol_type = protein
                         organism = synthetic construct
SEQUENCE: 128
KRFKKFFRKX KKGVHRYFKK NKFYIAATIP YYG                                33

SEQ ID NO: 129           moltype = AA  length = 33
FEATURE                  Location/Qualifiers
SITE                     10
                         note = Norleucine (Nle)
source                   1..33
                         mol_type = protein
                         organism = synthetic construct
SEQUENCE: 129
KRFKKFFRKX KKGVHRYFKK NKFYIAATIP YYG                                33

SEQ ID NO: 130           moltype = AA  length = 33
FEATURE                  Location/Qualifiers
```

```
SITE                    10
                        note = 2-Aminobutyric acid (Abu)
source                  1..33
                        mol_type = protein
                        organism = synthetic construct
SEQUENCE: 130
KRFKKFFRKX KKGVHRYFKK NKFYIAATIP YYG                         33

SEQ ID NO: 131          moltype = AA  length = 33
FEATURE                 Location/Qualifiers
SITE                    15
                        note = 1-Methylhistidine (His(1-Me)
source                  1..33
                        mol_type = protein
                        organism = synthetic construct
SEQUENCE: 131
KRFKKFFRKV KKGVXRYFKK NKFYIAATIP YYG                         33

SEQ ID NO: 132          moltype = AA  length = 33
FEATURE                 Location/Qualifiers
SITE                    15
                        note = 3-Methylhistidine (His(3-Me)
source                  1..33
                        mol_type = protein
                        organism = synthetic construct
SEQUENCE: 132
KRFKKFFRKV KKGVXRYFKK NKFYIAATIP YYG                         33

SEQ ID NO: 133          moltype = AA  length = 33
FEATURE                 Location/Qualifiers
SITE                    17
                        note = O-Methyltyrosine (Tyr(OMe))
source                  1..33
                        mol_type = protein
                        organism = synthetic construct
SEQUENCE: 133
KRFKKFFRKV KKGVHRXFKK NKFYIAATIP YYG                         33

SEQ ID NO: 134          moltype = AA  length = 33
FEATURE                 Location/Qualifiers
SITE                    17
                        note = Homotyrosine (hTyr)
source                  1..33
                        mol_type = protein
                        organism = synthetic construct
SEQUENCE: 134
KRFKKFFRKV KKGVHRXFKK NKFYIAATIP YYG                         33

SEQ ID NO: 135          moltype = AA  length = 33
FEATURE                 Location/Qualifiers
SITE                    17
                        note = Homophenylalanine (hPhe)
source                  1..33
                        mol_type = protein
                        organism = synthetic construct
SEQUENCE: 135
KRFKKFFRKV KKGVHRXFKK NKFYIAATIP YYG                         33

SEQ ID NO: 136          moltype = AA  length = 33
FEATURE                 Location/Qualifiers
SITE                    17
                        note = 4-Fluorophenylalanine (Phe(4-F))
source                  1..33
                        mol_type = protein
                        organism = synthetic construct
SEQUENCE: 136
KRFKKFFRKV KKGVHRXFKK NKFYIAATIP YYG                         33

SEQ ID NO: 137          moltype = AA  length = 33
FEATURE                 Location/Qualifiers
SITE                    17
                        note = 4-Chlorophenylalanine (Phe(4-Cl))
source                  1..33
                        mol_type = protein
                        organism = synthetic construct
SEQUENCE: 137
KRFKKFFRKV KKGVHRXFKK NKFYIAATIP YYG                         33

SEQ ID NO: 138          moltype = AA  length = 33
```

-continued

```
FEATURE                Location/Qualifiers
SITE                   17
                       note = 4-Cyanophenylalanine (Phe(4-CN))
source                 1..33
                       mol_type = protein
                       organism = synthetic construct
SEQUENCE: 138
KRFKKFFRKV KKGVHRXFKK NKFYIAATIP YYG                              33

SEQ ID NO: 139         moltype = AA  length = 33
FEATURE                Location/Qualifiers
SITE                   17
                       note = 4-Nitrophenylalanine (Phe(4-NO2))
source                 1..33
                       mol_type = protein
                       organism = synthetic construct
SEQUENCE: 139
KRFKKFFRKV KKGVHRXFKK NKFYIAATIP YYG                              33

SEQ ID NO: 140         moltype = AA  length = 33
FEATURE                Location/Qualifiers
SITE                   17
                       note = Dihydroxyphenylalanine (DOPA)
source                 1..33
                       mol_type = protein
                       organism = synthetic construct
SEQUENCE: 140
KRFKKFFRKV KKGVHRXFKK NKFYIAATIP YYG                              33

SEQ ID NO: 141         moltype = AA  length = 33
FEATURE                Location/Qualifiers
SITE                   25
                       note = Norvaline (Nva)
source                 1..33
                       mol_type = protein
                       organism = synthetic construct
SEQUENCE: 141
KRFKKFFRKV KKGVHRYFKK NKFYXAATIP YYG                              33

SEQ ID NO: 142         moltype = AA  length = 33
FEATURE                Location/Qualifiers
SITE                   25
                       note = Homoleucine (hLeu)
source                 1..33
                       mol_type = protein
                       organism = synthetic construct
SEQUENCE: 142
KRFKKFFRKV KKGVHRYFKK NKFYXAATIP YYG                              33

SEQ ID NO: 143         moltype = AA  length = 33
FEATURE                Location/Qualifiers
SITE                   25
                       note = Norleucine (Nle)
source                 1..33
                       mol_type = protein
                       organism = synthetic construct
SEQUENCE: 143
KRFKKFFRKV KKGVHRYFKK NKFYXAATIP YYG                              33

SEQ ID NO: 144         moltype = AA  length = 33
FEATURE                Location/Qualifiers
SITE                   25
                       note = 2-Aminobutyric acid (Abu)
source                 1..33
                       mol_type = protein
                       organism = synthetic construct
SEQUENCE: 144
KRFKKFFRKV KKGVHRYFKK NKFYXAATIP YYG                              33

SEQ ID NO: 145         moltype = AA  length = 33
FEATURE                Location/Qualifiers
SITE                   30
                       note = Hydroxyproline (Hyp)
source                 1..33
                       mol_type = protein
                       organism = synthetic construct
SEQUENCE: 145
KRFKKFFRKV KKGVHRYFKK NKFYIAATIX YYG                              33
```

-continued

```
SEQ ID NO: 146          moltype = AA  length = 33
FEATURE                 Location/Qualifiers
SITE                    30
                        note = Isonipecotic acid (Isn)
source                  1..33
                        mol_type = protein
                        organism = synthetic construct
SEQUENCE: 146
KRFKKFFRKV KKGVHRYFKK NKFYIAATIX YYG                                33

SEQ ID NO: 147          moltype = AA  length = 33
FEATURE                 Location/Qualifiers
SITE                    30
                        note = Thiaproline (Thz)
source                  1..33
                        mol_type = protein
                        organism = synthetic construct
SEQUENCE: 147
KRFKKFFRKV KKGVHRYFKK NKFYIAATIX YYG                                33

SEQ ID NO: 148          moltype = AA  length = 33
FEATURE                 Location/Qualifiers
source                  1..33
                        mol_type = protein
                        organism = synthetic construct
SITE                    1
                        note = D-lysine
SITE                    2
                        note = D-arginine
SITE                    3
                        note = D-phenylalanine
SITE                    4
                        note = D-lysine
SITE                    5
                        note = D-lysine
SITE                    6
                        note = D-phenylalanine
SITE                    7
                        note = D-phenylalanine
SITE                    8
                        note = D-arginine
SITE                    9
                        note = D-lysine
SITE                    10
                        note = D-valine
SITE                    11
                        note = D-lysine
SITE                    12
                        note = D-lysine
SITE                    14
                        note = D-valine
SITE                    15
                        note = D-histidine
SITE                    16
                        note = D-arginine
SITE                    17
                        note = D-tyrosine
SITE                    18
                        note = D-phenylalanine
SITE                    19
                        note = D-lysine
SITE                    20
                        note = D-lysine
SITE                    21
                        note = D-asparagine
SITE                    22
                        note = D-lysine
SITE                    23
                        note = D-phenylalanine
SITE                    24
                        note = D-tyrosine
SITE                    25
                        note = D-isoleucine
SITE                    26
                        note = D-alanine
SITE                    27
                        note = D-alanine
SITE                    28
                        note = D-threonine
```

-continued

```
SITE                   29
                       note = D-isoleucine
SITE                   30
                       note = D-proline
SITE                   31
                       note = D-tyrosine
SITE                   32
                       note = D-tyrosine
SEQUENCE: 148
KRFKKFFRKV KKGVHRYFKK NKFYIAATIP YYG                              33

SEQ ID NO: 149         moltype = AA  length = 33
FEATURE                Location/Qualifiers
source                 1..33
                       mol_type = protein
                       organism = synthetic construct
SITE                   1
                       note = D-lysine
SEQUENCE: 149
KRFKKFFRKV KKGVHRYFKK NKFYIAATIP YYG                              33

SEQ ID NO: 150         moltype = AA  length = 33
FEATURE                Location/Qualifiers
source                 1..33
                       mol_type = protein
                       organism = synthetic construct
SITE                   2
                       note = D-arginine
SEQUENCE: 150
KRFKKFFRKV KKGVHRYFKK NKFYIAATIP YYG                              33

SEQ ID NO: 151         moltype = AA  length = 33
FEATURE                Location/Qualifiers
source                 1..33
                       mol_type = protein
                       organism = synthetic construct
SITE                   3
                       note = D-phenylalanine
SEQUENCE: 151
KRFKKFFRKV KKGVHRYFKK NKFYIAATIP YYG                              33

SEQ ID NO: 152         moltype = AA  length = 33
FEATURE                Location/Qualifiers
source                 1..33
                       mol_type = protein
                       organism = synthetic construct
SITE                   4
                       note = D-lysine
SEQUENCE: 152
KRFKKFFRKV KKGVHRYFKK NKFYIAATIP YYG                              33

SEQ ID NO: 153         moltype = AA  length = 33
FEATURE                Location/Qualifiers
source                 1..33
                       mol_type = protein
                       organism = synthetic construct
SITE                   5
                       note = D-lysine
SEQUENCE: 153
KRFKKFFRKV KKGVHRYFKK NKFYIAATIP YYG                              33

SEQ ID NO: 154         moltype = AA  length = 33
FEATURE                Location/Qualifiers
source                 1..33
                       mol_type = protein
                       organism = synthetic construct
SITE                   6
                       note = D-phenylalanine
SEQUENCE: 154
KRFKKFFRKV KKGVHRYFKK NKFYIAATIP YYG                              33

SEQ ID NO: 155         moltype = AA  length = 33
FEATURE                Location/Qualifiers
source                 1..33
                       mol_type = protein
                       organism = synthetic construct
SITE                   7
                       note = D-phenylalanine
SEQUENCE: 155
```

```
KRFKKFFRKV KKGVHRYFKK NKFYIAATIP YYG                              33

SEQ ID NO: 156          moltype = AA  length = 33
FEATURE                 Location/Qualifiers
source                  1..33
                        mol_type = protein
                        organism = synthetic construct
SITE                    8
                        note = D-arginine
SEQUENCE: 156
KRFKKFFRKV KKGVHRYFKK NKFYIAATIP YYG                              33

SEQ ID NO: 157          moltype = AA  length = 33
FEATURE                 Location/Qualifiers
source                  1..33
                        mol_type = protein
                        organism = synthetic construct
SITE                    9
                        note = D-lysine
SEQUENCE: 157
KRFKKFFRKV KKGVHRYFKK NKFYIAATIP YYG                              33

SEQ ID NO: 158          moltype = AA  length = 33
FEATURE                 Location/Qualifiers
source                  1..33
                        mol_type = protein
                        organism = synthetic construct
SITE                    10
                        note = D-valine
SEQUENCE: 158
KRFKKFFRKV KKGVHRYFKK NKFYIAATIP YYG                              33

SEQ ID NO: 159          moltype = AA  length = 33
FEATURE                 Location/Qualifiers
source                  1..33
                        mol_type = protein
                        organism = synthetic construct
SITE                    11
                        note = D-lysine
SEQUENCE: 159
KRFKKFFRKV KKGVHRYFKK NKFYIAATIP YYG                              33

SEQ ID NO: 160          moltype = AA  length = 33
FEATURE                 Location/Qualifiers
source                  1..33
                        mol_type = protein
                        organism = synthetic construct
SITE                    12
                        note = D-lysine
SEQUENCE: 160
KRFKKFFRKV KKGVHRYFKK NKFYIAATIP YYG                              33

SEQ ID NO: 161          moltype = AA  length = 33
FEATURE                 Location/Qualifiers
source                  1..33
                        mol_type = protein
                        organism = synthetic construct
SITE                    14
                        note = D-valine
SEQUENCE: 161
KRFKKFFRKV KKGVHRYFKK NKFYIAATIP YYG                              33

SEQ ID NO: 162          moltype = AA  length = 33
FEATURE                 Location/Qualifiers
source                  1..33
                        mol_type = protein
                        organism = synthetic construct
SITE                    15
                        note = D-histidine
SEQUENCE: 162
KRFKKFFRKV KKGVHRYFKK NKFYIAATIP YYG                              33

SEQ ID NO: 163          moltype = AA  length = 33
FEATURE                 Location/Qualifiers
source                  1..33
                        mol_type = protein
                        organism = synthetic construct
SITE                    16
                        note = D-arginine
```

-continued

```
SEQUENCE: 163
KRFKKFFRKV KKGVHRYFKK NKFYIAATIP YYG                         33

SEQ ID NO: 164          moltype = AA  length = 33
FEATURE                 Location/Qualifiers
source                  1..33
                        mol_type = protein
                        organism = synthetic construct
SITE                    17
                        note = D-tyrosine
SEQUENCE: 164
KRFKKFFRKV KKGVHRYFKK NKFYIAATIP YYG                         33

SEQ ID NO: 165          moltype = AA  length = 33
FEATURE                 Location/Qualifiers
source                  1..33
                        mol_type = protein
                        organism = synthetic construct
SITE                    18
                        note = D-phenylalanine
SEQUENCE: 165
KRFKKFFRKV KKGVHRYFKK NKFYIAATIP YYG                         33

SEQ ID NO: 166          moltype = AA  length = 33
FEATURE                 Location/Qualifiers
source                  1..33
                        mol_type = protein
                        organism = synthetic construct
SITE                    19
                        note = D-lysine
SEQUENCE: 166
KRFKKFFRKV KKGVHRYFKK NKFYIAATIP YYG                         33

SEQ ID NO: 167          moltype = AA  length = 33
FEATURE                 Location/Qualifiers
source                  1..33
                        mol_type = protein
                        organism = synthetic construct
SITE                    20
                        note = D-lysine
SEQUENCE: 167
KRFKKFFRKV KKGVHRYFKK NKFYIAATIP YYG                         33

SEQ ID NO: 168          moltype = AA  length = 33
FEATURE                 Location/Qualifiers
source                  1..33
                        mol_type = protein
                        organism = synthetic construct
SITE                    21
                        note = D-asparagine
SEQUENCE: 168
KRFKKFFRKV KKGVHRYFKK NKFYIAATIP YYG                         33

SEQ ID NO: 169          moltype = AA  length = 33
FEATURE                 Location/Qualifiers
source                  1..33
                        mol_type = protein
                        organism = synthetic construct
SITE                    22
                        note = D-lysine
SEQUENCE: 169
KRFKKFFRKV KKGVHRYFKK NKFYIAATIP YYG                         33

SEQ ID NO: 170          moltype = AA  length = 33
FEATURE                 Location/Qualifiers
source                  1..33
                        mol_type = protein
                        organism = synthetic construct
SITE                    23
                        note = D-phenylalanine
SEQUENCE: 170
KRFKKFFRKV KKGVHRYFKK NKFYIAATIP YYG                         33

SEQ ID NO: 171          moltype = AA  length = 33
FEATURE                 Location/Qualifiers
source                  1..33
                        mol_type = protein
                        organism = synthetic construct
SITE                    24
```

```
                        note = D-tyrosine
SEQUENCE: 171
KRFKKFFRKV KKGVHRYFKK NKFYIAATIP YYG                                33

SEQ ID NO: 172          moltype = AA  length = 33
FEATURE                 Location/Qualifiers
source                  1..33
                        mol_type = protein
                        organism = synthetic construct
SITE                    25
                        note = D-isoleucine
SEQUENCE: 172
KRFKKFFRKV KKGVHRYFKK NKFYIAATIP YYG                                33

SEQ ID NO: 173          moltype = AA  length = 33
FEATURE                 Location/Qualifiers
source                  1..33
                        mol_type = protein
                        organism = synthetic construct
SITE                    26
                        note = D-alanine
SEQUENCE: 173
KRFKKFFRKV KKGVHRYFKK NKFYIAATIP YYG                                33

SEQ ID NO: 174          moltype = AA  length = 33
FEATURE                 Location/Qualifiers
source                  1..33
                        mol_type = protein
                        organism = synthetic construct
SITE                    27
                        note = D-alanine
SEQUENCE: 174
KRFKKFFRKV KKGVHRYFKK NKFYIAATIP YYG                                33

SEQ ID NO: 175          moltype = AA  length = 33
FEATURE                 Location/Qualifiers
source                  1..33
                        mol_type = protein
                        organism = synthetic construct
SITE                    28
                        note = D-threonine
SEQUENCE: 175
KRFKKFFRKV KKGVHRYFKK NKFYIAATIP YYG                                33

SEQ ID NO: 176          moltype = AA  length = 33
FEATURE                 Location/Qualifiers
source                  1..33
                        mol_type = protein
                        organism = synthetic construct
SITE                    29
                        note = D-isoleucine
SEQUENCE: 176
KRFKKFFRKV KKGVHRYFKK NKFYIAATIP YYG                                33

SEQ ID NO: 177          moltype = AA  length = 33
FEATURE                 Location/Qualifiers
source                  1..33
                        mol_type = protein
                        organism = synthetic construct
SITE                    30
                        note = D-proline
SEQUENCE: 177
KRFKKFFRKV KKGVHRYFKK NKFYIAATIP YYG                                33

SEQ ID NO: 178          moltype = AA  length = 33
FEATURE                 Location/Qualifiers
source                  1..33
                        mol_type = protein
                        organism = synthetic construct
SITE                    31
                        note = D-tyrosine
SEQUENCE: 178
KRFKKFFRKV KKGVHRYFKK NKFYIAATIP YYG                                33

SEQ ID NO: 179          moltype = AA  length = 33
FEATURE                 Location/Qualifiers
source                  1..33
                        mol_type = protein
                        organism = synthetic construct
```

-continued

```
SITE                  32
                      note = D-tyrosine
SEQUENCE: 179
KRFKKFFRKV KKGVHRYFKK NKFYIAATIP YYG                          33
```